(12) United States Patent
Lee et al.

(10) Patent No.: US 7,674,822 B2
(45) Date of Patent: Mar. 9, 2010

(54) PTP1B INHIBITORS

(75) Inventors: Jinbo Lee, Andover, MA (US); Michael J. Smith, Somerset, NJ (US); Alessandro Fabio Moretto, Somerville, MA (US); Zhao-Kui Wan, Arlington, MA (US); Eva Deanna Binnun, Somerville, MA (US); Weixin Xu, Acton, MA (US); Kenneth W. Foreman, Syosset, NY (US); Diane M. Joseph-McCarthy, Belmont, MA (US); David V. Erbe, Arlington, MA (US); Steve Y. Tam, Wellesley, MA (US)

(73) Assignee: Wyeth, Madison, NJ (US)

( * ) Notice: Subject to any disclaimer, the term of this patent is extended or adjusted under 35 U.S.C. 154(b) by 1085 days.

(21) Appl. No.: 11/285,223

(22) Filed: Nov. 22, 2005

(65) Prior Publication Data

US 2006/0135488 A1     Jun. 22, 2006

Related U.S. Application Data

(60) Provisional application No. 60/630,623, filed on Nov. 24, 2004.

(51) Int. Cl.
*A61K 31/381*     (2006.01)
*C07D 495/04*     (2006.01)

(52) U.S. Cl. .................. 514/443; 514/321; 514/382; 549/45; 549/48; 546/197; 548/250

(58) Field of Classification Search ............ 549/45, 549/48; 514/443, 321, 382; 546/197; 548/250
See application file for complete search history.

(56) References Cited

U.S. PATENT DOCUMENTS

| 546,191 | A | 9/1895 | Rice, Jr. |
|---|---|---|---|
| 4,910,317 | A | 3/1990 | Connor et al. |
| 5,068,248 | A | 11/1991 | Tischler et al. |
| 5,208,253 | A | 5/1993 | Boschelli et al. |
| 5,350,748 | A | 9/1994 | Boschelli et al. |
| 5,356,926 | A | 10/1994 | Boschelli et al. |
| 5,426,113 | A | 6/1995 | Low |
| 5,691,362 | A | 11/1997 | McCormick et al. |
| 5,760,062 | A | 6/1998 | Gaeta et al. |
| 5,863,936 | A | 1/1999 | Gaeta et al. |
| 6,232,320 | B1 | 5/2001 | Stewart et al. |

FOREIGN PATENT DOCUMENTS

| DE | 184496 | 5/1907 |
|---|---|---|
| DE | 1937514 | 2/1970 |
| EP | 146243 | 6/1985 |
| EP | 299457 | 1/1989 |
| EP | 318066 | 5/1989 |
| EP | 403885 | 12/1990 |
| EP | 447891 | 9/1991 |
| EP | 543584 | 5/1993 |
| EP | 655439 | 5/1995 |
| EP | 1092716 | 4/2001 |
| GB | 2193961 | 2/1988 |
| JP | 2001313174 | 11/2001 |
| WO | WO92/03427 | 3/1992 |
| WO | WO95/15323 | 6/1995 |
| WO | WO95/24408 | 9/1995 |
| WO | WO95/33720 | 12/1995 |
| WO | WO96/29077 | 9/1996 |
| WO | WO98/08847 | 3/1998 |
| WO | WO99/40088 | 8/1999 |
| WO | WO99/40091 | 8/1999 |
| WO | WO99/62908 | 12/1999 |
| WO | WO00/71517 | 11/2000 |
| WO | WO00/75145 | 12/2000 |
| WO | WO01/02409 | 1/2001 |
| WO | WO01/96323 | 12/2001 |
| WO | WO02/24703 | 3/2002 |
| WO | WO02/26745 | 4/2002 |
| WO | WO02/28815 | 4/2002 |
| WO | WO02/062799 | 8/2002 |
| WO | WO02/070486 | 9/2002 |
| WO | WO02/085909 | 10/2002 |
| WO | WO02/098400 | 12/2002 |
| WO | WO96/11920 | 4/2006 |
| ZA | 8601709 | 10/1986 |
| ZA | 8605740 | 3/1987 |

OTHER PUBLICATIONS

Justus Lebigs Ann. Chem., 393; 1912; 358.
Justus Lebigs Ann. Chem., 408; 1915; 280.
Chem.Ber; 39; 1906; 1062.
Justus Lebigs Ann. Chem., 351; 1907; 407.
Chem.Ber; 66; 1933; 364, 368.
Chem.Ber; 59; 1926; 1078.
J.Chem. Soc.; 1947; 1574, 1576.

*Primary Examiner*—Bernard Dentz

(57) ABSTRACT

This invention relates to modulating (e.g., inhibiting) protein tyrosine phosphatase 1B (PTP1B).

65 Claims, No Drawings

PTP1B INHIBITORS

CROSS REFERENCE TO RELATED APPLICATIONS

This application claims the benefit of U.S. Provisional Application No. 60/630,623, filed on Nov. 24, 2004, which is incorporated herein by reference in its entirety.

TECHNICAL FIELD

This invention relates to modulating (e.g., inhibiting) protein tyrosine phosphatase 1b (PTP1b).

BACKGROUND

Diabetes is generally characterized by relatively high levels of plasma glucose (hyperglycemia) in the fasting state. Type 2 diabetics can often develop insulin resistance, in which the effect of insulin in stimulating glucose and lipid metabolism is diminished. Further, patients who have developed insulin resistance, but not type 2 diabetes, are also at risk of developing Syndrome X (metabolic syndrome). Syndrome X is characterized by insulin resistance, along with obesity (e.g., abdominal obesity), hyperinsulinemia, high blood pressure, relatively low HDL and relatively high VLDL. Although current treatments for type 2 diabetes can result in reduced levels of blood sugar, side effects can include weight gain, hyperglycemia, edema, and liver toxicity.

Protein tyrosine phosphatase 1b (PTP1b), a ~50 kd intracelluar PTPase abundant in various human tissues, has been studied for its potential role as a negative regulator of insulin signaling. Some studies have shown that PTP1b is a negative regulator of insulin signaling. For example, mice deficient in PTP1b were healthy and showed increased insulin sensitivity and resistance to diet-induced obesity. These mice had lower glucose, insulin and triglyceride levels as well as improved insulin sensitivity as measured by glucose and insulin tolerance tests. PTP1b has also been implicated in attenuation of leptin receptor signaling. PTP1b deficient mice were shown to be more sensitive to leptin, which may explain in part their resistance to weight gain when placed on a high fat diet. Thus, the main target tissues for PTP1b inhibition appear to be insulin action in muscle and liver, as well as leptin signaling in the brain, while the commercial diabetes drugs, the peroxisome proliferative activated receptor-gamma (PPAR-γ) agonist class of insulin sensitizers, target adipose tissue. Thus inhibition of PTP1b provides a target for regulating a variety of cellular responses important to human diseases related to obesity and type 2 diabetes.

SUMMARY

In one aspect, this invention relates to compounds having formula (I):

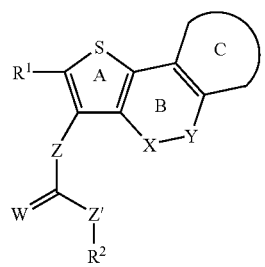

in which:
X can be $C(R^a)(R^b)$, $NR^c$, or S;
Y can be $C(R^d)(R^e)$, $NR^f$, or a bond; provided that when X is S, Y is a bond, and further provided that X and Y are not simultaneously $NR^c$ and $NR^f$, respectively ring C can be:
  (i) a fused $C_6$-$C_{16}$ aryl or a fused heteroaryl including 5-16 atoms, each of which can be optionally substituted with from 1-10 $R^3$; or
  (ii) a fused $C_3$-$C_{10}$ cycloalkyl, a fused $C_3$-$C_{10}$ cycloalkenyl, a fused heterocyclyl including 5-10 atoms, or a fused heterocycloalkenyl including 5-10 atoms, each of which can be optionally substituted with from 1-5 $R^4$;
$R^1$ can be:
  (i) $C_6$-$C_{16}$ aryl or heteroaryl including 5-16 atoms, each of which can be optionally substituted with from 1-10 $R^g$; or
  (ii) $C_3$-$C_{16}$ cycloalkyl or $C_3$-$C_{16}$ halocycloalkyl, each of which can be optionally substituted with from 1-5 $R^h$; or
  (iii) $C_3$-$C_{10}$ cycloalkenyl, heterocyclyl including 5-10 atoms, or heterocycloalkenyl including 5-10 atoms, each of which can be optionally substituted with from 1-5 $R^i$; or
  (iv) cyano, —$C(O)R^j$, —$C(O)OR^j$, —$OC(O)R^j$, —$C(O)SR^j$, —$SC(O)R^j$, —$C(S)SR^j$, —$SC(S)R^j$, —$NR^kC(O)R^j$, —$C(O)NR^mR^n$; or —$C(NR^o)R^j$;
W can be O or S;
each of Z and Z' can be, independently:
  (i) O, $NR^p$, S, SO, or $SO_2$; or
  (ii) $C_1$-$C_{12}$ alkylene, $C_2$-$C_{12}$ alkenylene, $C_2$-$C_{12}$ alkynylene, $O(C_1$-$C_{12}$ alkylene), $O(C_2$-$C_{12}$ alkenylene), $O(C_2$-$C_{12}$ alkynylene), $NR^p(C_1$-$C_{12}$ alkylene), $NR^p(C_2$-$C_{12}$ alkenylene), $NR^p(C_2$-$C_{12}$ alkynylene), $S(C_1$-$C_{12}$ alkylene), $S(C_2$-$C_{12}$ alkenylene), $S(C_2$-$C_{12}$ alkynylene), $SO(C_1$-$C_{12}$ alkylene), $SO(C_2$-$C_{12}$ alkenylene), $SO(C_2$-$C_{12}$ alkynylene), $SO_2(C_1$-$C_{12}$ alkylene), $SO_2(C_2$-$C_{12}$ alkenylene), or $SO_2(C_2$-$C_{12}$ alkynylene), each of which is optionally substituted with 1-5 $R^q$;
$R^2$ can be:
  (i) hydrogen; or
  (ii) $C_1$-$C_{20}$ alkyl, optionally substituted with from 1-10 $R^r$ and/or optionally inserted with from 1-10 heteroatoms selected from the group consisting of nitrogen, oxygen or sulfur; or
  (iii) $C_1$-$C_{20}$ haloalkyl, optionally substituted with from 1-10 $R^r$; or
  (iv) $C_3$-$C_{20}$ cycloalkyl or $C_3$-$C_{20}$ halocycloalkyl, optionally substituted with from 1-10 $R^h$; or
  (v) $C_3$-$C_{20}$ cycloalkenyl, heterocyclyl including 3-20 atoms, or heterocycloalkenyl including 3-20 atoms, each of which can be optionally substituted with from 1-10 $R^i$; or
  (vi) $C_2$-$C_{20}$ alkenyl or $C_2$-$C_{20}$ alkynyl, each of which can be optionally substituted with from 1-10 $R^s$;
  (vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which can be optionally substituted with from 1-10 $R^t$; or (viii) $C_6$-$C_{16}$ aryl or heteroaryl including 5-16 atoms, each of which can be optionally substituted with from 1-10 $R^g$;

each of $R^3$ and $R^4$, can be, independently:

(i) halo; $NR^mR^n$; nitro; azido, hydroxy; oxo; thioxo; =$NR^o$; $OR^m$ (e.g., $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$); mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; N$R^k$C(O)N$R^mR^n$; N$R^k$C(O)O$R^j$; —S(O)$_n$$R^u$; —N$R^k$S(O)$_n$$R^j$; or —P(O)(O$R^m$)(O$R^n$); or (ii) $C_1$-$C_{20}$ alkyl, optionally substituted with from 1-10 $R^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 $R^r$; or (iv) $C_3$-$C_{20}$ cycloalkyl or $C_3$-$C_{20}$ halocycloalkyl, optionally substituted with from 1-10 $R^h$; or (v) $C_3$-$C_{20}$ cycloalkenyl, heterocyclyl including 3-20 atoms, or heterocycloalkenyl including 3-20 atoms, each of which can be optionally substituted with from 1-10 $R^i$; or (vi) $C_2$-$C_{20}$ alkenyl or $C_2$-$C_{20}$ alkynyl, each of which can be optionally substituted with from 1-10 $R^s$;

(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which can be optionally substituted with from 1-10 $R^t$; or (viii) $C_6$-$C_{16}$ aryl or heteroaryl including 5-16 atoms, each of which can be optionally substituted with from 1-10 $R^g$;

each of $R^a$ and $R^b$ can be, independently, hydrogen or $C_1$-$C_{10}$ alkyl; or one of $R^a$ and $R^b$ is hydrogen or $C_1$-$C_{10}$ alkyl, and the other together with $R^d$, $R^e$, or $R^f$ can be a bond;

$R^c$ can be hydrogen or $C_1$-$C_6$ alkyl; or $R^c$ together with $R^d$ or $R^e$ can be a bond;

each of $R^d$ and $R^e$ can be, independently, hydrogen or $C_1$-$C_{10}$ alkyl; or one of $R^d$ and $R^e$ can be hydrogen or $C_1$-$C_6$ alkyl, and the other together with $R^a$, $R^b$, or $R^c$ can be a bond;

$R^f$ can be hydrogen or $C_1$-$C_6$ alkyl; or $R^f$ together with $R^a$ or $R^b$ can be a bond;

$R^g$ at each occurrence can be, independently:

(i) halo; $NR^mR^n$; nitro; azido, hydroxy; $C_1$-$C_{12}$ alkoxy, optionally substituted with 1-5 $R^r$; $C_1$-$C_2$ haloalkoxy; $C_6$-$C_{16}$ aryloxy, optionally substituted with 1-5 $R^g$ or $R^{g'}$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; —N$R^k$C(O)N$R^mR^n$; —N$R^k$C(O)O$R^j$; —S(O)$_n$$R^u$; —N$R^k$S(O)$_n$$R^j$; or —P(O)(O$R^m$)(O$R^n$); or (ii) $C_1$-$C_{12}$ alkyl, optionally substituted with from 1-10 $R^r$ and/or optionally inserted with from 1-6 heteroatoms selected from the group consisting of nitrogen, oxygen or sulfur; or (iii) $C_3$-$C_{20}$ cycloalkyl or $C_3$-$C_{20}$ halocycloalkyl, optionally substituted with from 1-10 $R^h$; or (iv) $C_3$-$C_{20}$ cycloalkenyl, heterocyclyl including 3-20 atoms, or heterocycloalkenyl including 3-20 atoms, each of which is optionally substituted with from 1-10 $R^i$; or (v) $C_2$-$C_{20}$ alkenyl or $C_2$-$C_{20}$ alkynyl, each of which is optionally substituted with from 1-10 $R^s$; or (vi) $C_1$-$C_{12}$ haloalkyl; or (vii) $C_7$-$C_{20}$ aralkyl or heteroaralkyl including 6-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$ or $R^{g'}$;

$R^{g'}$ at each occurrence can be, independently, $C_1$-$C_{12}$ alkyl, $C_1$-$C_{12}$ haloalkyl, $C_2$-$C_{12}$ alkenyl; $C_2$-$C_{12}$ alkynyl; $C_3$-$C_{20}$ cycloalkyl; $C_3$-$C_{20}$ halocycloalkyl; $C_3$-$C_{20}$ cycloalkenyl, heterocyclyl including 3-20 atoms, or heterocycloalkenyl including 3-20 atoms; $C_7$-$C_{20}$ aralkyl; $C_6$-$C_{16}$ aryl or heteroaryl including 5-16 atoms; halo; $NR^mR^n$; nitro; azido, hydroxy; $C_1$-$C_{12}$ alkoxy; $C_1$-$C_{12}$ haloalkoxy; $C_6$-$C_{16}$ aryloxy; $C_2$-$C_{12}$ alkenyloxy; $C_2$-$C_{12}$ alkynyloxy; $C_3$-$C_{16}$ cycloalkyloxy; $C_3$-$C_{16}$ halocycloalkyloxy; heterocyclyloxy including 3-16 atoms; $C_7$-$C_{20}$ aralkoxy; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; —N$R^k$C(O)N$R^mR^n$; —N$R^k$C(O)O$R^j$; —S(O)$_n$$R^u$; —N$R^k$S(O)$_n$$R^j$; or —P(O)(O$R^m$)(O$R^n$);

$R^h$ at each occurrence can be, independently:

(i) $NR^mR^n$; nitro; azido; hydroxy; oxo; thioxo; =$NR^o$; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; —N$R^k$C(O)N$R^mR^n$; N$R^k$C(O)O$R^j$; S(O)$_n$$R^u$; —N$R^k$S(O)$_n$$R^j$; or —P(O)(O$R^m$)(O$R^n$); or (ii) $C_2$-$C_{20}$ alkenyl or $C_2$-$C_{20}$ alkynyl, each of which is optionally substituted with from 1-10 $R^s$; or (iii) $C_6$-$C_{16}$ aryl or heteroaryl including 5-16 atoms, each of which is optionally substituted with from 1-10 $R^g$;

$R^i$ at each occurrence can be, independently:

(i) halo, $NR^mR^n$; nitro; azido; hydroxy; oxo, thioxo, =$NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; —N$R^k$C(O)N$R^mR^n$; N$R^k$C(O)O$R^j$; —S(O)$_n$$R^u$; —N$R^k$S(O)$_n$$R^j$; or —P(O)(O$R^m$)(O$R^n$); or (ii) $C_2$-$C_{20}$ alkenyl or $C_2$-$C_{20}$ alkynyl, each of which can be optionally substituted with from 1-10 $R^s$; or (iii) $C_6$-$C_{16}$ aryl or heteroaryl including 5-16 atoms, each of which can be optionally substituted with from 1-10 $R^g$;

each of $R^j$, $R^k$, $R^m$, and $R^n$, at each occurrence can be, independently:

(i) hydrogen; or (ii) $C_1$-$C_{20}$ alkyl, optionally substituted with from 1-10 $R^r$ and/or optionally inserted with from 1-6 heteroatoms selected from the group consisting of nitrogen, oxygen or sulfur;

(iii) $C_1$-$C_{20}$ haloalkyl; or (iv) $C_2$-$C_{20}$ alkenyl or $C_2$-$C_{20}$ alkynyl, each of which can be optionally substituted with from 1-10 $R^s$; or (v) $C_3$-$C_{20}$ cycloalkyl or $C_3$-$C_{20}$ halocycloalkyl, each of which can be optionally substituted with from 1-10 $R^h$; or (vi) $C_3$-$C_{20}$ cycloalkenyl, heterocyclyl including 3-16 atoms, or heterocycloalkenyl including 3-16 atoms, each of which can be optionally substituted with from 1-10 $R^i$; or (vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which can be optionally substituted with from 1-10 $R^t$; or (viii) $C_6$-$C_{16}$ aryl or heteroaryl including 5-16 atoms, each of which can be optionally substituted with from 1-10 $R^g$;

$R^o$ can be hydrogen; $C_1$-$C_{12}$ alkyl optionally inserted with from 1-6 heteroatoms selected from the group consisting of nitrogen, oxygen or sulfur; $C_2$-$C_{20}$ alkenyl; $C_2$-$C_{20}$ alkynyl; $C_7$-$C_{20}$ aralkyl; heteroaralkyl including 6-20 atoms; $C_3$-$C_{16}$ cycloalkyl; $C_3$-$C_{16}$ cycloalkenyl; heterocyclyl including 3-16 atoms; heterocycloalkenyl including 3-16 atoms; $C_8$-$C_{20}$ arylcycloalkyl; $C_8$-$C_{20}$ arylcycloalkenyl; arylheterocyclyl including 8-20 atoms; or arylheterocycloalkenyl including 8-20 atoms; $C_6$-$C_{16}$ aryl; heteroaryl including 5-16 atoms; $NR^mR^n$, or $OR^j$;

$R^p$ can be hydrogen or $C_1$-$C_{12}$ alkyl;

$R^q$ at each occurrence can be, independently, halo, $NR^mR^n$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which can be optionally substituted with 1-5 $R^s$; $C_3$-$C_{16}$ cycloalkyloxy or $C_3$-$C_{16}$ halocycloalkyloxy, each of which can be optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$);

$R^r$ at each occurrence can be, $NR^mR^n$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which can be optionally substituted with 1-5 $R^s$; $C_3$-$C_{16}$ cycloalkyloxy or $C_3$-$C_{16}$ halocycloalkyloxy, each of which can be optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$);

$R^s$ at each occurrence can be, independently, halo, $NR^mR^n$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which can be optionally substituted with 1-5 $R^s$; $C_3$-$C_{16}$ cycloalkyloxy or $C_3$-$C_{16}$ halocycloalkyloxy, each of which can be optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; $NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$);

$R^t$ at each occurrence can be, independently:

(i) $C_1$-$C_{12}$ alkyl, $C_1$-$C_{12}$ haloalkyl, halo, $NR^mR^n$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; $NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$); or (ii) $C_2$-$C_{20}$ alkenyl or $C_2$-$C_{20}$ alkynyl, each of which can be optionally substituted with from 1-10 $R^s$; or (iii) $C_6$-$C_{16}$ aryl or heteroaryl including 5-16 atoms, each of which can be optionally substituted with from 1-10 $R^g$;

$R^u$ can be $R^j$, $OR^j$, or $NR^mR^n$;

n can be 0, 1 or 2; or a salt (e.g., a pharmaceutically acceptable salt) thereof.

In another aspect, this invention relates to compounds having formula (II):

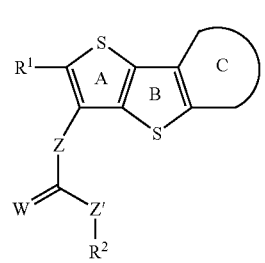

(II)

in which $R^1$, $R^2$, W, Z, Z', ring C, and n can be as defined elsewhere.

In a further aspect, this invention relates to compounds having formula (VII):

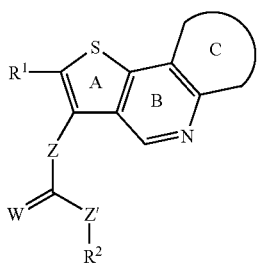

(VII)

in which $R^1$, $R^2$, W, Z, Z', ring C, and n can be as defined elsewhere.

In another aspect, this invention relates to compounds having formula (VI):

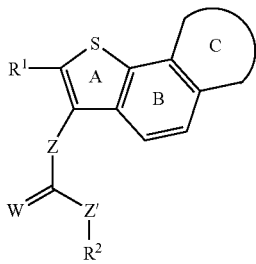

(VIII)

in which $R^1$, $R^2$, W, Z, Z', ring C, and n can be as defined elsewhere.

In a further aspect, this invention relates to compounds having formula (VI):

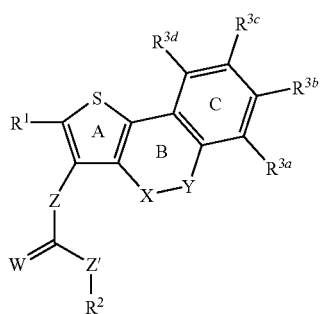

(VI)

in which:

X, Y, $R^1$, $R^2$, W, Z, Z', and n can be as defined elsewhere; and each of $R^{3a}$, $R^{3b}$, $R^{3c}$, and $R^{3d}$ can be, independently:

(i) hydrogen, (i) halo; $NR^mR^n$; nitro; azido, hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^t$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; —N$R^k$C(O)N$R^mR^n$; —N$R^k$C(O)O$R^j$; —S(O)$_nR^u$; —N$R^k$S(O)$_nR^j$; or —P(O)(O$R^m$)(O$R^n$); or (ii) $C_1$-$C_{20}$ alkyl, optionally substituted with from 1-10 $R^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 $R^r$; or (iv) $C_3$-$C_{20}$ cycloalkyl or $C_3$-$C_{20}$ halocycloalkyl, optionally substituted with from 1-10 $R^h$; or (v) $C_3$-$C_{20}$ cycloalkenyl, heterocyclyl including 3-20 atoms, or heterocycloalkenyl including 3-20 atoms, each of which is optionally substituted with from 1-10 $R^t$; or (vi) $C_2$-$C_{20}$ alkenyl or $C_2$-$C_{20}$ alkynyl, each of which is optionally substituted with from 1-10 $R^s$;

(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$.

In another aspect, this invention relates to any of the compounds delineated herein.

In one aspect, this invention relates to methods for treating diabetes (e.g., type 2 diabetes), which includes administering to a subject in need thereof an effective amount of a compound having any of the formulae described herein (e.g., a compound having formula (I), (II), (III), (IV), (V), (VI), (VII), or (VIII) e.g., any of the compounds described herein) or a pharmaceutically acceptable salt thereof.

In one aspect, this invention relates to methods for treating obesity, which includes administering to a subject in need thereof an effective amount of a compound having any of the formulae described herein (e.g., a compound having formula (I), (II), (III), (IV), (V), (VI), (VII), or (VIII) e.g., any of the compounds described herein) or a pharmaceutically acceptable salt thereof.

In one aspect, this invention relates to methods for increasing insulin sensitivity, which includes administering to a subject in need thereof (e.g., a type 2 diabetic) an effective amount of a compound having any of the formulae described herein (e.g., a compound having formula (I), (II), (III), (IV), (V), (VI), (VII), or (VIII) e.g., any of the compounds described herein) or a pharmaceutically acceptable salt thereof.

In one aspect, this invention relates to methods for treating metabolic disorders, which includes administering to a subject in need thereof an effective amount of a compound having any of the formulae described herein (e.g., a compound having formula (I), (II), (III), (IV), (V), (VI), (VII), or (VIII) e.g., any of the compounds described herein) or a pharmaceutically acceptable salt thereof.

The invention also relates generally to inhibiting PTP1b with the compounds described herein. In some embodiments, the methods can include, e.g., contacting a PTP1b in a sample (e.g., a tissue) with a compound having any of the formulae described herein (e.g., a compound having formula (I), (II), (III), (IV), (V), (VI), (VII), or (VIII) e.g., any of the compounds described herein). In other embodiments, the methods can include administering a compound having any of the formulae described herein (e.g., a compound having formula (I), (II), (III), (IV), (V), (VI), (VII), or (VIII) e.g., any of the compounds described herein) to a subject (e.g., a mammal, e.g., a human, e.g., a type 2 diabetic).

In some embodiments, the subject can be a subject in need thereof (e.g., a subject identified as being in need of such treatment). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

In a further aspect, this invention also relates to methods of making compounds described herein. Alternatively, the method includes taking any one of the intermediate compounds described herein and reacting it with one or more chemical reagents in one or more steps to produce a compound described herein.

In one aspect, this invention relates to a packaged product. The packaged product includes a container, one of the aforementioned compounds in the container, and a legend (e.g., a label or an insert) associated with the container and indicating administration of the compound for treatment and control of diseases or disorders mediated by PTP1b, e.g., type 2 diabetes, obesity, metabolic disorders.

In another aspect, the invention relates to a compound (including a pharmaceutically acceptable salt thereof) of any of the formulae delineated herein, or a composition comprising a compound (including a pharmaceutically acceptable salt thereof) of any of the formulae delineated herein. In some embodiments, the composition can further include a pharmaceutically acceptable adjuvant, carrier or diluent and/or an additional therapeutic. agent.

Embodiments can include one or more of the following features.

X can be S.

X can be $C(R^a)(R^b)$ and Y can be $NR^f$. One of $R^a$ and $R^b$ can be hydrogen or $C_1$-$C_4$ alkyl, and the other together with $R^f$ is a bond (e.g., one of $R^a$ and $R^b$ can be hydrogen, and the other together with $R^f$ can be a bond).

X can be $C(R^a)(R^b)$ and Y can be $C(R^d)(R^e)$. One of $R^a$ and $R^b$ can be hydrogen or $C_1$-$C_4$ alkyl, and the other together with $R^d$ or $R^e$ is a bond (e.g., one of $R^a$ and $R^b$ can be hydrogen, and the other together with $R^d$ or $R^e$ can be a bond). One of $R^d$ and $R^e$ can be hydrogen or $C_1$-$C_4$ alkyl, and the other together with $R^a$ or $R^b$ is a bond (e.g., one of $R^d$ and $R^e$ is hydrogen, and the other together with $R^a$ or $R^b$ is a bond).

Each of $R^3$ and $R^4$, can be, independently:

(i) halo; $NR^mR^n$; nitro; hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —$C(O)R^j$; —$C(O)OR^j$; —$OC(O)R^j$; —$C(O)NR^mR^n$; —$NR^kC(O)R^j$; —$OC(O)NR^mR^n$; —$NR^kC(O)NR^mR^n$; —$NR^kC(O)OR^j$; —$S(O)_nR^u$; or —$NR^kS(O)_nR^j$; or (ii) $C_1$-$C_{12}$ alkyl, optionally substituted with from 1-10 $R^r$ and/or optionally inserted with from 1-10 heteroatoms selected from the group consisting of nitrogen, oxygen or sulfur; or (iii) $C_3$-$C_{20}$ cycloalkyl or $C_3$-$C_{20}$ halocycloalkyl, optionally substituted with from 1-10 $R^h$; or (iv) $C_2$-$C_{12}$ alkenyl or $C_2$-$C_{12}$ alkynyl, each of which is optionally substituted with from 1-10 $R^s$; or (v) $C_7$-$C_{12}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (vi) $C_6$-$C_{10}$ aryl or heteroaryl including 5-10 atoms, each of which is optionally substituted with from 1-10 $R^g$.

Each of $R^3$ and $R^4$, is, independently:

(i) halo; $NH_2$; nitro; hydroxy; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR^mR^n$; —$C(O)R^j$, —$C(O)OR^j$; —$OC(O)R^j$; —$C(O)NR^mR^n$; —$NR^k$ $C(O)R^j$; —$OC(O)NR^mR^n$; —$NR^kC(O)NR^mR^n$; $NR^kC(O)OR^j$; —$S(O)_nR^u$; or —$NR^kS(O)_nR^j$; or (ii) $C_1$-$C_6$ alkyl, optionally substituted with from 1-3 $R^r$ and/or optionally inserted with from 1-3 heteroatoms selected from the group consisting of nitrogen, oxygen or sulfur; or (iii) $C_3$-$C_8$ cycloalkyl or $C_3$-$C_8$ halocycloalkyl, optionally substituted with from 1-3 $R^h$; or (iv) $C_2$-$C_6$ alkenyl or $C_2$-$C_6$ alkynyl, each of which is optionally substituted with from 1-3 $R^s$; or (v) $C_7$-$C_{10}$ aralkyl, heteroaralkyl including 6-10 atoms, $C_8$-$C_{10}$ arylcycloalkyl, $C_8$-$C_{10}$ arylcycloalkenyl, arylheterocyclyl including 8-10 atoms, or arylheterocycloalkenyl including 8-10 atoms, each of which is optionally substituted with from 1-5 $R^t$; or (vi) $C_6$ aryl or heteroaryl including 5-6 atoms, each of which is optionally substituted with from 1-5 $R^g$.

$R^s$ and $R^t$, at each occurrence can be, independently, halo; $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR^mR^n$; —$C(O)R^j$, —$C(O)OR^j$; —$OC(O)R^j$; —$C(O)NR^mR^n$; —$NR^kC(O)R^j$; —$OC(O)NR^mR^n$; —$NR^kC(O)NR^mR^n$; —$NR^kC(O)OR^j$; —$S(O)_nR^u$; or —$NR^kS(O)_nR^j$.

$R^h$ and $R^r$, at each occurrence can be, independently, $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR^mR^j$; —$C(O)R^j$, —$C(O)OR^j$; —$OC(O)R^j$; —$C(O)NR^mR^n$; —$NR^kC(O)R^j$; —$OC(O)NR^mR^n$; —$NR^kC(O)NR^mR^n$; —$NR^kC(O)OR^j$; —$S(O)_nR^u$; or —$NR^kS(O)_nR^j$.

$R^g$, at each occurrence can be, independently, halo; $NH_2$, nitro; azido; hydroxy; $C_1$-$C_{12}$ alkoxy, optionally substituted with 1-5 $R^r$; $OCF_3$; $C_6$-$C_{16}$ aryloxy, optionally substituted with 1-5 $R^g$ or $R^{g'}$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)O$R^j$; —C(O)N$R'''R''$; —$NR^k$C(O)$R^i$; —OC(O)$NR'''R''$; —$NR^k$C(O)$NR'''R''$; —$NR^k$C(O)O$R^j$; —S(O)$_n R^u$; or —$NR^k$S(O)$_n R^j$.

Ring C can be a fused $C_6$-$C_{16}$ aryl or a fused heteroaryl including 5-16 atoms, each of which is optionally substituted with from 1-10 $R^3$. Ring C can be a fused $C_6$-$C_0$ aryl, optionally substituted with from 1-5 $R^3$. Ring C can be a fused phenyl ring, optionally substituted with from 1-3 $R^3$. Ring C can be an unsubstituted fused phenyl ring. Ring C can be a fused heteroaryl including 5-10 atoms, each of which is optionally substituted with from 1-5 $R^3$. Ring C can be a fused pyridyl ring, optionally substituted with from 1-3 $R^3$.

$R^3$, at each occurrence can be, independently, halo, $C_1$-$C_6$ alkyl, $C_1$-$C_6$ alkoxy, $C_3$-$C_{10}$ cycloalkyl, $C_7$-$C_{10}$ aralkyl, —C(O)O$R^j$, —C(O)N$R'''R''$, —$NR^k$C(O)O$R^j$, —$NR^k$C(O)NR'''R''$, —$NR^k$C(O)$R^j$, or —$NR'''R''$.

$R^3$ can be halo (e.g., chloro). $R^3$ can be $C_7$-$C_{10}$ aralkyl (e.g., benzyl).

$R^3$ can be —C(O)O$R^j$ (e.g., $R^j$ can be $C_1$-$C_6$ alkyl, e.g., tert-butyl).

$R^3$ can be $C_1$-$C_6$ alkyl (e.g., $CH_3$).

$R^3$ can be $C_1$-$C_6$ alkoxy (e.g., $OCH_3$).

$R^3$ can be $C_3$-$C_{10}$ cycloalkyl (e.g.:

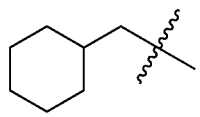

$R^3$ can be —C(O)$NR'''R''$. For example, one of $R'''$ and $R''$ can be hydrogen, and the other can be $C_7$-$C_{10}$ aralkyl (e.g., benzyl). As another example, one of $R'''$ and $R''$ can be hydrogen, and the other can be $C_3$-$C_{10}$ cycloalkyl (e.g.:

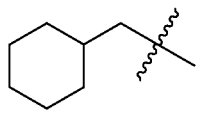

$R^3$ is —$NR^k$C(O)O$R^j$. $R^k$ can be hydrogen. $R^k$ can be $C_3$-$C_{10}$ cycloalkyl (e.g., cyclohexyl). $R^j$ can be $C_1$-$C_6$ alkyl (e.g., is $CH_3$ or tert-butyl).

$^3$ can be —$NR^k$C(O)$NR'''R''$, $R^k$ can be $C_3$-$C_{10}$ cycloalkyl (e.g., cyclohexyl). One of $R'''$ and $R''$ can be hydrogen, and the other can be $C_1$-$C_6$ alkyl (e.g., $CH_2CH_3$).

$R^3$ can be —$NR^k$C(O)$R^j$. $R^k$ can be $C_3$-$C_{10}$ cycloalkyl (e.g., cyclohexyl or

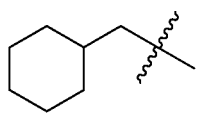

$R^j$ is $C_6$-$C_{10}$ aryl (e.g., phenyl). $R^j$ can be $C_1$-$C_6$ alkyl (e.g., $CH_3$).

$R^3$ can be —$NR'''R''$.

$R'''$ and $R''$ can both be hydrogen.

One of $R'''$ and $R''$ can be hydrogen, and the other can be $C_7$-$C_{10}$ aralkyl (e.g., benzyl).

One of $R'''$ and $R''$ can be hydrogen, and the other can be heterocyclyl including 3-10 atoms, optionally substituted with from 1-3 $R^i$. One of $R'''$ and $R''$ can be hydrogen, and the other can be tetrahydropyranyl. One of $R'''$ and $R''$ is hydrogen, and the other can be:

wherein z can be 1, 2, 3, 4, or 5.

$R^i$ can be —C(O)O$R^j$, —C(O)$NR'''R''$, or C(O)$R^j$. $R^j$ can be $C_1$-$C_6$ alkyl (e.g., tert-butyl). $R^j$ can be $C_1$-$C_6$ haloalkyl. $R^j$ can be $C_6$-$C_{10}$ aryl (e.g., phenyl or naphthyl). $R^j$ can be heteroaryl including from 5-10 atoms (e.g., pyridyl, thienyl, furyl, or imidazolyl). $R^j$ can be $C_7$-$C_{12}$ aralkyl (e.g., benzyl). $R^j$ can be heteroaralkyl including from 7-12 atoms (e.g., pyridylmethyl). $R^j$ can be heterocyclyl including from 3-8 atoms (e.g., piperidinyl). $R^j$ can be $C_3$-$C_{10}$ cycloalkyl (e.g., $R^j$ can be cyclopropyl, cyclobutyl, cyclopentyl, cyclohexyl, cycloheptyl, cyclooctyl, or cyclohexylmethyl). $R^j$ can be $C_1$-$C_6$ alkyl; $C_6$-$C_{10}$ aryl; heteroaryl including from 5-10 atoms; or $C_3$-$C_{10}$ cycloalkyl. Each of $R'''$ and $R''$ can be, independently of one another, hydrogen; $C_1$-$C_6$ alkyl; $C_1$-$C_6$ haloalkyl; $C_6$-$C_{10}$ aryl; heteroaryl including from 5-10 atoms; $C_7$-$C_{12}$ aralkyl; heteroaralkyl including from 7-12 atoms; heterocyclyl including from 3-8 atoms; or $C_3$-$C_{10}$ cycloalkyl (e.g., each of $R'''$ and $R''$ is, independently of one another, hydrogen; $C_1$-$C_6$ alkyl; $C_6$-$C_{10}$ aryl; heteroaryl including from 5-10 atoms; or $C_3$-$C_{10}$ cycloalkyl).

$R^i$ can be —$SO_2 R^u$. $R^u$ can be $C_1$-$C_6$ alkyl (e.g., $CH_2CH_3$). $R^u$ can be $C_7$-$C_{10}$ aralkyl (e.g., benzyl). $R^u$ can be $C_1$-$C_6$ haloalkyl. $R^u$ can be $C_6$-$C_{10}$ aryl. $R^u$ can be phenyl or naphthyl. $R^u$ can be heteroaryl including from 5-10 atoms (e.g., pyridyl, thienyl, furyl, or imidazolyl). $R^u$ can be $C_7$-$C_{12}$ (e.g., $C_7$-$C_{10}$) aralkyl (e.g., benzyl). $R^u$ can be heteroaralkyl including from 7-12 atoms (e.g., pyridylmethyl). $R^u$ can be heterocyclyl including from 3-8 atoms (e.g., piperidinyl). $R^u$ can be $C_3$-$C_{10}$ cycloalkyl (e.g., cyclopropyl, cyclobutyl, cyclopentyl, cyclohexyl, cycloheptyl, cyclooctyl, or cyclohexylmethyl). $R^u$ can be $C_1$-$C_6$ alkyl; $C_6$-$C_{10}$ aryl; heteroaryl including from 5-10 atoms; $C_3$-$C_{10}$ cycloalkyl; $C_7$-$C_{12}$ aralkyl; or heteroaralkyl including from 7-12 atoms.

z can be 0, 1, or 2.

One of $R'''$ and $R''$ can be hydrogen, and the other can be $C_3$-$C_{10}$ cycloalkyl (e.g., cyclohexyl or

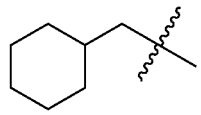

Both $R'''$ and $R''$ can be other than hydrogen.

$R^1$ can be cyano, —C(O)$R^j$, —C(O)O$R^j$, —C(O)S$R^j$, —C(S)S$R^j$, or —C(O)$NR'''R''$. $R^1$ can be cyano. $R^1$ can be —C(O)O$R^j$. $R^j$ can be hydrogen or $C_1$-$C_6$ alkyl.

$R^1$ can be heteroaryl including 5-10 atoms, optionally substituted with from 1-3 $R^g$ (e.g., tetrazolyl).

Z can be O, $NR^p$, S; or $C_1$-$C_{12}$ alkylene, $C_2$-$C_{12}$ alkenylene, $C_2$-$C_{12}$ alkynylene, O($C_1$-$C_{12}$ alkylene), $NR^p$($C_1$-$C_{12}$ alkylene), S($C_1$-$C_{12}$ alkylene), SO($C_1$-$C_{12}$ alkylene), $SO_2$($C_1$-$C_{12}$ alkylene), each of which is optionally substituted with 1-5 $R^q$. Z can be O($C_1$-$C_3$ alkylene), $NR^p$($C_1$-$C_3$ alkylene), S($C_1$-$C_3$ alkylene), SO($C_1$-$C_3$ alkylene), or $SO_2$($C_1$-$C_3$ alkylene), each of which is optionally substituted with 1-5 $R^q$. Z can be $NR^p$($C_1$-$C_3$ alkylene). Z can be O($C_1$-$C_3$ alkylene) (e.g., $OCH_2$).

$R^q$ can be halo; nitro; $NH_2$; hydroxy; oxo; =$NR^o$; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)$R^j$; —C(O)O$R^j$; —OC(O)$R^j$; —C(O)N$R'''R''$; $NR^kC(O)R^j$; —OC(O)N$R'''R''$; —$NR^kC(O)NR'''R''$; —$NR^kC(O)OR^j$; —S(O)$_nR^u$; or —$NR^kS(O)_nR^j$. For example, $R^q$ can be F; Cl; nitro; $NH_2$; hydroxy; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)$R^j$; —C(O)O$R^j$; —OC(O)$R^j$; —C(O)N$R'''R''$; —$NR^kC(O)R^j$; —OC(O)N$R'''R''$; —$NR^kC(O)NR'''R''$; —$NR^kC(O)OR^j$; —S(O)$_nR^u$; or —$NR^kS(O)_nR^j$.

W can be O. Z' can be O.

$R^2$ can be hydrogen.

$R^2$ can be: (i) $C_1$-$C_{16}$ alkyl, optionally substituted with from 1-10 $R^r$ and/or optionally inserted with from 1-10 heteroatoms selected from the group consisting of nitrogen, oxygen or sulfur; or (ii) $C_1$-$C_{16}$ haloalkyl, optionally substituted with from 1-10 $R^r$; or (iii) $C_3$-$C_8$ cycloalkyl or $C_3$-$C_8$ halocycloalkyl, optionally substituted with from 1-5 $R^h$; or (iv) $C_3$-$C_8$ cycloalkenyl, heterocyclyl including 3-8 atoms, or heterocycloalkenyl including 3-8 atoms, each of which is optionally substituted with from 1-5 $R^i$; or (v) $C_2$-$C_{12}$ alkenyl or $C_2$-$C_{12}$ alkynyl, each of which is optionally substituted with from 1-5 $R^s$; (vi) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (vii) $C_6$-$C_{16}$ aryl or heteroaryl including 5-16 atoms, each of which is optionally substituted with from 1-10 $R^g$. for example, $R^2$ can be: (i) $C_1$-$C_{16}$ alkyl, optionally substituted with from 1-10 $R^r$ and/or optionally inserted with from 1-10 heteroatoms selected from the group consisting of nitrogen, oxygen or sulfur; or (vi) $C_7$-$C_{20}$ aralkyl, optionally substituted with from 1-10 $R^t$.

$R^s$, at each occurrence can be, independently, halo; $NH_2$; nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)N$R'''R''$; $NR^kC(O)NR'''R''$; —$NR^kC(O)OR^j$; —S(O)$_nR^u$; or —$NR^kS(O)_nR^j$.

$R^r$, at each occurrence can be, independently, $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; $NR^kC(O)R^j$; —OC(O)N$R'''R''$; $NR^kC(O)NR'''R''$; —$NR^kC(O)OR^j$; —S(O)$_nR^u$; or —$NR^kS(O)_nR^j$.

$R^g$, at each occurrence can be, independently: (i) halo; $NH_2$, nitro; azido; hydroxy; $C_1$-$C_{12}$ alkoxy, optionally substituted with 1-5 $R^r$; $OCF_3$; $C_6$-$C_{16}$ aryloxy, optionally substituted with 1-5 $R^g$ or $R^{g'}$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)O$R^j$; —OC(O)$R^j$; —C(O)N$R'''R''$; —$NR^kC(O)R^j$; —OC(O)N$R'''R''$; —$NR^kC(O)NR'''R''$; —$NR^kC(O)OR^j$; —S(O)$_nR^u$; or —$NR^kS(O)_nR^j$; or (ii) $C_2$-$C_6$ alkenyl or $C_2$-$C_6$ alkynyl.

$R^h$, at each occurrence can be, independently: (i) $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)N$R'''R''$; —$NR^kC(O)NR'''R''$; —$NR^kC(O)OR^j$; —S(O)$_nR^u$; or —$NR^kS(O)_nR^j$; or (ii) $C_2$-$C_6$ alkenyl or $C_2$-$C_6$ alkynyl.

$R^i$, at each occurrence can be, independently: (i) halo; $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)N$R'''R''$; —$NR^kC(O)NR'''R''$; —$NR^kC(O)OR^j$; —S(O)$_nR^u$; or —$NR^kS(O)_nR^j$; or (ii) $C_2$-$C_6$ alkenyl or $C_2$-$C_6$ alkynyl.

One of $R^{3a}$, $R^{3b}$, $R^{3c}$, and $R^{3d}$ can be: (i) halo; $NR'''R''$; nitro; azido, hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl;

—C(O)R$^j$, C$_1$-C$_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; —NR$^k$C(O)NR$^m$R$^n$; —NR$^k$C(O)OR$^j$; —S(O)$_n$R$^u$; —NR$^k$S(O)$_n$R$^j$; or —P(O)(OR$^m$)(OR$^n$); or (ii) C$_1$-C$_{20}$ alkyl, optionally substituted with from 1-10 R$^r$ and/or optionally inserted with from 1-10 heteroatoms selected from the group consisting of nitrogen, oxygen or sulfur; or (iii) C$_1$-C$_{20}$ haloalkyl, optionally substituted with from 1-10 R$^r$; or (iv) C$_3$-C$_{20}$ cycloalkyl or C$_3$-C$_{20}$ halocycloalkyl, optionally substituted with from 1-10 R$^h$; or (v) C$_3$-C$_{20}$ cycloalkenyl, heterocyclyl including 3-20 atoms, or heterocycloalkenyl including 3-20 atoms, each of which is optionally substituted with from 1-10 R$^i$; or (vi) C$_2$-C$_{20}$ alkenyl or C$_2$-C$_{20}$ alkynyl, each of which is optionally substituted with from 1-10 R$^s$; (vii) C$_7$-C$_{20}$ aralkyl, heteroaralkyl including 6-20 atoms, C$_8$-C$_{20}$ arylcycloalkyl, C$_8$-C$_{20}$ arylcycloalkenyl, arylheterocyclyl including 8-20 atoms, or arylheterocycloalkenyl including 8-20 atoms, each of which is optionally substituted with from 1-10 R$^t$; or (viii) C$_6$-C$_{16}$ aryl or heteroaryl including 5-16 atoms, each of which is optionally substituted with from 1-10 R$^g$; and the other three are each hydrogen.

R$^{3a}$ can be: (i) halo; NR$^m$R$^n$; nitro; azido, hydroxy; C$_1$-C$_{12}$ alkoxy, optionally substituted with 1-5 R$^r$; C$_1$-C$_{12}$ haloalkoxy; C$_6$-C$_{16}$ aryloxy, optionally substituted with 1-5 R$^g$; C$_2$-C$_{12}$ alkenyloxy or C$_2$-C$_{12}$ alkynyloxy, each of which is optionally substituted with 1-5 R$^s$; C$_3$-C$_{16}$ cycloalkyloxy or C$_3$-C$_{16}$ halocycloalkyloxy, each of which is optionally substituted with 1-5 R$^h$; heterocyclyloxy including 3-16 atoms, optionally substituted with 1-5 R$^i$; C$_7$-C$_{20}$ aralkoxy, optionally substituted with 1-5 R$^t$; mercapto; C$_1$-C$_6$ thioalkoxy; C$_6$-C$_{16}$ thioaryloxy; cyano; formyl; —C(O)R$^j$, C$_1$-C$_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; —NR$^k$C(O)NR$^m$R$^n$; —NR$^k$C(O)OR$^j$; —S(O)$_n$R$^u$; —NR$^k$S(O)$_n$R$^j$; or —P(O)(OR$^m$)(OR$^n$); or (ii) C$_1$-C$_{20}$ alkyl, optionally substituted with from 1-10 R$^r$ and/or optionally inserted with from 1-10 heteroatoms selected from the group consisting of nitrogen, oxygen or sulfur; or (iii) C$_1$-C$_{20}$ haloalkyl, optionally substituted with from 1-10 R$^r$; or (iv) C$_3$-C$_{20}$ cycloalkyl or C$_3$-C$_{20}$ halocycloalkyl, optionally substituted with from 1-10 R$^h$; or (v) C$_3$-C$_{20}$ cycloalkenyl, heterocyclyl including 3-20 atoms, or heterocycloalkenyl including 3-20 atoms, each of which is optionally substituted with from 1-10 R$^i$; or (vi) C$_2$-C$_{20}$ alkenyl or C$_2$-C$_{20}$ alkynyl, each of which is optionally substituted with from 1-10 R$^s$; (vii) C$_7$-C$_{20}$ aralkyl, heteroaralkyl including 6-20 atoms, C$_8$-C$_{20}$ arylcycloalkyl, C$_8$-C$_{20}$ arylcycloalkenyl, arylheterocyclyl including 8-20 atoms, or arylheterocycloalkenyl including 8-20 atoms, each of which is optionally substituted with from 1-10 R$^t$; or (viii) C$_6$-C$_{16}$ aryl or heteroaryl including 5-16 atoms, each of which is optionally substituted with from 1-10 R$^g$; and R$^{3b}$, R$^{3c}$, and R$^{3d}$ each are hydrogen. For example, R$^{3a}$ can be halo, C$_1$-C$_6$ alkyl, C$_1$-C$_6$ alkoxy, —NR$^k$C(O)OR$^j$, —NR$^k$C(O)NR$^m$R$^n$, —NR$^k$C(O)R$^j$, or —NR$^m$R$^n$, and R$^{3b}$, R$^{3c}$, and R$^{3d}$ can each be hydrogen.

R$^{3b}$ can be: (i) halo; NR$^m$R$^n$; nitro; azido, hydroxy; C$_1$-C$_{12}$ alkoxy, optionally substituted with 1-5 R$^r$; C$_1$-C$_{12}$ haloalkoxy; C$_6$-C$_{16}$ aryloxy, optionally substituted with 1-5 R$^g$; C$_2$-C$_{12}$ alkenyloxy or C$_2$-C$_{12}$ alkynyloxy, each of which is optionally substituted with 1-5 R$^s$; C$_3$-C$_{16}$ cycloalkyloxy or C$_3$-C$_{16}$ halocycloalkyloxy, each of which is optionally substituted with 1-5 R$^h$; heterocyclyloxy including 3-16 atoms, optionally substituted with 1-5 R$^i$; C$_7$-C$_{20}$ aralkoxy, optionally substituted with 1-5 R$^t$; mercapto; C$_1$-C$_6$ thioalkoxy; C$_6$-C$_{16}$ thioaryloxy; cyano; formyl; —C(O)R$^j$, C$_1$-C$_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; —NR$^k$C(O)NR$^m$R$^n$; —NR$^k$C(O)OR$^j$; —S(O)$_n$R$^u$; —NR$^k$S(O)$_n$R$^j$; or —P(O)(OR$^m$)(OR$^n$); or (ii) C$_1$-C$_{20}$ alkyl, optionally substituted with from 1-10 R$^r$ and/or optionally inserted with from 1-10 heteroatoms selected from the group consisting of nitrogen, oxygen or sulfur; or (iii) C$_1$-C$_{20}$ haloalkyl, optionally substituted with from 1-10 R$^r$; or (iv) C$_3$-C$_{20}$ cycloalkyl or C$_3$-C$_{20}$ halocycloalkyl, optionally substituted with from 1-10 R$^h$; or (v) C$_3$-C$_{20}$ cycloalkenyl, heterocyclyl including 3-20 atoms, or heterocycloalkenyl including 3-20 atoms, each of which is optionally substituted with from 1-10 R$^i$; or (vi) C$_2$-C$_{20}$ alkenyl or C$_2$-C$_{20}$ alkynyl, each of which is optionally substituted with from 1-10 R$^s$; (vii) C$_7$-C$_{20}$ aralkyl, heteroaralkyl including 6-20 atoms, C$_8$-C$_{20}$ arylcycloalkyl, C$_8$-C$_{20}$ arylcycloalkenyl, arylheterocyclyl including 8-20 atoms, or arylheterocycloalkenyl including 8-20 atoms, each of which is optionally substituted with from 1-10 R$^t$; or (viii) C$_6$-C$_{16}$ aryl or heteroaryl including 5-16 atoms, each of which is optionally substituted with from 1-10 R$^g$; and R$^{3a}$, R$^{3c}$, and R$^{3d}$ each are hydrogen. For example, R$^{3b}$ can be halo, C$_1$-C$_6$ alkyl, C$_1$-C$_6$ alkoxy, C$_3$-C$_{10}$ cycloalkyl, C$_7$-C$_{10}$ aralkyl, —C(O)OR$^j$, —C(O)NR$^m$R$^n$, —NR$^k$C(O)OR$^j$, —NR$^k$C(O)NR$^m$R$^n$, —NR$^k$C(O)R$^j$, or —NR$^m$R$^n$, and R$^{3a}$, R$^{3c}$, and R$^{3d}$ can each be hydrogen.

R$^{3c}$ can be: (i) halo; NR$^m$R$^n$; nitro; azido, hydroxy; C$_1$-C$_{12}$ alkoxy, optionally substituted with 1-5 R$^r$; C$_1$-C$_{12}$ haloalkoxy; C$_6$-C$_{16}$ aryloxy, optionally substituted with 1-5 R$^g$; C$_2$-C$_{12}$ alkenyloxy or C$_2$-C$_{12}$ alkynyloxy, each of which is optionally substituted with 1-5 R$^s$; C$_3$-C$_{16}$ cycloalkyloxy or C$_3$-C$_{16}$ halocycloalkyloxy, each of which is optionally substituted with 1-5 R$^h$; heterocyclyloxy including 3-16 atoms, optionally substituted with 1-5 R$^i$; C$_7$-C$_{20}$ aralkoxy, optionally substituted with 1-5 R$^t$; mercapto; C$_1$-C$_6$ thioalkoxy; C$_6$-C$_{16}$ thioaryloxy; cyano; formyl; —C(O)R$^j$, C$_1$-C$_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; NR$^k$C(O)NR$^m$R$^n$; —NR$^k$C(O)OR$^j$; —S(O)$_n$R$^u$; —NR$^k$S(O)$_n$R$^j$; or —P(O)(OR$^m$)(OR$^n$); or (ii) C$_1$-C$_{20}$ alkyl, optionally substituted with from 1-10 R$^r$ and/or optionally inserted with from 1-10 heteroatoms selected from the group consisting of nitrogen, oxygen or sulfur; or (iii) C$_1$-C$_{20}$ haloalkyl, optionally substituted with from 1-10 R$^r$; or (iv) C$_3$-C$_{20}$ cycloalkyl or C$_3$-C$_{20}$ halocycloalkyl, optionally substituted with from 1-10 R$^h$; or (v) C$_3$-C$_{20}$ cycloalkenyl, heterocyclyl including 3-20 atoms, or heterocycloalkenyl including 3-20 atoms, each of which is optionally substituted with from 1-10 R$^i$; or (vi) C$_2$-C$_{20}$ alkenyl or C$_2$-C$_{20}$ alkynyl, each of which is optionally substituted with from 1-10 R$^s$; (vii) C$_7$-C$_{20}$ aralkyl, heteroaralkyl including 6-20 atoms, C$_8$-C$_{20}$ arylcycloalkyl, C$_8$-C$_{20}$ arylcycloalkenyl, arylheterocyclyl including 8-20 atoms, or arylheterocycloalkenyl including 8-20 atoms, each of which is optionally substituted with from 1-10 R$^t$; or (viii) C$_6$-C$_{16}$ aryl or heteroaryl including 5-16 atoms, each of which is optionally substituted with from 1-10 R$^g$; and R$^{3a}$, R$^{3b}$, and R$^{3d}$ each are hydrogen.

Two of R$^{3a}$, R$^{3b}$, R$^{3c}$, and R$^{3d}$ can be: (i) halo; NR$^m$R$^n$; nitro; azido, hydroxy; C$_1$-C$_{12}$ alkoxy, optionally substituted with 1-5 R$^r$; C$_1$-C$_2$ haloalkoxy; C$_6$-C$_{16}$ aryloxy, optionally substituted with 1-5 R$^g$; C$_2$-C$_{12}$ alkenyloxy or C$_2$-C$_{12}$ alkynyloxy, each of which is optionally substituted with 1-5 R$^s$; C$_3$-C$_{16}$ cycloalkyloxy or C$_3$-C$_{16}$ halocycloalkyloxy, each of which is optionally substituted with 1-5 R$^h$; heterocyclyloxy including 3-16 atoms, optionally substituted with 1-5 R$^i$; C$_7$-C$_{20}$ aralkoxy, optionally substituted with 1-5 R$^t$; mercapto; $C_1$-$C_6$ thioalkoxy; $C_6$-$C_{16}$ thioaryloxy; cyano; formyl; —C(O)R$^j$, $C_1$-$C_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^i$; —C(NR$^o$)R$^j$; —OC(O)NR$^m$R$^n$; —NR$^k$C(O)NR$^m$R$^n$; —NR$^k$C(O)OR$^j$; —S(O)$_n$R$^j$; —NR$^k$S(O)$_n$R$^j$; or —P(O)(OR$^m$)(OR$^n$); or (ii) $C_1$-$C_{20}$ alkyl, optionally substituted with from 1-10 R$^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 R$^r$; or (iv) $C_3$-$C_{20}$ cycloalkyl or $C_3$-$C_{20}$ halocycloalkyl, optionally substituted with from 1-10 R$^h$; or (v) $C_3$-$C_{20}$ cycloalkenyl, heterocyclyl including 3-20 atoms, or heterocycloalkenyl including 3-20 atoms, each of which is optionally substituted with from 1-10 R$^i$; or (vi) $C_2$-$C_{20}$ alkenyl or $C_2$-$C_{20}$ alkynyl, each of which is optionally substituted with from 1-10 RS; (vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 R$^t$; or (viii) $C_6$-$C_{16}$ aryl or heteroaryl including 5-16 atoms, each of which is optionally substituted with from 1-10 R$^g$; and the other two are each hydrogen.

$R^{3a}$ and $R^{3c}$, can each be independently: (i) halo; NR$^m$R$^n$; nitro; azido; hydroxy; $C_1$-$C_{12}$ alkoxy, optionally substituted with 1-5 R$^r$; $C_1$-$C_{12}$ haloalkoxy; $C_6$-$C_{16}$ aryloxy, optionally substituted with 1-5 R$^g$; $C_2$-$C_{12}$ alkenyloxy or $C_2$-$C_{12}$ alkynyloxy, each of which is optionally substituted with 1-5 R$^s$; $C_3$-$C_{16}$ cycloalkyloxy or $C_3$-$C_{16}$ halocycloalkyloxy, each of which is optionally substituted with 1-5 R$^h$; heterocyclyloxy including 3-16 atoms, optionally substituted with 1-5 R$^i$; $C_7$-$C_{20}$ aralkoxy, optionally substituted with 1-5 R$^t$; mercapto; $C_1$-$C_6$ thioalkoxy; $C_6$-$C_{16}$ thioaryloxy; cyano; formyl; —C(O)R$^j$, $C_1$-$C_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^i$; —C(NR$^o$)R$^j$; —OC(O)NR$^m$R$^n$; —NR$^k$C(O)NR$^m$R$^n$; —NR$^k$C(O)OR$^j$; —S(O)$_n$R$^u$; —NR$^k$S(O)$_n$R$^i$; or —P(O)(OR$^m$)(OR$^n$); or (ii) $C_1$-$C_{20}$ alkyl, optionally substituted with from 1-10 R$^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 R$^r$; or (iv) $C_3$-$C_{20}$ cycloalkyl or $C_3$-$C_{20}$ halocycloalkyl, optionally substituted with from 1-10 R$^h$; or (v) $C_3$-$C_{20}$ cycloalkenyl, heterocyclyl including 3-20 atoms, or heterocycloalkenyl including 3-20 atoms, each of which is optionally substituted with from 1-10 R$^i$; or (vi) $C_2$-$C_{20}$ alkenyl or $C_2$-$C_{20}$ alkynyl, each of which is optionally substituted with from 1-10 R$^s$; (vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 R$^t$; or (viii) $C_6$-$C_{16}$ aryl or heteroaryl including 5-16 atoms, each of which is optionally substituted with from 1-10 R$^g$; and $R^{3b}$ and $R^{3d}$ are each hydrogen.

The term "mammal" includes organisms, which include mice, rats, cows, sheep, pigs, rabbits, goats, and horses, monkeys, dogs, cats, and preferably humans.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/Kg to about 1000 mg/Kg, (e.g., from about 0.1 mg/Kg to about 100 mg/Kg, from about 1 mg/Kg to about 100 mg/Kg). Effective doses will also vary depending on route of administration, as well as the possibility of co-usage with other agents.

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{20}$ alkyl indicates that the group may have from 1 to 20 (inclusive) carbon atoms in it. Any atom can be substituted. Examples of alkyl groups include without limitation methyl, ethyl, and tert-butyl.

The term "cycloalkyl" refers to saturated monocyclic, bicyclic, tricyclic, or other polycyclic hydrocarbon groups. Any atom can be substituted, e.g., by one or more substituents. Cycloalkyl groups can contain fused rings. Fused rings are rings that share a common carbon atom. Cycloalkyl moieties can include, e.g., cyclopropyl, cyclohexyl, methylcyclohexyl adamantyl, and norbornyl. A ring carbon can optionally be the point of attachment to another moiety (e.g., for methylcyclohexyl and the like, the point of attachment can be either the methyl group or a cyclohexyl ring carbon).

The terms "haloalkyl" and "halocycloalkyl" refer to an alkyl or cycloalkyl group, respectively, in which at least one hydrogen atom is replaced by halo. In some embodiments, more than one hydrogen atom (2, 3, 4, 5, 6, 7, 8, 9, 10, 11, 12, 13, 14, 15, 16, 17, 18, 19, 20, 21, 22, 23, 24, 25, 26, etc. hydrogen atoms) on a alkyl or cycloalkyl group can be replaced by more than one halogens (e.g., 2, 3, 4, 5, 6, 7, 8, 9, 10, 11, 12, 13, 14, 15, 16, 17, 18, 19, 20, 21, 22, 23, 24, 25, 26, etc. hydrogen atoms), which can be the same or different. "Haloalkyl" and "halocycloalkyl" also include alkyl moieties in which all hydrogens have been replaced by halo (e.g., perhaloalkyl and perhalocycloalkyl, such as trifluoromethyl and perfluorocyclohexyl, respectively).

The term "aralkyl" refers to an alkyl moiety in which an alkyl hydrogen atom is replaced by an aryl group. Aralkyl includes groups in which more than one hydrogen atom on an alkyl moiety has been replaced by an aryl group. Any ring or chain atom can be substituted e.g., by one or more substituents. Examples of "aralkyl" include without limitation benzyl, 2-phenylethyl, 3-phenylpropyl, benzhydryl, and trityl groups.

The term "heteroaralkyl" refers to an alkyl moiety in which an alkyl hydrogen atom is replaced by a heteroaryl group. Heteroaralkyl includes groups in which more than one hydrogen atom on an alkyl moiety has been replaced by a heteroaryl group. Any ring or chain atom can be substituted e.g., by one or more substituents. Heteroaralkyl can include, for example, 2-pyridylethyl.

The term "alkenyl" refers to a straight or branched hydrocarbon chain containing 2-20 carbon atoms and having one or more double bonds. Any atom can be substituted, e.g., by one or more substituents. Alkenyl groups can include, e.g., allyl, propenyl, 2-butenyl, 3-hexenyl and 3-octenyl groups. One of the double bond carbons can optionally be the point of attachment of the alkenyl substituent. The term "alkynyl" refers to a straight or branched hydrocarbon chain containing 2-20 carbon atoms and having one or more triple bonds. Any atom can be substituted, e.g., by one or more substituents. Alkynyl groups can include, e.g., ethynyl, propargyl, and 3-hexynyl. One of the triple bond carbons can optionally be the point of attachment of the alkynyl substituent.

Alkylene, alkenylene, and alkynylene refer to divalent alkyl, alkenyl, and alkynyl moieties, respectively (e.g., —$CH_2$—, —CH=CH—, and —C≡C—, respectively). Any atom can be substituted.

The term "alkoxy" refers to an —O-alkyl radical. The term "mercapto" refers to an SH radical. The term "thioalkoxy" refers to an —S-alkyl radical. The term aryloxy refers to an —O-aryl radical. The term thioaryloxy refers to an —S-aryl radical.

The term "aryl" refers to an aromatic monocyclic, bicyclic, or tricyclic hydrocarbon ring system, wherein any ring atom can be substituted, e.g., by one or more substituents. Aryl groups can contain fused rings. Fused rings are rings that share a common carbon atom. Aryl moieties can include, e.g., phenyl, naphthyl, anthracenyl, and pyrenyl.

The term "heterocyclyl" refers to a monocyclic, bicyclic, tricyclic or other polycyclic ring system having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). The heteroatom or ring carbon can optionally be the point of attachment of the heterocyclyl substituent to another moiety (e.g., for 4-methylpiperidinyl or 1-methylpiperidinyl, the point of attachment can be either the methyl group or a ring atom, e.g., carbon or nitrogen). Any atom can be substituted, e.g., by one or more substituents. The heterocyclyl groups can contain fused rings. Fused rings are rings that share a common carbon atom. Heterocyclyl groups can include, e.g., tetrahydrofuranyl, tetrahydropyranyl, piperidinyl, morpholino, pyrrolinyl, and pyrrolidinyl.

The term "cycloalkenyl" refers to partially unsaturated monocyclic, bicyclic, tricyclic, or other polycyclic hydrocarbon groups. A ring carbon (e.g., saturated or unsaturated) can optionally be the point of attachment of the cycloalkenyl substituent (e.g., for methylcyclohexenyl and the like, the point of attachment can be either the methyl group or a cyclohexenyl ring carbon). Any atom can be substituted e.g., by one or more substituents. The cycloalkenyl groups can contain fused rings. Fused rings are rings that share a common carbon atom. Cycloalkenyl moieties can include, e.g., cyclohexenyl, cyclohexadienyl, norbornenyl, or cyclooctatetraenyl.

The term "heterocycloalkenyl" refers to partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). A ring carbon (e.g., saturated or unsaturated) or heteroatom can optionally be the point of attachment of the heterocycloalkenyl substituent (e.g., for methyldihydropyranyl and the like, the point of attachment can be either the methyl group or a ring carbon). Any atom can be substituted, e.g., by one or more substituents. The heterocycloalkenyl groups can contain fused rings. Fused rings are rings that share a common carbon atom. Heterocycloalkenyl groups can include, e.g., tetrahydropyridyl, and dihydropyranyl.

The term "heteroaryl" refers to an aromatic monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). Any atom can be substituted, e.g., by one or more substituents. Heteroaryl groups can contain fused rings. Fused rings are rings that share a common carbon atom. Heteroaryl groups include pyridyl, thienyl, furanyl, imidazolyl, and pyrrolyl.

The terms "arylcycloalkyl," "arylcycloalkenyl," "arylheterocyclyl," and "arylheterocycloalkenyl" refer to bicyclic, tricyclic, or other polycyclic ring systems that include an aryl ring fused to a cycloalkyl, cycloalkenyl, heterocyclyl, and heterocycloalkenyl, respectively. Any atom can be substituted, e.g., by one or more substituents. For example, arylcycloalkyl can include fluorenyl and indanyl; arylcycloalkenyl can include indenyl; arylheterocyclyl can include 2,3-dihydrobenzofuranyl and 1,2,3,4-tetrahydroisoquinolinyl; and arylheterocycloalkenyl can include 1,4-dihydro-1,4-epoxynaphthalenyl.

The term "oxo" refers to an oxygen atom, which forms a carbonyl (C=O) when attached to carbon, an N-oxide when attached to nitrogen, and a sulfoxide or sulfone when attached to sulfur. The term "thioxo" refers to an oxygen atom, which forms a thiocarbonyl (C=S) when attached to carbon.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, or heteroaryl group at any atom of that group. In one aspect, the substituents (e.g., $R^3$) on a group are independently any one single, or any combination of two or more of the permissible atoms or groups of atoms delineated for that substituent. In another aspect, a substituent may itself be substituted with any one of the above substituents (e.g., $R^g$).

In some embodiments, the compounds have a reduced likelihood (e.g., relative to PPAR-γ agonist diabetes drugs) of producing weight gain associated side effects when administered to a subject, e.g., a subject in need of treatment of type 2 diabetes.

The details of one or more embodiments of the invention are set forth in the accompanying drawings and the description below. Other features and advantages of the invention will be apparent from the description and from the claims.

DETAILED DESCRIPTION

This invention relates to cyclic PTP1b inhibitor compounds, pharmaceutical compositions and related methods.

The cyclic PTP1b inhibitor compounds have the general formula (I) below:

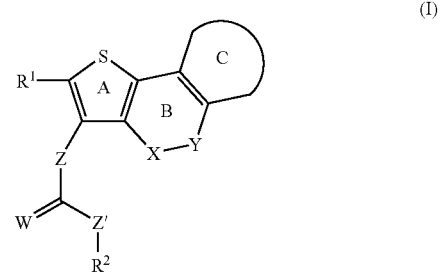

In some embodiments, X can be $C(R^a)(R^b)$, $NR^c$, or S.

In some embodiments, $R^a$ and $R^b$ can be, independently of one another, hydrogen or $C_1$-$C_{10}$ (e.g., $C_1$, $C_2$, $C_3$, $C_4$, $C_5$, $C_6$, $C_7$, $C_8$, $C_9$, or $C_{10}$) alkyl. In certain embodiments, $R^a$ and $R^b$ can be the same (e.g., both are hydrogen or both can be $C_1$-$C_{10}$ alkyl, e.g., $CH_3$) or different (e.g., one of $R^a$ and $R^b$ can be hydrogen and the other can be $C_1$-$C_{10}$ alkyl; or $R^a$ and $R^b$ can both be $C_1$-$C_{10}$ alkyl with each of $R^a$ and $R^b$ having a different carbon content, e.g., $R^a$ can be $C_2$ alkyl and $R^b$ can be $C_3$ alkyl).

In certain embodiments, one of $R^a$ and $R^b$ can be hydrogen or $C_1$-$C_{10}$ (e.g., $C_1$, $C_2$, $C_3$, $C_4$, $C_5$, $C_6$, $C_7$, $C_8$, $C_9$, or $C_{10}$) alkyl, and the other together with $R^d$, $R^e$, or $R^f$ can be a bond (e.g., a bond that is part of a double bond between the atoms to which $R^a$ and $R^b$ and $R^d$, $R^e$, and $R^f$ are attached).

In some embodiments, $R^c$ can be hydrogen or $C_1$-$C_6$ (e.g., $C_1$, $C_2$, $C_3$, $C_4$, $C_5$, or $C_6$) alkyl. In certain embodiments, $R^c$ together with $R^d$ or $R^e$ can be a bond (e.g., a bond that is part of a double bond between the atoms to which $R^c$ and $R^d$ and $R^e$ are attached).

In some embodiments, Y can be $C(R^d)(R^e)$, $NR^f$, or a bond.

In some embodiments, $R^d$ and $R^e$ can be, independently of one another, hydrogen or $C_1$-$C_{10}$ (e.g., $C_1$, $C_2$, $C_3$, $C_4$, $C_5$, $C_6$, $C_7$, $C_8$, $C_9$, or $C_{10}$) alkyl. In certain embodiments, $R^c$ and $R^d$ can be the same (e.g., both are hydrogen or both can be $C_1$-$C_{10}$ alkyl, e.g., $CH_3$) or different (e.g., one of $R^c$ and $R^d$ can be hydrogen and the other can be $C_1$-$C_{10}$ alkyl; or $R^c$ and $R^d$ can both be $C_1$-$C_{10}$ alkyl with each of $R^c$ and $R^d$ having a different carbon content, e.g., $R^c$ can be $C_2$ alkyl and $R^d$ can be $C_3$ alkyl).

In certain embodiments, one of $R^d$ and $R^e$ can be hydrogen or $C_1$-$C_{10}$ (e.g., $C_1$, $C_2$, $C_3$, $C_4$, $C_5$, $C_6$, $C_7$, $C_8$, $C_9$, or $C_{10}$) alkyl, and the other together with $R^a$, $R^b$, or $R^c$ can be a bond (e.g., a bond that is part of a double bond between the atoms to which $R^d$ and $R^e$ and $R^a$, $R^b$, and $R^c$ are attached).

In some embodiments, $R^f$ can be hydrogen or $C_1$-$C_6$ (e.g., $C_1$, $C_2$, $C_3$, $C_4$, $C_5$, or $C_6$) alkyl. In certain embodiments, $R^f$ together with $R^a$ or $R^b$ can be a bond (e.g., a bond that is part of a double bond between the atoms to which $R^f$ and $R^a$ and $R^b$ are attached).

In some embodiments, $R^1$ can be $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which can be optionally substituted with from 1-10 (e.g., 1, 2, 3, 4, 5, 6, 7, 8, 9, or 10) $R^g$.

In some embodiments, $R^1$ can be $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyl or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyl, each of which can be optionally substituted with from 1-5 (e.g., 1, 2, 3, 4, 5)$R^h$.

In some embodiments, $R^1$ can be $C_3$-$C_{10}$ (e.g., $C_3$, $C_4$, $C_5$, $C_6$, $C_7$, $C_8$, $C_9$, or $C_{10}$) cycloalkenyl, heterocyclyl including 5-10 (e.g., 5, 6, 7, 8, 9, 10) atoms, or heterocycloalkenyl including 5-10 (e.g., 5, 6, 7, 8, 9, 10) atoms, each of which can be optionally substituted with from 1-5 $R^i$.

In some embodiments, $R^1$ can be cyano, —C(O)$R^j$, —C(O)O$R^j$, —OC(O)$R^j$, —C(O)S$R^j$, —SC(O)$R^j$, —C(S)S$R^j$, —SC(S)$R^j$, —NR$^k$C(O)$R^j$, —C(O)NR$^m$R$^n$; or —C(NR$^o$)$R^j$.

In some embodiments, W can be O. In other embodiments, W can be S.

Each Z and Z' can be, independently of one another:

(i) O, $NR^p$, S, SO, or $SO_2$; or (ii) $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkylene; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenylene; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynylene; O($C_1$-$C_{12}$ alkylene) (e.g., $C_1$, $C_2$, $C_3$, $C_4$, $C_5$, $C_6$, $C_7$, $C_8$, $C_9$, $C_{10}$, $C_{11}$, or $C_{12}$); O($C_2$-$C_{12}$ alkenylene) (e.g., $C_2$, $C_3$, $C_4$, $C_5$, $C_6$, $C_7$, $C_8$, $C_9$, $C_{10}$, $C_{11}$, or $C_{12}$); O($C_2$-$C_{12}$ alkynylene) (e.g., $C_2$, $C_3$, $C_4$, $C_5$, $C_6$, $C_7$, $C_8$, $C_9$, $C_{10}$, $C_{11}$, or $C_{12}$); $NR^p$($C_1$-$C_{12}$ alkylene) (e.g., $C_1$, $C_2$, $C_3$, $C_4$, $C_5$, $C_6$, $C_7$, $C_8$, $C_9$, $C_{10}$, $C_{11}$, or $C_{12}$); $NR^p$($C_2$-$C_{12}$ alkenylene) (e.g., $C_2$, $C_3$, $C_4$, $C_5$, $C_6$, $C_7$, $C_8$, $C_9$, $C_{10}$, $C_{11}$, or $C_{12}$); $NR^p$($C_2$-$C_{12}$ alkynylene) (e.g., $C_2$, $C_3$, $C_4$, $C_5$, $C_6$, $C_7$, $C_8$, $C_9$, $C_{10}$, $C_{11}$, or $C_{12}$); S($C_1$-$C_{12}$ alkylene) (e.g., $C_1$, $C_2$, $C_3$, $C_4$, $C_5$, $C_6$, $C_7$, $C_8$, $C_9$, $C_{10}$, $C_{11}$, or $C_{12}$); S($C_2$-$C_{12}$ alkenylene) (e.g., $C_2$, $C_3$, $C_4$, $C_5$, $C_6$, $C_7$, $C_8$, $C_9$, $C_{10}$, $C_{11}$, or $C_{12}$); S($C_2$-$C_{12}$ alkynylene) (e.g., $C_2$, $C_3$, $C_4$, $C_5$, $C_6$, $C_7$, $C_8$, $C_9$, $C_{10}$, $C_{11}$, or $C_{12}$); SO($C_1$-$C_{12}$ alkylene) (e.g., $C_1$, $C_2$, $C_3$, $C_4$, $C_5$, $C_6$, $C_7$, $C_8$, $C_9$, $C_{10}$, $C_{11}$, or $C_{12}$); SO($C_2$-$C_{12}$ alkenylene) (e.g., $C_2$, $C_3$, $C_4$, $C_5$, $C_6$, $C_7$, $C_8$, $C_9$, $C_{10}$, $C_{11}$, or $C_{12}$); SO($C_2$-$C_{12}$ alkynylene) (e.g., $C_2$, $C_3$, $C_4$, $C_5$, $C_6$, $C_7$, $C_8$, $C_9$, $C_{10}$, $C_{11}$, or $C_{12}$); $SO_2$($C_1$-$C_{12}$ alkylene) (e.g., $C_1$, $C_2$, $C_3$, $C_4$, $C_5$, $C_6$, $C_7$, $C_8$, $C_9$, $C_{10}$, $C_{11}$, or $C_{12}$); $SO_2$($C_2$-$C_{12}$ alkenylene) (e.g., $C_2$, $C_3$, $C_4$, $C_5$, $C_6$, $C_7$, $C_8$, $C_9$, $C_{10}$, $C_{11}$, or $C_{12}$); or $SO_2$($C_2$-$C_{12}$ alkynylene) (e.g., $C_2$, $C_3$, $C_4$, $C_5$, $C_6$, $C_7$, $C_8$, $C_9$, $C_{10}$, $C_{11}$, or $C_{12}$); each of which can be optionally substituted with 1-5 (e.g., 1, 2, 3, 4, or 5) $R^q$. In certain embodiments, the heteroatom or heteroatom group (e.g., the oxygen in O($C_1$-$C_{12}$ alkylene) or the $SO_2$ group in $SO_2$($C_1$-$C_{12}$ alkylene)), when present, can be attached to ring A. In other embodiments, the heteroatom or heteroatom group, when present, is attached to the carbon connected to W and Z'.

In certain embodiments, Z and Z' can be the same (e.g., both can be O or both can be O($C_1$-$C_{12}$ alkylene), e.g., $OCH_2$) or different (e.g., one of Z and Z' can be O and the other can be S; one of Z and Z' can be O and the other can be O($C_1$-$C_{12}$ alkylene), e.g., $OCH_2$; one of Z and Z' can be SO($C_2$-$C_{12}$ alkynylene) and the other can be O($C_1$-$C_{12}$ alkylene); or Z and Z' can both be O($C_1$-$C_{12}$ alkylene) with each of Z and Z' having a different carbon content, e.g., Z can be $OCH_2$ and Z' can be $OCH_2CH_2$).

In some embodiments, $R^2$ can be hydrogen.

In some embodiments, $R^2$ can be $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkyl, optionally substituted with from 1-10 (e.g., 1, 2, 3, 4, 5, 6, 7, 8, 9, or 10) $R^r$ and/or optionally inserted with from 1-10 (e.g., 1, 2, 3, 4, 5, 6, 7, 8, 9, or 10) heteroatoms selected from the group consisting of nitrogen, oxygen or sulfur.

In some embodiments, $R^2$ can be $C_1$-$C_{20}$ (e.g., CI, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, optionally substituted with from 1-10 (e.g., 1, 2, 3, 4, 5, 6, 7, 8, 9, or 10) $R^r$.

In some embodiments, $R^2$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^h$.

In some embodiments, $R^2$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10)$R^i$.

In some embodiments, $R^2$ can be $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^s$.

In some embodiments, $R^2$ can be $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, $C_8$-$C_{20}$ (e.g., Cs, Cs, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) arylcycloalkyl, $C_8$-$C_{20}$ (e.g., $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) arylcycloalkenyl, arylheterocyclyl including 8-20 (e.g., 8, 9, 10, 11, 12, 13, 14, 15, 16, 17, 18, 19, or 20) atoms, or arylheterocycloalkenyl including 8-20 (e.g., 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^t$.

In some embodiments, $R^2$ can be $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$.

In some embodiments, ring C can represent a fused $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or a fused heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^3$.

In some embodiments, ring C can represent a fused $C_3$-$C_{10}$ (e.g., $C_3$, $C_4$, $C_5$, $C_6$, $C_7$, $C_8$, $C_9$, or $C_{10}$) cycloalkyl, a fused $C_3$-$C_{10}$ (e.g., $C_3$, $C_4$, $C_5$, $C_6$, $C_7$, $C_8$, $C_9$, or $C_{10}$) cycloalkenyl, a fused heterocyclyl including 5-10 (e.g., 5, 6, 7, 8, 9, or 10) atoms, or a fused heterocycloalkenyl including 5-10 (e.g., 5, 6, 7, 8, 9, or 10) atoms, each of which is optionally substituted with from 1-5 (e.g., 1, 2, 3, 4, or 5) $R^4$.

In all embodiments, the two carbons atoms that are shared between rings B and C in formula (I) (see, e.g., $C^1$ and $C^2$ in formulas (I-a), (I-b), and (I-c) below) are included in the total carbon/atom count for ring C. The degree of unsaturation present in the unshared ring atoms of fused ring C (see, e.g., $C^3$, $C^4$, $C^5$, or $C^6$ in formulas (I-a), (I-b), and (I-c) below) is determinative as to whether ring C is a fused aryl, heteroaryl, cycloalkyl, cycloalkenyl, heterocyclyl, or heterocycloalkenyl. By way of example, formula (I-a), (I-b), and (I-c) correspond to examples of formula (I) compounds in which ring C is a fused $C_6$ aryl, a fused $C_6$ cycloalkenyl, and a fused $C_6$ cycloalkyl, respectively. The same formulas can apply when fused ring C is one of the heterocyclic counterparts (i.e., a fused heteroaryl, heterocycloalkenyl, or heterocyclyl, each having 6 atoms) except that one or more of (e.g., 1, 2, or 3 of) $C^3$, $C^4$, $C^5$, or $C^6$ would be replaced by one of more heteroatoms (e.g., nitrogen, oxygen, or sulfur, or any combination thereof when two or more heteroatoms are present). Formulae (I-a), (I-b), and (I-c) are intended to be illustrative and are not to be construed as limiting in any way (e.g., the above-mentioned heteroatom content can apply to any heteroaryl including 5-16 atoms, heterocyclyl including 5-10 atoms, or heterocycloalkenyl including 5-10 atoms).

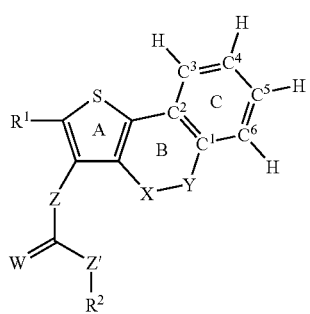

I-a

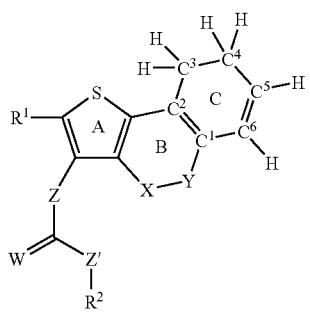

I-b

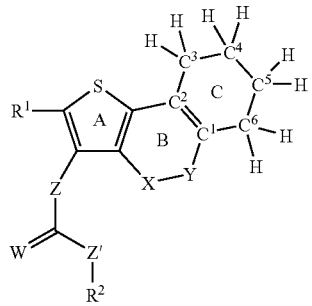

I-c

Each $R^3$ can be, independently of one another:

(i) halo; $NR^mR^n$; nitro; azido, hydroxy; $OR^m$ (e.g., $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$); mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ (e.g., $C_1$, $C_2$, or $C_3$) alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —N$R^k$C(O)$R^j$; —C(N$R^o$)$R^j$; —OC(O)N$R^mR^n$; N$R^k$C(O)N$R^mR^n$; —N$R^k$C(O)O$R^j$; —S(O)$_n$$R^u$; —N$R^k$S(O)$_n$$R^j$; or —P(O)(O$R^m$)(O$R^n$); or (ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkyl, optionally substituted with from 1-10 (e.g., 1, 2, 3, 4, 5, 6, 7, 8, 9, or 10) $R^r$ and/or optionally inserted with from 1-10 (e.g., 1, 2, 3, 4, 5, 6, 7, 8, 9, or 10) heteroatoms selected from the group consisting of nitrogen, oxygen or sulfur; or (iii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, optionally substituted with from 1-10 (e.g., 1, 2, 3, 4, 5, 6, 7, 8, 9, or 10) $R^r$; or (iV) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_18$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10)$R^h$; or (v) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^i$; or (vi) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^s$;

(vii) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, $C_8$-$C_{20}$ (e.g., $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) arylcycloalkyl, $C_8$-$C_{20}$ (e.g., $C_8$, $C_9$, $C_{10}$, $C_{11}$, $C_{12}$7$C_{13}$3$C_{14}$, $C_{15}$, $C_{16}$, $C_{17}$, $C_{18}$, $C_{19}$, or $C_{20}$) arylcycloalkenyl, arylheterocyclyl including 8-20 (e.g., 8, 9, 10, 11, 12, 13, 14, 15, 16, 17, 18, 19, or 20) atoms, or arylheterocycloalkenyl including 8-20 (e.g., 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10)$R^t$; or (viii) $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$.

Each $R^4$ can be, independently of one another:

(i) halo; $NR^mR^n$; nitro; azido, hydroxy; oxo; thioxo; =$NR^o$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^t$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ (e.g., $C_1$, $C_2$, or $C_3$) alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)ORI; —S(O)$_n$$R^u$; —$NR^k$S(O)$_n$$R^j$; or —P(O)(O$R^m$)(O$R^n$); or (ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkyl, optionally substituted with from 1-10 (e.g., 1, 2, 3, 4, 5, 6, 7, 8, 9, or 10) $R^r$ and/or optionally inserted with from 1-10 (e.g., 1, 2, 3, 4, 5, 6, 7, 8, 9, or 10) heteroatoms selected from the group consisting of nitrogen, oxygen or sulfur; or (iii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, optionally substituted with from 1-10 (e.g., 1, 2, 3, 4, 5, 6, 7, 8, 9, or 10)$R^r$; or (iv) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^h$; or (v) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^i$; or (vi) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^s$;

(vii) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, $C_8$-$C_{20}$ (e.g., $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) arylcycloalkyl, $C_8$-$C_{20}$ (e.g., $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) arylcycloalkenyl, arylheterocyclyl including 8-20 (e.g., 8, 9, 10, 11, 12, 13, 14, 15, 16, 17, 18, 19, or 20) atoms, or arylheterocycloalkenyl including 8-20 (e.g., 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10)$R^t$; or (viii) $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$.

Each $R^g$ can be, independently of one another:

(i) halo; $NR^mR^n$; nitro; azido, hydroxy; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$ or $R^{g'}$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^t$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$); or (ii) $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkyl, optionally substituted with from 1-10 (e.g., 1, 2, 3, 4, 5, 6, 7, 8, 9, or 10) $R^r$ and/or optionally inserted with from 1-6 (e.g., 1, 2, 3, 4, 5, or 6) heteroatoms selected from the group consisting of nitrogen, oxygen or sulfur; or (iii) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^h$; or (iv) $C_3$-$C_{20}$ (e.g., $C_3$, $C_4$, $C_5$, $C_6$, $C_7$, Cs, $C_9$, $C_{10}$, C $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) atoms, each of which is optionally substituted with from 1-10 (e.g., 1, 2, 3, 4, 5, 6, 7, 8, 9, or 10) $R^i$; or (v) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1,2,3,4,5,6,7,8,9, or 10) $R^s$; or (vi) $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkyl; or (vii) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^t$; or (viii) $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$ or $R^{g'}$.

Each $R^{g'}$ can be, independently of one another, $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkyl, $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkyl, $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyl; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyl; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, Cli, $C_{19}$, or $C_{20}$) halocycloalkyl; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) atoms, or heterocycloalkenyl including 3-20 (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms; halo; $NR'''R^n$; nitro; azido, hydroxy; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy; $C_2$-$C_{12}$ (e.g., $C_2$, $C_3$, $C_4$, $C_5$, $C_6$, $C_7$, $C_8$, $C_9$, $C_{10}$, C, or $C_{12}$) alkynyloxy; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy; heterocyclyloxy including 3-16 (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R'''R^n$; —N$R^k$C(O)$R^j$; —C(N$R^o$)$R^j$; —OC(O)N$R'''R^n$; N$R^k$C(O)N$R'''R^n$; —N$R^k$C(O)O$R^j$; —S(O)$_n$$R^u$; —N$R^k$S(O)$_n$$R^j$; or —P(O)(O$R^m$)(O$R^n$).

Each $R^h$ can be, independently of one another:

(i) N$R'''R^n$; nitro; azido, hydroxy; oxo; thioxo; =N$R^o$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R'''R^n$; —N$R^k$C(O)$R^j$; —C(N$R^o$)$R^j$; —OC(O)N$R'''R^n$; —N$R^k$C(O)N$R'''R^n$; —N$R^k$C(O)O$R^j$; —S(O)$_n$$R^u$; —N$R^k$S(O)$_n$$R^j$; or —P(O)(O$R^m$)(O$R^n$); or (ii) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^s$; or (iii) $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$.

Each $R^j$ can be, independently of one another:

(i) halo, N$R'''$RN; nitro; azido, hydroxy; oxo; thioxo; =N$R^o$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ alkylenedioxy; —C(O)O$R^j$;

—OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; —NR$^k$C(O)NR$^m$R$^n$; —NR$^k$C(O)OR$^j$; —S(O)$_n$R$^u$; —NR$^k$S(O)$_n$R$^j$; or —P(O)(OR$^m$)(OR$^n$); or (ii) C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkenyl or C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkynyl, each of which is optionally substituted with from 1-10 (e.g., 1, 2, 3, 4, 5, 6, 7, 8, 9, or 10) R$^s$; or (iii) C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^g$.

Each R$^j$, R$^k$, R$^m$, and R$^n$ can be, independently of one another:

(i) hydrogen; or (ii) C$_1$-C$_{20}$ (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkyl, optionally substituted with from 1-10 (e.g., 1, 2, 3, 4, 5, 6, 7, 8, 9, or 10) R$^r$ and/or optionally inserted with from 1-6 (e.g., 1, 2, 3, 4, 5, or 6) heteroatoms selected from the group consisting of nitrogen, oxygen or sulfur;

(iii) C$_1$-C$_{20}$ (e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) haloalkyl; or (iv) C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkenyl or C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkynyl, each of which is optionally substituted with from 1-10 (e.g., 1, 2, 3, 4, 5, 6, 7, 8, 9, or 10) R$^s$; or (v) C$_3$-C$_{20}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) cycloalkyl or C$_3$-C$_{20}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) halocycloalkyl, each of which is optionally substituted with from 1-10 (e.g., 1, 2, 3, 4, 5, 6, 7, 8, 9, or 10) R$^h$; or (vi) C$_3$-C$_{20}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) cycloalkenyl, heterocyclyl including 3-16 (e.g., 3, 4, 5, 6, 7, 8, 9, 10, 11, 12, 13, 14, 15, or 16) atoms, or heterocycloalkenyl including 3-16 (e.g., 3, 4, 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^t$; or (vii) C$_7$-C$_{20}$ (e.g., C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) aralkyl, heteroaralkyl including 6-20 (e.g., 6, 7, 8, 9, 10, 11, 12, 13, 14, 15, 16, 17, 18, 19, or 20) atoms, C$_8$-C$_{20}$ (e.g., C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) arylcycloalkyl, C$_8$-C$_{20}$ (e.g., Cg, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) arylcycloalkenyl, arylheterocyclyl including 8-20 (e.g., 8, 9, 10, 11, 12, 13, 14, 15, 16, 17, 18, 19, or 20) atoms, or arylheterocycloalkenyl including 8-20 (e.g., 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10)R$^t$; or (viii) C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^g$.

Each R$^o$ can be, independently of one another, hydrogen; C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) alkyl optionally inserted with from 1-6 (e.g., 1, 2, 3, 4, 5, or 6) heteroatoms selected from the group consisting of nitrogen, oxygen or sulfur; C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkenyl; C$_2$-C$_{20}$ (e.g., C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) alkynyl; C$_7$-C$_{20}$ (e.g., C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) aralkyl; heteroaralkyl including 6-20 (e.g., 6, 7, 8, 9, 10, 11, 12, 13, 14, 15, 16, 17, 18, 19, or 20) atoms; C$_3$-C$_{16}$ (e.g., C$_3$, C$_4$, C$_5$, C$_6$, C$_7$, C$_8$, C$_9$, C$_{10}$, Cli, C$_{12}$, C$_{13}$, C$_{14}$, C$_{15}$, or C$_{16}$) cycloalkyl; C$_3$-C$_{16}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, or C$_{16}$) cycloalkenyl; heterocyclyl including 3-16 (e.g., 3, 4, 5, 6, 7, 8, 9, 10, 11, 12, 13, 14, 15, or 16) atoms; heterocycloalkenyl including 3-16 (e.g., 3, 4, 5, 6, 7, 8, 9, 10, 11, 12, 13, 14, 15, or 16) atoms; C$_8$-C$_{20}$ (e.g., C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) arylcycloalkyl; C$_8$-C$_{20}$ (e.g., C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) arylcycloalkenyl; arylheterocyclyl including 8-20 (e.g., 8, 9, 10, 11, 12, 13, 14, 15, 16, 17, 18, 19, or 20) atoms; or arylheterocycloalkenyl including 8-20 (e.g., 8, 9, 10, 11, 12, 13, 14, 15, 16, 17, 18, 19, or 20) atoms; C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) aryl or heteroaryl including 5-16 (e.g., 5, 6, 7, 8, 9, 10, 11, 12, 13, 14, 15, or 16) atoms; NR$^m$R$^n$, or OR$^j$.

Each R$^p$ can be, independently of one another, hydrogen or C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) alkyl.

Each R$^q$ can be, independently of one another, halo, NR$^m$R$^n$; nitro; azido, hydroxy; oxo, thioxo, =NR$^o$, C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) alkoxy, optionally substituted with 1-5 (e.g., 1, 2, 3, 4, or 5) R$^r$; C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) haloalkoxy; C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) aryloxy, optionally substituted with 1-5 (e.g., 1, 2, 3, 4, or 5) R$^g$; C$_2$-C$_{12}$ (e.g., C$_2$, C$_3$, C$_4$, C$_5$, C$_6$, C$_7$, C$_8$, C$_9$, C$_{10}$, C$_{11}$, or C$_{12}$) alkenyloxy or C$_2$-C$_{12}$ (e.g., C$_2$, C$_3$, C$_4$, C$_5$, C$_6$, C$_7$, C$_8$, C$_9$, C$_{10}$, Ci , or C$_{12}$) alkynyloxy, each of which is optionally substituted with 1-5 (e.g., 1, 2, 3, 4, or 5) R$^s$; C$_3$-C$_{16}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, or C$_{16}$) cycloalkyloxy or C$_3$-C$_{16}$ (e.g., C$_3$, C$_4$, C$_5$, C$_6$, C$_7$, C$_8$, C$_9$, C$_{10}$, Cli, C$_{12}$, C$_{13}$, C$_{14}$, C$_{15}$, or C$_{16}$) halocycloalkyloxy, each of which is optionally substituted with 1-5 (e.g., 1, 2, 3, 4, or 5) R$^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) R$^t$; C$_7$-C$_{20}$ (e.g., C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, or C$_{20}$) aralkoxy, optionally substituted with 1-5 (e.g., 1, 2, 3, 4, or 5) R$^t$; mercapto; C$_1$-C$_6$ (e.g., C$_1$, C$_2$, C$_3$, C$_4$, C$_5$, or C$_6$) thioalkoxy; C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) thioaryloxy; cyano; formyl; —C(O)R$^j$, C$_1$-C$_3$ alkylenedioxy; —C(O)OR$^j$; —OC(O)R$^j$; —C(O)SR$^j$; —SC(O)R$^j$; —C(S)SR$^j$; —SC(S)R$^j$; —C(O)NR$^m$R$^n$; —NR$^k$C(O)R$^j$; —C(NR$^o$)R$^j$; —OC(O)NR$^m$R$^n$; —NR$^k$C(O)NR$^m$R$^n$; NR$^k$C(O)OR$^j$; —S(O)$_n$R$^u$; —NR$^k$S(O)$_n$R$^j$; or —P(O)(OR$^m$)(OR$^n$).

Each R$^r$ can be, independently of one another, NR$^m$R$^n$; nitro; azido, hydroxy; oxo; thioxo; =NR$^o$; C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) alkoxy, optionally substituted with 1-5 (e.g., 1, 2, 3, 4, or 5) R$^r$; C$_1$-C$_{12}$ (e.g., C$_1$, C$_2$, C$_3$, C$_4$, C$_5$, C$_6$, C$_7$, C$_8$, C$_9$, C$_{10}$, C$_{11}$, or C$_{12}$) haloalkoxy; C$_6$-C$_{16}$ (e.g., C$_6$, C$_7$, C$_8$, C$_9$, C$_{10}$, C$_{11}$, C$_{12}$, C$_{13}$, C$_{14}$, C$_{15}$, or C$_{16}$) aryloxy, optionally substituted with 1-5 (e.g., 1, 2, 3, 4, or 5) R$^g$; C$_2$-C$_{12}$ (e.g., C$_2$, C$_3$, C$_4$, C$_5$, C$_6$, C$_7$, C$_8$, Cg, C$_{10}$, C$_{11}$, or C$_{12}$) alkenyloxy or C$_2$-C$_{12}$ (e.g., C$_2$, C$_3$, C$_4$, C$_5$, C$_6$, C$_7$, C$_8$, C$_9$, C$_{10}$, Ci I, or C$_{12}$) alkynyloxy, each of which is optionally substituted with 1-5 (e.g., 1, 2, 3, 4, or 5) R$^s$; C$_3$-C$_{16}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, or C$_{16}$) cycloalkyloxy or C$_3$-C$_{16}$ (e.g., C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, or C$_{16}$) halocycloalkyloxy, each of which is optionally substituted with 1-5 (e.g., 1, 2, 3, 4, or 5) R$^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$; $C_1$-$C_3$ alkylenedioxy; —C(O)O$R^j$; —OC(O)$R^j$; —C(O)S$R^j$; —SC(O) $R^j$; —C(S)S$R^j$; —SC(S)$R^j$; —C(O)N$R^m R^n$; —N$R^k$C(O)$R^j$; —C(N$R^o$)$R^j$; —OC(O)N$R^m R^n$; —N$R^k$C(O)N$R^m R^n$; —N$R^k$C(O)O$R^j$; —S(O)$_n R^j$; —N$R^k$S(O)$_n R^j$; or —P(O)(O$R^m$)(O$R^n$).

Each $R^s$ can be, independently of one another, halo, N$R^m R^n$; nitro; azido, hydroxy; oxo; thioxo; =N$R^o$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$; $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^m R^n$; —N$R^k$C(O)$R^j$; —C(N$R^o$)$R^j$; —OC(O)N$R^m R^n$; N$R^k$C(O)N$R^m R^n$; N$R^k$C(O)O$R^j$; —S(O)$_n R^u$; —N$R^k$S(O)$_n R^j$; or —P(O)(O$R^m$)(O$R^n$).

Each $R^t$ can be, independently of one another:

(i) $C_1$-$C_{12}$ (e.g., $C_1$, $C_2$, $C_3$, $C_4$, $C_5$, $C_6$, $C_7$, $C_8$, $C_9$, $C_{10}$, $C_{11}$ or $C_{12}$) alkyl, $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkyl, halo, N$R^m R^n$; nitro; azido, hydroxy; oxo; thioxo; =N$R^o$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) alkoxy, optionally substituted with 1-5 (e.g., 1, 2, 3, 4, or 5) $R^r$; $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryloxy, optionally substituted with 1-5 (e.g., 1, 2, 3, 4, or 5) $R^g$; $C_2$-$C_{12}$ (e.g., $C_2$, $C_3$, $C_4$, $C_5$, $C_6$, $C_7$, $C_8$, $C_9$, $C_{10}$, $C_{11}$, or $C_{12}$) alkenyloxy or $C_2$-$C_{12}$ (e.g., $C_2$, $C_3$, $C_4$, $C_5$, $C_6$, $C_7$, $C_8$, $C_9$, $C_{10}$ $C_{11}$, or $C_{12}$) alkynyloxy, each of which is optionally substituted with 1-5 (e.g., 1, 2, 3, 4, or 5) $R^s$; $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) cycloalkyloxy or $C_3$-$C_{16}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$) halocycloalkyloxy, each of which is optionally substituted with 1-5 (e.g., 1, 2, 3, 4, or 5) $R^h$; heterocyclyloxy including 3-16 (e.g., 3, 4, 5, 6, 7, 8, 9, 10, 11, 12, 13, 14, 15, or 16) atoms, optionally substituted with 1-5 (e.g., 1, 2, 3, 4, or 5) $R^i$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy, optionally substituted with 1-5 (e.g., 1, 2, 3, 4, or 5) $R^t$; mercapto; $C_1$-$C_6$ (e.g., $C_1$, $C_2$, $C_3$, $C_4$, $C_5$, or $C_6$) thioalkoxy; $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^m R^n$; N$R^k$C(O)$R^j$; —C(N$R^o$)$R^j$; —OC(O)N$R^m R^n$; —N$R^k$C(O)N$R^m R^n$; N$R^k$C(O)O$R^j$; —S(O)$_n R^u$; —N$R^k$S(O)$_n R^j$; or —P(O)(O$R^m$)(O$R^n$); or (ii) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^s$; or (iii) $C_6$-$C_{16}$ (e.g., $C_6$, $C_7$, $C_8$, $C_9$, $C_{10}$, $C_{11}$, $C_{12}$, $C_{13}$, $C_{14}$, $C_{15}$, or $C_{16}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^g$.

Each $R^u$ can be, independently of one another, $R^j$, O$R^j$, or N$R^m R^n$.

Each n can be 0, 1, or 2.

For ease of exposition, it is understood that any recitation of ranges (e.g., $C_1$-$C_{20}$) or subranges of a particular range (e.g., $C_1$-$C_4$, $C_2$-$C_6$) for any of $R^1$, $R^2$, $R^3$, $R^4$, W, X, Y, Z, Z', n, $R^a$, $R^b$, $R^c$, $R^d$, $R^e$, $R^f$, $R^g$, $R^{g'}$, $R^h$, $R^j$, $R^k$, $R^m$, or $R^o$, $R^p$, $R^q$, $R^r$, $R^s$, $R^t$, or $R^u$ expressly includes each of the individual values that fall within the recited range, including the upper and lower limits of the recited range. For example, the range $C_1$-$C_4$ alkyl is understood to mean (e.g., $C_1$, $C_2$, $C_3$, or $C_4$) alkyl.

In general, when X is S (i.e., sulfur), then Y is a bond. In these embodiments, the cyclic PTP1b inhibitor compounds can have formula (II), in which ring B is a thiophene ring:

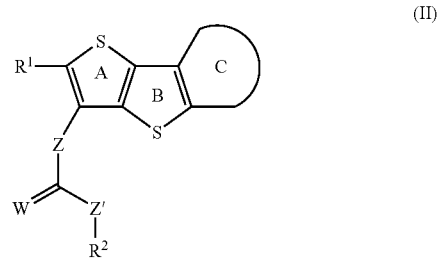

(II)

In some embodiments, X can be C($R^a$)($R^b$) and Y can be N$R^f$. In certain embodiments, one of $R^a$ and $R^b$ can be hydrogen or $C_1$-$C_4$ alkyl, and the other together with $R^f$ can be a bond. In these embodiments, the cyclic PTP1b inhibitor compounds can have formula (III) in which ring B is a pyridyl ring. In certain embodiments, $R^a$ or $R^b$ can be hydrogen.

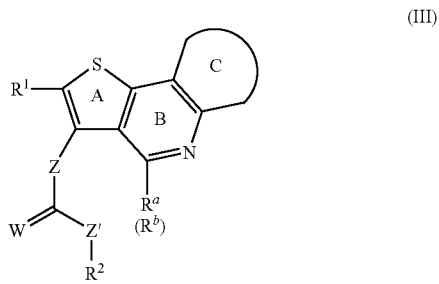

(III)

In other embodiments, X can be N$R^c$ and Y can be C($R^d$)($R^e$). In certain embodiments, one of $R^d$ and $R^e$ can be hydrogen or $C_1$-$C_4$ alkyl, and the other together with $R^c$ can be a bond. In these embodiments, the cyclic PTP1B inhibitor compounds can have formula (IV) in which ring B is a pyridyl ring that is regioisomeric with respect to the pyridiyl ring in formula (III). In certain embodiments, $R^d$ or $R^e$ can be hydrogen.

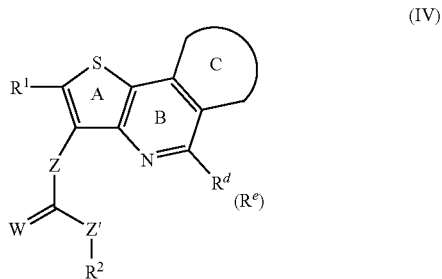

(IV)

In some embodiments, X can be $C(R^a)(R^b)$ and Y can be $C(R^d)(R^e)$. In certain embodiments, one of $R^a$ and $R^b$ can be hydrogen or $C_1$-$C_4$ alkyl, and the other together with $R^d$ or $R^e$ can be a bond, and one of $R^d$ and $R^e$ is hydrogen or $C_1$-$C_4$ alkyl, and the other together with $R^a$ or $R^b$ is a bond. In these embodiments, the cyclic PTP1b inhibitor compounds can have formula (V) in which ring B is a phenyl ring. In certain embodiments, $R^a$, $R^b$, $R^d$ or $R^e$ can be hydrogen.

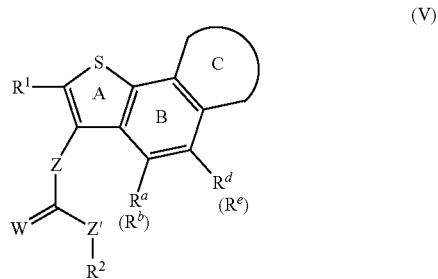

(V)

Embodiments can include one or more of the following features.

In some embodiments, $R^1$ can be cyano, —C(O)$R^j$, —C(O)O$R^j$, —C(O)S$R^j$, —C(S)S$R^j$, or —C(O)NR$^m$R$^n$. In certain embodiments, $R^1$ can be —C(O)O$R^j$, in which $R^j$ can be hydrogen or $C_1$-$C_6$ alkyl (e.g., $CH_3$). In other embodiments, $R^1$ can be cyano.

In some embodiments, $R^1$ can be heteroaryl including 5-10 atoms, optionally substituted with from 1-3 $R^g$. In certain embodiments, $R^1$ can be tetrazolyl.

In some embodiments, W and Z' can both be O. Z can be O, NR$^p$, S; or $C_1$-$C_{12}$ alkylene, $C_2$-$C_{12}$ alkenylene, $C_2$-$C_{12}$ alkynylene, O($C_1$-$C_{12}$ alkylene), NR$^p$($C_1$-$C_{12}$ alkylene), S($C_1$-$C_{12}$ alkylene), SO($C_1$-$C_{12}$ alkylene), or SO$_2$($C_1$-$C_{12}$ alkylene), each of which can be optionally substituted with 1-5 (e.g., 1-4, 1-3, 1-2) $R^q$. In certain embodiments, Z can be O($C_1$-$C_3$ alkylene), NR$^p$($C_1$-$C_3$ alkylene), S($C_1$-$C_3$ alkylene), SO($C_1$-$C_3$ alkylene), or SO$_2$($C_1$-$C_3$ alkylene), each of which is optionally substituted with 1-5 (e.g., 1-4, 1-3, 1-2) $R^q$, and each of which having the heteroatom or heteroatom group attached to ring A. An exemplary Z group is OCH$_2$, in which the oxygen is attached to ring A. An exemplary $R^p$ group is hydrogen.

In some embodiments, $R^q$ can be halo; nitro; NH$_2$; hydroxy; oxo; =NR$^o$; $C_1$-$C_{12}$ alkoxy, optionally substituted with 1-5 $R^r$; OCF$_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; NR$^m$R$^n$; —C(O)$R^j$; —C(O)$R^j$; —C(O)O$R^j$; —OC(O)$R^j$; —C(O)NR$^m$R$^n$; —NR$^k$C(O)$R^j$; —OC(O)NR$^m$R$^n$; —NR$^k$C(O)NR$^m$R$^n$; —NR$^k$C(O)O$R^j$; —S(O)$_n$R$^u$; or —NR$^k$S(O)$_n$R$^j$.

In certain embodiments, $R^q$ can be F; Cl; nitro; NH$_2$; hydroxy; $C_1$-$C_{12}$ alkoxy, optionally substituted with 1-5 $R^r$; OCF$_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; NR$^m$R$^n$; —C(O)$R^j$; —C(O)$R^j$; —C(O)O$R^j$; —OC(O)$R^j$; —C(O)NR$^m$R$^n$; NR$^k$C(O)$R^j$; —OC(O)NR$^m$R$^n$; NR$^k$C(O)NR$^m$R$^n$; —NR$^k$C(O)O$R^j$; —S(O)$_n$R$^u$; or —NR$^k$S(O)$_n$R$^j$.

In some embodiments, $R^2$ can be hydrogen.

In some embodiments, $R^2$ can be $C_1$-$C_{16}$ alkyl, optionally substituted with from 1-10 (e.g., 1-7, 1-5, 1-4, 1-3, 1-2) $R^r$ and/or optionally inserted with from 1-10 (e.g., 1-4, 1-3, 1-2) heteroatoms selected from the group consisting of nitrogen, oxygen or sulfur; or $C_1$-$C_{16}$ haloalkyl, optionally substituted with from 1-10 $R^r$; in which each $R^r$ can be, independently of one another, NH$_2$, nitro; azido; hydroxy; oxo; $C_1$-$C_{12}$ alkoxy, optionally substituted with 1-5 $R^r$; OCF$_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; NR$^m$R$^n$; —C(O)$R^j$, —C(O)O$R^j$; —OC(O)$R^j$; —C(O)NR$^m$R ; —NR$^k$C(O)$R^j$; —OC(O)NR$^m$R$^n$; —NR$^k$C(O)NR$^m$R$^n$; —NR$^k$C(O)O$R^j$; —S(O)$_n$R$^u$; or —NR$^k$S(O)$_n$R$^j$.

In some embodiments, $R^2$ can be $C_3$-$C_8$ cycloalkyl or $C_3$-$C_8$ halocycloalkyl, each of which can be optionally substituted with from 1-5 (e.g., 1-4, 1-3, 1-2) $R^h$; in which each $R^h$ can be, independently of one another, NH$_2$, nitro; azido; hydroxy; oxo; $C_1$-$C_{12}$ alkoxy, optionally substituted with 1-5 $R^r$; OCF$_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; NR$^m$R$^n$; —C(O)$R^j$; —C(O)O$R^j$; —OC(O)$R^j$; —C(O)NR$^m$R$^n$; —NR$^k$C(O)$R^j$; —OC(O)NR$^m$R$^n$; —NR$^k$C(O)NR$^m$R$^n$; —NR$^k$C(O)O$R^j$; —S(O)$_n$R$^u$; or —NR$^k$S(O)$_n$R$^j$; or $C_2$-$C_6$ alkenyl or $C_2$-$C_6$ alkynyl.

In some embodiments, $R^2$ can be $C_3$-$C_8$ cycloalkenyl, heterocyclyl including 3-8 atoms, or heterocycloalkenyl including 3-8 atoms, each of which can be optionally substituted with from 1-5 (e.g., 1-4, 1-3, 1-2) $R^i$; in which each $R^i$ can be, independently of one another, halo; NH$_2$, nitro; azido; hydroxy; oxo; $C_1$-$C_{12}$ alkoxy, optionally substituted with 1-5 $R^r$; OCF$_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$; or $C_2$-$C_6$ alkenyl or $C_2$-$C_6$ alkynyl.

In some embodiments, $R^2$ can be $C_2$-$C_{12}$ alkenyl or $C_2$-$C_{12}$ alkynyl, each of which can be optionally substituted with from 1-5 (e.g., 1-4, 1-3, 1-2) $R^s$; in which each $R^s$ can be, independently of one another, halo; $NH_2$; nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$.

In some embodiments, $R^2$ can be $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which can be optionally substituted with from 1-10 (e.g., 1-7, 1-5, 1-4, 1-3, 1-2) $R^t$; in which each $R^t$ can be, independently of one another, $C_1$-$C_{12}$ alkyl, $C_1$-$C_{12}$ alkyl, halo; $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$; or $C_2$-$C_6$ alkenyl or $C_2$-$C_6$ alkynyl.

In some embodiments, $R^2$ can be $C_6$-$C_{16}$ aryl or heteroaryl including 5-16 atoms, each of which can be optionally substituted with from 1-10 $R^g$, in which each $R^g$ can be, independently of one another, halo; $NH_2$, nitro; azido; hydroxy; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$; or $C_2$-$C_6$ alkenyl or $C_2$-$C_6$ alkynyl.

In some embodiments, each $R^3$ or $R^4$, can be, independently of one another, halo; $NR'''R''$; nitro; hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$; —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$.

In some embodiments, each $R^3$ or $R^4$, can be, independently of one another, $C_1$-$C_{12}$ (e.g., $C_1$-$C_6$, $C_1$-$C_4$) alkyl, optionally substituted with from 1-10 (e.g., 1-5, 1-3) $R^r$ and/or optionally inserted with from 1-10 (e.g., 1-5, 1-3) heteroatoms selected from the group consisting of nitrogen, oxygen or sulfur; or $C_1$-$C_{12}$ (e.g., $C_1$-$C_6$, $C_1$-$C_4$) haloalkyl, optionally substituted with from 1-10 (e.g., 1-5, 1-3) $R^r$; in which each $R^r$ can be, independently of one another, $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$; —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$.

In some embodiments, each $R^3$ or $R^4$, can be, independently of one another, $C_3$-$C_{20}$ (e.g., $C_3$-$C_8$) cycloalkyl or $C_3$-$C_{20}$ (e.g., $C_3$-$C_8$) halocycloalkyl, each of which can be optionally substituted with from 1-10 (e.g., 1-5, 1-3) $R^h$; in which each $R^h$ can be, independently of one another, $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$.

In some embodiments, each $R^3$ or $R^4$, can be, independently of one another, $C_2$-$C_{12}$ (e.g., $C_2$-$C_6$) alkenyl or $C_2$-$C_{12}$ (e.g., $C_2$-$C_6$) alkynyl, each of which can be optionally substituted with from 1-10 (e.g., 1-5, 1-3) $R^s$; in which each $R^s$ can be, independently of one another, halo; $NH_2$; nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —C(O)$R^j$, —C(O)O$R^j$; —OC(O)$R^j$; —C(O)N$R'''R''$; —$NR^kC(O)R^j$; —OC(O)$NR'''R''$; —$NR^kC(O)NR'''R''$; —$NR^kC(O)OR^j$; —S(O)$_nR^u$; or —$NR^kS(O)_nR^j$.

In some embodiments, each $R^3$ or $R^4$, can be, independently of one another, $C_7$-$C_{12}$ (e.g., $C_7$-$C_{10}$) aralkyl, heteroaralkyl including 6-20 (e.g., 6-10) atoms, $C_8$-$C_{20}$ (e.g., $C_8$-$C_{10}$) arylcycloalkyl, $C_8$-$C_{20}$ (e.g., $C_8$-$C_{10}$) arylcycloalkenyl, arylheterocyclyl including 8-20 (e.g., 8-10) atoms, or arylheterocycloalkenyl including 8-20 (e.g., 8-10) atoms, each of which can be optionally substituted with from 1-10 (e.g., 1-5, 1-3) $R^t$; in which each $R^t$ can be, independently of one another, halo; $NH_2$, nitro; azido; hydroxy; oxo; $C_1$-$C_{12}$ alkoxy, optionally substituted with 1-5 $R^r$; $OCF_3$; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —$C(O)R^j$, —$C(O)OR^j$; —$OC(O)R^j$; —$C(O)NR'''R''$; —$NR^kC(O)R^j$; —$OC(O)NR''R''$; —$NR^kC(O)NR'''R''$; —$NR^kC(O)OR^j$; —$S(O)_nR^u$; or —$NR^kS(O)_nR^j$.

In some embodiments, each $R^3$ or $R^4$, can be, independently of one another, $C_6$-$C_{10}$ (e.g., $C_6$) aryl or heteroaryl including 5-10 (e.g., 5-6) atoms, each of which can be optionally substituted with from 1-10 (e.g., 1-5, 1-3) $R^g$, in which each $R^g$ can be, independently of one another, halo; $NH_2$, nitro; azido; hydroxy; $C_1$-$C_{12}$ alkoxy, optionally substituted with 1-5 $R^r$; $OCF_3$; $C_6$-$C_{16}$ aryloxy, optionally substituted with 1-5 $R^{g'}$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; $NR'''R''$; —$C(O)R^j$; —$C(O)OR^j$; —$OC(O)R^j$; —$C(O)NR'''R''$; —$NR^kC(O)R^j$; —$OC(O)NR''R''$; —$NR^kC(O)NR'''R''$; —$NR^kC(O)OR^j$; —$S(O)_nR^u$; or —$NR^kS(O)_nR^j$.

In some embodiments, ring C can be a fused $C_6$-$C_{16}$ (e.g., $C_6$-$C_{10}$) aryl, which is optionally substituted with from 1-10 (e.g., 1-5, 1-3) $R^3$. In certain embodiments, ring C can be a fused phenyl ring that can be substituted or unsubstituted.

In some embodiments, ring C can be a fused heteroaryl including 5-16 (e.g., 5-10) atoms, each of which is optionally substituted with from 1-10 (e.g., 1-5, 1-3) $R^3$. In certain embodiments, ring C can be a fused pyridyl ring that can be substituted or unsubstituted.

A subset of compounds includes those having formula (VI) in which ring C can be a fused phenyl ring. Embodiments can include one or more of the following features.

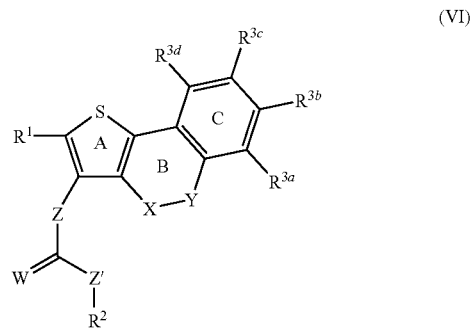

(VI)

In some embodiments, ring B can be a thiophene ring, a pyridine ring or a phenyl ring;

In some embodiments, $R^1$ can be tetrazolyl, cyano, or —$COOR^j$ in which $R^j$ can be, e.g., H or $CH_3$;

In some embodiments, Z can be $OCH_2$, in which the oxygen atom is attached to ring A.

In some embodiments, W can be O.

In some embodiments, Z' can be O.

In some embodiments, $R^2$ can be hydrogen.

In some embodiments, ring B can be a thiophene ring, a pyridine ring or a phenyl ring; and $R^1$ can be tetrazolyl, cyano, or —$COOR^j$ in which $R^j$ can be, e.g., H or $CH_3$.

In some embodiments, ring B can be a thiophene ring, a pyridine ring or a phenyl ring; $R^1$ can be tetrazolyl, cyano, or —$COOR^j$ in which $R^j$ can be, e.g., H or $CH_3$; and Z can be $OCH_2$, in which the oxygen atom is attached to ring A.

In some embodiments, ring B can be a thiophene ring, a pyridine ring or a phenyl ring; $R^1$ can be tetrazolyl, cyano, or —$COOR^j$ in which $R^j$ can be, e.g., H or $CH_3$; Z can be $OCH_2$, in which the oxygen atom is attached to ring A; and both W and Z' can both be O.

In some embodiments, ring B can be a thiophene ring, a pyridine ring or a phenyl ring; $R^1$ can be tetrazolyl, cyano, or —$COOR^j$ in which $R^j$ can be, e.g., H or $CH_3$; Z can be $OCH_2$, in which the oxygen atom is attached to ring A; both W and Z' can both be O; and $R^2$ can be hydrogen.

In some embodiments, $R^{3a}$, $R^{3b}$, $R^{3c}$, and $R^{3d}$ can each be hydrogen. In some embodiments, one, two or three of $R^{3a}$, $R^{3b}$, $R^{3c}$, or $R^{3d}$ can be $R^3$, and the others can be hydrogen. When two or more of $R^{3a}$, $R^{3b}$, $R^{3c}$, or $R^{3d}$ are $R^3$, each $R^3$ can be, independently, as defined elsewhere. In certain embodiments, one, two or three of $R^{3a}$, $R^{3b}$, $R^{3c}$, or $R^{3d}$ can be, independently of one another, halo, $C_1$-$C_6$ alkyl, $C_1$-$C_6$ alkoxy, $C_3$-$C_{10}$ cycloalkyl, $C_7$-$C_{10}$ aralkyl, —$C(O)OR^j$, —$C(O)NR'''R''$, —$NR^kC(O)OR^j$, —$NR^kC(O)NR'''R''$, —$NR^kC(O)R^j$, or —$NR'''R''$, and the others can be hydrogen.

In some embodiments, $R^{3a}$, $R^{3b}$, $R^{3c}$, and $R^{3d}$ can each be other than hydrogen.

In certain embodiments, $R^{3a}$ can be $R^3$, and each of $R^{3b}$, $R^{3c}$, and $R^{3d}$ can be hydrogen. In certain embodiments, $R^{3b}$ can be $R^3$, and each of $R^{3a}$, $R^{3c}$, and $R^{3d}$ can be hydrogen. In certain embodiments, $R^{3c}$ can be $R^3$, and each of $R^{3a}$, $R^{3b}$, and $R^{3d}$ can be hydrogen. In certain embodiments, $R^{3d}$ can be $R^3$, and each of $R^{3a}$, $R^{3b}$, and $R^{3d}$ can be hydrogen. In certain embodiments, $R^{31}$ and $R^{3c}$ can each be $R^3$, and each of $R^c$ and $R^d$ can be hydrogen.

In some embodiments, one of $R^{3a}$, $R^{3b}$, $R^{3c}$, or $R^{3d}$ (e.g., $R^{3a}$ or $R^{3b}$) can be halo (e.g., Cl) and the others can be hydrogen.

In some embodiments, one of $R^{3a}$, $R^{3b}$, $R^{3c}$, or $R^{3d}$ (e.g., $R^3b$) can be $C_7$-$C_{10}$ aralkyl (e.g., benzyl) and the others can be hydrogen.

In some embodiments, one of $R^{3a}$, $R^{3b}$, $R^{3c}$, or $R^{3d}$ (e.g., $R^{3b}$) can be —$C(O)OR^j$ and the others can be hydrogen. In certain embodiments, $R^j$ can be $C_1$-$C_6$ alkyl (e.g., tert-butyl).

In some embodiments, one of $R^{3a}$, $R^{3b}$, $R^{3c}$, or $R^{3d}$ (e.g., $R^{3a}$ or $R^{3c}$) can be $C_1$-$C_6$ alkyl (e.g., $CH_3$) and the others can be hydrogen.

In some embodiments, one of $R^{3a}$, $R^{3b}$, $R^{3c}$, or $R^{3d}$ (e.g., $R^{3a}$ or $R^{3b}$) can be $C_1$-$C_6$ alkoxy (e.g., $OCH_3$) and the others can be hydrogen.

In some embodiments, one of $R^{3a}$, $R^{3b}$, $R^{3c}$, or $R^{3d}$ (e.g., $R^{3b}$) can be $C_3$-$C_{10}$ cycloalkyl and the others can be hydrogen. In certain embodiments, the cycloalkyl group can be:

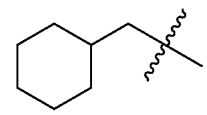

In some embodiments, one of $R^{3a}$, $R^{3b}$, $R^{3c}$, or $R^{3d}$ (e.g., $R^{3b}$) can be —C(O)NR$^m$R$^n$ and the others can be hydrogen. In certain embodiments, one of R$^m$ and R$^n$ can be hydrogen, and the other can be $C_7$-$C_{10}$ aralkyl (e.g., benzyl). In certain embodiments, one of R$^m$ and R$^n$ can be hydrogen, and the other can be $C_3$-$C_{10}$ cycloalkyl (e.g., cyclohexyl or

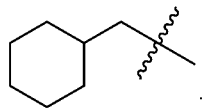

In some embodiments, one of $R^{3a}$, $R^{3b}$, $R^{3c}$, or $R^{3d}$ (e.g., $R^{3a}$ or $R^{3c}$) can be —NR$^k$C(O)OR$^j$ and the others can be hydrogen. In certain embodiments, R$^k$ can be hydrogen or $C_3$-$C_{10}$ cycloalkyl (e.g., cyclohexyl). In certain embodiments, R$^j$ can be $C_1$-$C_6$ alkyl (e.g., CH$_3$ or tert-butyl).

In some embodiments, one of $R^{3a}$, $R^{3b}$, $R^{3c}$, or $R^{3d}$ (e.g., $R^{3a}$ or $R^{3c}$) can be —NR$^k$C(O)NR$^m$R$^n$ and the others can be hydrogen. In certain embodiments, R$^k$ can be hydrogen or $C_3$-$C_{10}$ cycloalkyl (e.g., cyclohexyl). In certain embodiments, one of R$^m$ and R$^n$ can be hydrogen, and the other can be $C_3$-$C_{10}$ cycloalkyl (e.g., cyclohexyl). In certain embodiments, one of R$^m$ and R$^n$ can be hydrogen, and the other can be $C_1$-$C_6$ alkyl (e.g., ethyl).

In some embodiments, one of $R^{3a}$, $R^{3b}$, $R^{3c}$, or $R^{3d}$ (e.g., $R^{3a}$ or $R^{3c}$) can be —NR$^k$C(O)R$^j$ and the others can be hydrogen. In certain embodiments, R$^k$ can be $C_3$-$C_{10}$ cycloalkyl (e.g., cyclohexyl or

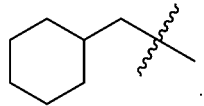

In certain embodiments, R$^j$ can be $C_6$-$C_{10}$ aryl (e.g., phenyl). In certain embodiments, R$^j$ can be $C_1$-$C_6$ alkyl (e.g., CH$_3$).

In some embodiments, one of $R^{3a}$, $R^{3b}$, $R^{3c}$, or $R^{3d}$ (e.g., $R^{3a}$ or $R^{3c}$,) can be —NR$^m$R$^n$ and the others can be hydrogen.

In certain embodiments, R$^m$ and R$^n$ can both be hydrogen.

In certain embodiments, one of R$^m$ and R$^n$ can be hydrogen, and the other can be $C_7$-$C_{10}$ aralkyl (e.g., benzyl).

In certain embodiments, one of R$^m$ and R$^n$ can be hydrogen, and the other can be heterocyclyl including 3-10 atoms, optionally substituted with from 1-3 R$^i$. In some embodiments, the heterocycly group can be tetrahydropyranyl. In other embodiments, the heterocycly group can be

In these embodiments, R$^i$ can be —C(O)OR$^j$, —C(O)NR$^m$R$^n$, or C(O)R$^j$.

In some of these embodiments, R$^j$ can be $C_1$-$C_6$ alkyl (e.g., tert-butyl), optionally substituted with from 1-3 R$^r$; $C_1$-$C_6$ haloalkyl, optionally substituted with from 1-3 R$^r$; $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; $C_7$-$C_{12}$ aralkyl (e.g., benzyl), optionally substituted with from 1-3 R$^t$; heteroaralkyl including from 7-12 atoms (e.g., pyridylmethyl), optionally substituted with from 1-3 R$^t$; heterocyclyl including from 3-8 atoms(e.g., piperidinyl), optionally substituted with from 1-3 R$^i$; $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$. In certain embodiments, R$^j$ can be $C_1$-$C_6$ alkyl (e.g., tert-butyl); $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; or $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$.

In some embodiments, each of R$^m$ and R$^n$ can be, independently of one another, hydrogen; $C_1$-$C_6$ alkyl (e.g., tert-butyl), optionally substituted with from 1-3 R$^r$; $C_1$-$C_6$ haloalkyl, optionally substituted with from 1-3 R$^r$; $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; $C_7$-$C_{12}$ aralkyl (e.g., benzyl), optionally substituted with from 1-3 R$^t$; heteroaralkyl including from 7-12 atoms (e.g., pyridylmethyl), optionally substituted with from 1-3 R$^t$; heterocyclyl including from 3-8 atoms(e.g., piperidinyl), optionally substituted with from 1-3 R$^i$; $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$. In certain embodiments, each of R$^m$ and R$^n$ can be, independently of one another, hydrogen; $C_1$-$C_6$ alkyl (e.g., tert-butyl); $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; or $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$; $C_7$-$C_{12}$ aralkyl (e.g., benzyl), optionally substituted with from 1-3 R$^t$; or heteroaralkyl including from 7-12 atoms (e.g., pyridylmethyl), optionally substituted with from 1-3 R$^t$.

In some embodiments, R$^i$ can be —SO$_2$R$^u$, in which R$^u$ can be $C_1$-$C_6$ alkyl (e.g., CH$_2$CH$_3$), optionally substituted with from 1-3 R$^r$; $C_1$-$C_6$ haloalkyl, optionally substituted with from 1-3 R$^r$; $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; $C_7$-$C_{12}$ aralkyl (e.g., benzyl), optionally substituted with from 1-3 R$^t$; heteroaralkyl including from 7-12 atoms (e.g., pyridylmethyl), optionally substituted with from 1-3 R$^t$; heterocyclyl including from 3-8 atoms (e.g., piperidinyl), optionally substituted with from 1-3 R$^i$; $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$. In certain embodiments, R$^u$ can be $C_1$-$C_6$ alkyl (e.g., CH$_2$CH$_3$); $C_6$-$C_{10}$ aryl (e.g., phenyl, naphthyl), optionally substituted with from 1-3 R$^g$; heteroaryl including from 5-10 atoms (e.g., pyridyl, thienyl, furyl, imidazolyl), optionally substituted with from 1-3 R$^g$; $C_3$-$C_{10}$ cycloalkyl (e.g., cyclopropyl, cyclobutyl, cyclopentyl, cyclohexyl, cycloheptyl, cyclooctyl, cyclohexylmethyl), optionally substituted with from 1-3 R$^h$; $C_7$-$C_{12}$ aralkyl (e.g., benzyl), optionally substituted with from 1-3 R$^t$; or heteroaralkyl including from 7-12 atoms (e.g., pyridylmethyl), optionally substituted with from 1-3 R$^t$.

In some embodiments z can be 0-5 (e.g, 0-4, 0-3, 0-2, e.g., 0. 1, or 2).

In certain embodiments, one of R'" and R" can be hydrogen, and the other can be $C_3$-$C_{10}$ cycloalkyl (e.g., cyclohexyl or

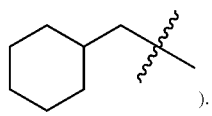

).

In certain embodiments, both R'" and R" can be other than hydrogen.

In certain embodiments, In some embodiments, two of $R^{3a}$, $R^{3b}$, $R^{3c}$, or $R^{3d}$ (e.g., $R^{3a}$ and $R^{3c}$) can be $C_1$-$C_6$ alkyl (e.g., $CH_3$) and the others can be hydrogen.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species.

The compounds described herein can be synthesized according to methods described herein and/or conventional, organic chemical synthesis methods from commercially available starting materials and reagents. The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

In certain embodiments, the cyclic PTP1b inhibitor compounds described herein can generally be prepared as delineated in Scheme A below.

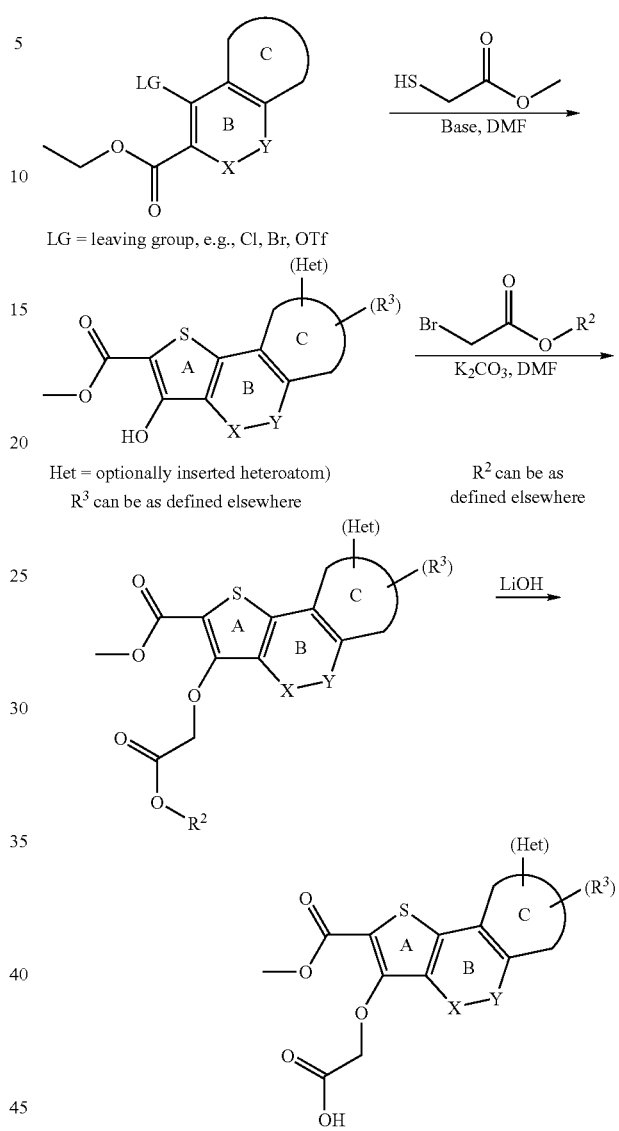

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The term "pharmaceutically acceptable carrier or adjuvant" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In general, the compounds described herein can be used for treating, controlling, ameliorating, preventing, delaying the onset of, or reducing the risk of developing one or more diseases, disorders, conditions or symptoms mediated by PTP1B (e.g., type 2 diabetes, obesity, metabolic syndromes). A disorder or physiological condition that is mediated by PTP1b refers to a disorder or condition wherein PTP1b can trigger the onset of the condition, or where inhibition of a particular PTPase can affect signaling in such a way so as to treat, control, ameliorate, prevent, delay the onset of, or reduce the risk of developing the disorder or condition. Examples of such disorders include, but are not limited to, type 1 and type 2 diabetes, obesity, cancer, autoimmune diseases, allergic disorders, acute and chronic inflammation, metabolic syndrome, and osteoporosis.

The compounds described herein generally have an inhibition constant $IC_{50}$ of less than about 500 μM (e.g., less than about 400 μM, less than about 300 μM, less than about 200 μM, less than about 100 μM). In certain embodiments, compounds described herein can have an inhibition constant $IC_{50}$ of from about 500 μM to about 300 nM.

In some embodiments, the compounds described herein can be coadministered with one or more other threapeutic agents. In certain embodiments, the additional agents may be administered separately, as part of a multiple dose regimen, from the compounds of this invention (e.g., sequentially, e.g., on different overlapping schedules with the administration of one or more compounds of formula (I), (II), (III), (IV), (V), (VI), (VII) or (VIII)). Alternatively, these agents may be part of a single dosage form, mixed together with the compounds of this invention in a single composition. In still another embodiment, these agents can be given as a separate dose that is administered at about the same time that one or more compounds of formula (I), (II), (III), (IV), (V), (VI), (VII) or (VIII) are administered (e.g., simultaneously with the administration of one or more compounds of formula (I), (II), (III), (IV), (V), (VI), (VII), or (VIII)). When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen.

Other therapeutic agents can include, e.g., insulin and insulin analogues and mimetics; PPAR agonists (e.g., pioglitazone, rosiglitazone), statins (e.g., simvastatin, e.g., Zocor; atorvastatin calcium (e.g., lipitor); ACE inhibitors (e.g., lisinopril), and ARB inhibitors.

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/Kg to about 1000 mg/Kg, (e.g., from about 0.01 to about 100 mg/kg, from about 0.1 to about 100 mg/Kg, from about 1 to about 100 mg/Kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

The invention will be further described in the following examples. It should be understood that these examples are for illustrative purposes only and are not to be construed as limiting this invention in any manner.

EXAMPLES

General

General Procedure A [Ester hydrolysis]: The diester is combined in THF (~3 ml) and water (~3 ml). Then LiOH.H$_2$O (3-6 equiv) is added and the mixture is stirred until LC showed absence of the starting material. After removal of TBF in vacuo, the mixture is acidified using 1N HCl until a precipitate formed. Filtration followed by washing with water yields the desired products.

General Prodedure B [Suzuki reaction]: Aryl halide (1 equiv) is combined with palladium source, phosphine ligand, KF (2-3 equiv), and boronic acid (1.0-1.5 equiv). The septum-sealed vessel is evacuated and purged with nitrogen 3× then THF (~1 ml) is added. The mixture is stirred at appropriate temperature for the indicated time. Purification of crude material is accomplished by column chromatography.

Example 1

1-Carboxymethoxy-3,8-dithia-cyclopenta[a]indene-2-carboxylic acid

Step A: Sodium tert-butoxide (360 mg, 3.7 mmol, 3.3 equiv) was added to a solution of methyl thioglycolate (0.110 ml, 1.23 mmol, 1.1 equiv) in DMF (10 ml). 2-chloro-benzo[b]thiophene-3-carboxylic acid methyl ester (235 mg, 1.12 mmol, 1 equiv, available from Maybridge) was then added and the mixture became orange. When no starting material was observed by TLC, water was added followed by extraction with EtOAc. Purification by column chromatography yielded 162 mg (61%) of 1-hydroxy-3,8-dithia-cyclopenta[a]indene-2-carboxylic acid methyl ester as an orange solid.

1H NMR (400 MHz, CHLOROFORM-D) δ ppm 3.96 (s, 3H) 7.51-7.40 (dd, J=6.06, 3.28 Hz, 2H) 7.89-7.80 (m, 2H) 10.06 (s, 1H).

Step B: tert-Butyl bromoacetate (0.082 ml, 0.56 mmol, 1.3 equiv) was added to a mixture of NaOt-Bu (50 mg, 1.2 equiv) and 1-hydroxy-3,8-dithia-cyclopenta[a]indene-2-carboxylic acid methyl ester (113 mg, 0.43 mmol, 1 equiv) in DMF (10 ml). The resulting mixture was stirred at 60° C. for 16 hr. Addition of water followed by extraction with EtOAc and washing with water left crude product. Purification by column chromatography gave 140 mg (86%) of 1-tert-butoxy-carbonylmethoxy-3,8-dithia-cyclopenta[a]indene-2-carboxylic acid methyl ester as an orange solid.

1H NMR (400 MHz, CHLOROFORM-D) δ ppm 1.47 (s, 9H) 3.91 (s, 3H) 4.97 (s, 2H) 7.47-7.41 (m, 2H) 7.90-7.82 (m, 2H).

Step C: Following General Procedure A, 1-tert-butoxycarbonylmethoxy-3,8-dithia-cyclopenta[a]indene-2-carboxylic acid methyl ester (76 mg, 0.2 mmol) was stirred for 2 hr at 40° C. Work-up yielded 57 mg (92%) of the title compound. 1H NMR (400 MHz, DMSO-D6) δ ppm 4.69 (d, J=1.01 Hz, 2H) 7.55-7.46 (m, 2H) 8.08-8.02 (m, 1H) 8.13-8.09(m, 1H). HRMS (ESI-, m/z) calcd for [M-H]$^{1-}$, 306.97403, found, 306.97322.

Example 2

1-Carboxymethoxy-6-chloro-3,8-dithia-cycloventa[a]indene-2-carboxylic acid

Step A: 6-chloro-2-hydroxy-benzo[b]thiophene-3-carboxylic acid methyl ester (2.46 g, 10.1 mmol) was cooled to 0° C. in a solution of DCM (25 ml) and Et$_3$N (25 ml). Tf$_2$O (2.56 ml, 15.2 mmol, 1.5 equiv) was added dropwise, then stirred for 1 hr. The resulting solution was washed twice with water, saturated NaHCO$_3$, then water, followed by drying over MgSO$_4$. This was filtered and the solvent removed in vacuo. The crude material was purified by column chromatography leaving 2.61 g (68%) of 6-chloro-2-trifluoromethanesulfonyloxy-benzo[b]thiophene-3-carboxylic acid methyl ester as a white solid.

1H NMR (400 MHz, CHLOROFORM-D) δ ppm 4.00 (s, 3H), 7.50 (dd, J=8.8, 1.8 Hz, 1H), 7.76 (d, J=8.8 Hz, 1H), 7.85 (d, J=1.5 Hz, 1H).

Step B: Methyl thioglycolate (0.169 ml, 1.9 mmol) was added to a solution of 6-chloro-2-trifluoromethanesulfonyloxy-benzo[b]thiophene-3-carboxylic acid methyl ester (0.644 g, 1.72 mmol) in Et$_3$N (10 ml) and DMF (5 ml) and stirred for 16 hr. Addition of water followed by extraction with EtOAc, drying over MgSO$_4$, and removal of solvent yielded 0.564 g of crude product. NaH 60% in oil (65mg) was added to 449 mg of the crude product in DMF (8 ml) and stirred for 30 min. Water was added and the mixture acidified with 1N HCl. Extraction with EtOAc, drying over MgSO$_4$, and removal of solvent left 0.173 g (43%) of 6-chloro-1-hydroxy-3,8-dithia-cyclopenta[a]indene-2-carboxylic acid methyl ester as a light orange solid.

1H NMR (400 MHz, CHLOROFORM-D) δ ppm 3.96 (s, 3H) 7.42 (dd, J=8.59, 1.77 Hz, 1H) 7.79 (d, J=8.59 Hz, 1H) 7.88 (d, J=1.77 Hz, 1H) 10.02 (s, 1H). HRMS (ESI-, m/z) calcd for [M-H]$^{1-}$, 296.94523, found, 296.4479.

tert-Butyl bromoacetate (0.10 ml, 0.65 mmol, 1.3 equiv) was added to a mixture of NaOt-Bu (60 mg, 1.2 equiv) and 6-chloro-1-hydroxy-3,8-dithia-cyclopenta[a]indene-2-carboxylic acid methyl ester (150 mg, 0.5 mmol) in DMF (6 ml) and stirred at 60° C. for 2.5 hr then at RT for 3 days. Water was added and the mixture was extracted with EtOAc. After removal of solvent, purification by column chromatography gave 140 mg (68%) of 1-tert-butoxycarbonylmethoxy-6-chloro-3,8-dithia-cyclopenta[a]indene-2-carboxylic acid methyl ester as orange solids.

1H NMR (400 MHz, CHLOROFORM-D) δ ppm 1.47 (s, 9H), 4.95 (s, 2H), 7.41 (dd, J=8.6, 2.0 Hz, 1H), 7.77 (d, J=8.6 Hz, 1H), 7.83 (d, J=1.8 Hz, 1H)

Following General Procedure A, 1-tert-butoxycarbonyl-methoxy-6-chloro-3,8-dithia-cyclopenta[a]indene-2-carboxylic acid methyl ester (48 mg, 0.12 mmol) was stirred for 16 hr. Work-up yielded 26 mg (65%) of the title compound as off-white solids.

1H NMR (400 MHz, DMSO-D6) δ ppm 5.06 (s, 2H) 7.55 (dd, J=8.59, 2.02 Hz, 1 H) 8.12 (d, J=8.59 Hz, 1H) 8.32 (d, J=1.77 Hz, 1H). HRMS (ESI-, m/z) calcd for [M−H]$^{1-}$, 340.93506, found, 340.93465.

Example 3

1-Carboxymethoxy-7-chloro-3,8-dithia-cyclopenta [a]indene-2-carboxylic acid

Step A: Trifluoromethanesulfonyl anhydride (0.49 ml, 2.9 mmol, 2.0 equiv) was added dropwise to a 0° C. solution of 7-chloro-3-hydroxy-benzo[b]thiophene-2-carboxylic acid methyl ester (355 mg, 1.46 mmol) in Et$_3$N (8 ml) and DCM (5 ml). After reaching RT, the mixture was adsorbed onto silica gel and column chromatography yielded 110 mg (20%) of 7-chloro-3-trifluoromethanesulfonyloxy-benzo[b] thiophene-2-carboxylic acid methyl ester as a white solid.

1H NMR (400 MHz, CHLOROFORM-D) δ ppm 4.01 (s, 3H), 7.50 (t, J=8.0 Hz, 1H), 7.56-7.65 (m, 1H), 7.77 (d, J=8.1 Hz, 1H)

Steps B-C: 7-chloro-3-trifluoromethanesulfonyloxy-benzo[b]thiophene-2-carboxylic acid methyl ester (104 mg, 0.28 mmol) in DMF (2 ml) was added to a mixture of sodium tert-butoxide (54 mg, 0.56 mmol) and methyl thioglycolate dissolved in DMF (1 ml). After 16 hr, water was added and the mixture was neutralized with 1N HCl. It was then extracted with EtOAc, dried over MgSO$_4$, filtered, and the solvent was removed in vacuo. An inseparable mixture of hydrolized starting material/desired product with a 1:1.6 ratio resulted. This mixture was then treated with ethyl bromoacetate (120 µl, 1.1 mmol) in the presence of K$_2$CO$_3$ (90 mg, 0.65 mmol) at 60° C. After 24 hr, water was added and the mixture was extracted with EtOAc. Removal of solvent and purification by reverse phase HPLC yielded 19 mg (16% over 2 steps) of 7-chloro-1-ethoxycarbonylmethoxy-3,8-dithia-cyclopenta [a]indene-2-carboxylic acid methyl ester. HRMS (ESI-, m/z) calcd for [M-H]$^{1-}$, 340.93506, found, 340.9345.

Following General Procedure A, 7-chloro-1-ethoxycarbo-nylmethoxy-3,8-dithia-cyclopenta[a]indene-2-carboxylic acid methyl ester (19 mg, 0.05 mmol) was stirred for 15 hr. Work-up yielded 11 mg (65%) of the title compound as white solids. 1H NMR (400 MHz, DMSO-D6) δ ppm 4.67 (s, 2H) 7.56 (t, J=7.83 Hz, 1H) 7.63 (dd, J=7.83, 1.01 Hz, 1H) 8.07 (dd, J=7.83, 1.01 Hz, 1H)

Example 4

6-benzyl-1-carboxymethoxy-3,8-dithia-cyclopenta [a]indene-2-carboxylic acid

Step A: Following General Procedure B, 1-tert-butoxycar-bonylmethoxy-6-chloro-3,8-dithia-cyclopenta[a]indene-2-carboxylic acid methyl ester (83 mg, 0.20 mmol), Pd(OAc)$_2$ (4.4 mg), 2-di-tert-butylphosphino biphenyl (14 mg), potassium fluoride (26 mg), and benzyl-9BBN 0.5M in THF (0.45 ml, 1.1 equiv) were used. Work-up and purification by column chromatography yielded 39 mg (41%) of 6-benzyl-1-tert-butoxycarbonylmethoxy-3,8-dithia-cyclopenta[a]in-dene-2-carboxylic acid methyl ester.

Step B, Following General Procedure A: 6-benzyl-1-tert-butoxycarbonylmethoxy-3,8-dithia-cyclopenta[a]indene-2-carboxylic acid methyl ester (37 mg, 0.08 mmol) was stirred for 22 hr. Work-up yielded 18 mg (58%) of the title compound as a yellow solid.

1H NMR (400 MHz, DMSO-D6) δ ppm 4.09 (s, 2H) 4.62-4.70 (br s, 2H) 7.17-7.22 (m, 1H) 7.26-7.31 (m, 4H) 7.37 (d, J=8.08 Hz, 1H) 7.94 (s, 1H) 7.96 (s, 1H).

Example 5

1-Carboxymethoxy-3,8-dithia-cyclopenta[a]indene-2,6-dicarboxylic acid 6-tert-butyl ester Step A: Sulfuric acid conc (5 ml) was added to a solution of 1-methyl 2-nitroterephthalate (25.2 g, 0.112 mmol) in dioxane (120 ml) in a Parr shaker bottle and cooled to 0° C. Isobutene (100 ml) was added, the vessel was sealed, and vigorously shaken for 5 days. The crude product was dissolved in EtOAc after evaporation of the excess isobutene and washed with sat NaHCO$_3$. The organic layer was dried over MgSO$_4$, filtered, and evaporated leaving 23.0 g (73%) of 2-nitroterephthalic acid 4-tert-butyl ester 1-methyl ester as a yellow liquid.

1H NMR (400 MHz, CHLOROFORM-D) δ ppm 1.62 (s, 9H), 3.95 (s, 3H), 7.78 (d, J=8.1 Hz, 1H), 8.26 (dd, J=8.0, 1.6 Hz, 1H), 8.47 (d, J=1.5 Hz, 1H)

Step B: Lithium hydroxide (8.4 g, 0.20 mmol) was added to a 0° C. solution of 2-nitroterephthalic acid 4-tert-butyl ester 1-methyl ester (28.36 g, 0.10 mmol) and methyl thioglycolate (11.6 ml, 0.13 mmol) in DMF (100 ml). After stirring for 18 hr, the orange solution was added to water (400 ml) and acidified with HCl until the pH was 3. The resulting yellow precipitate was filtered and washed with water. After vacuum drying at 50° C., 28.0 g (90%) of 3-hydroxy-benzo[b]thiophene-2,6-dicarboxylic acid 6-tert-butyl ester 2-methyl ester.

1H NMR (400 MHz, CHLOROFORM-D) δ ppm 1.63 (s, 9H), 3.97 (s, 3H), 7.93-7.98 (m, 1H), 7.98-8.02 (m, 1H), 8.39 (s, 1H), 10.08 (s, 1H)

Step C: Trifluoromethanesulfonic anhydride (4.6 ml 27 mmol, 1.5 equiv) was dropwise added to a 0° C. solution of 3-hydroxy-benzo[b]thiophene-2,6-dicarboxylic acid 6-tert-butyl ester 2-methyl ester (5.56 g, 18 mmol) in DCM (50 ml) and Et$_3$N (50 ml). The reaction mixture was warmed to RT and stirred for 30 min. After adding water and EtOAc the crude reaction mixture was washed with sat. NaHCO$_3$ then dried over MgSO$_4$. Filtration, evaporation, and purification by column chromatography yielded 4.56 g (57%) of 3-trif-luoromethanesulfonyloxy-benzo[b]thiophene-2,6-dicar-boxylic acid 6-tert-butyl ester 2-methy ester. 1H NMR (400 MHz, CHLOROFORM-D) δ ppm 1.64 (s, 9H) 4.01 (s, 3H)

7.87 (d, J=8.59 Hz, 1H) 8.12 (dd, J=8.59, 1.52 Hz, 1H) 8.50 (s, 1H). HRMS (ESI+, m/z) calcd for [M+NA]$^{1+}$, 463.01035, found 463.01013.

Step D: Methyl thioglycolate (1.1 ml, 12 mmol) was added to a solution of 3-trifluoromethanesulfonyloxy-benzo[b]thiophene-2,6-dicarboxylic acid 6-tert-butyl ester 2-methy ester in DCM (30 ml) and Et$_3$N (15 ml) and stirred for 24 hr at RT then 24 hr at 40° C. When the starting material was absent in LC trace, water was added. Extraction with EtOAc and evaporation left an orange liquid. Purification by column chromatography yielded 2.7 g (70%) of 3-methoxycarbonyl-methylsulfanyl-benzo[b]thiophene-2,6-dicarboxylic acid 6-tert-butyl ester 2-methyl ester.

Step E: Sodium hydride-60% in oil (0.57 g, 14.1 mmol) was added to 3-methoxycarbonylmethylsulfanyl-benzo[b]thiophene-2,6-dicarboxylic acid 6-tert-butyl ester 2-methyl ester (2.7 g, 6.7 mmol) in DMF (30 ml) and stirred at 90° C. for 2 hr. Water was added to the crude mixture. It was acidified with 1N HCl, extracted with EtOAc, dried over MgSO$_4$, filtered, and the solvent was removed in vacuo. Purification by column chromatography yielded 398 mg (16%) of desired tricyclic compound, 1-hydroxy-3,8-dithia-cyclopenta[a]indene-2,6-dicarboxylic acid 6-tert-butyl ester 2-methyl ester.

1H NMR (400 MHz, DMSO-D6) δ ppm 1.59 (s, 9H) 3.84 (s, 2H) 7.99 (dd, J=8.34, 1.52 Hz, 1H) 8.16 (d, J=8.34 Hz, 1H) 8.70 (s, 1H) 11.25 (s, 1H). HRMS (ESI-, m/z) calcd for [M-H]$^{1-}$, 363.03664, found 363.03587.

Step F: Ethyl bromoacetate (0.17 ml, 1.5 mmol, 1.5 equiv) was added to a mixture of 1-hydroxy-3,8-dithia-cyclopenta[a]indene-2,6-dicarboxylic acid 6-tert-butyl ester 2-methyl ester (364 mg, 1.0 mmol) and K$_2$CO$_3$ in DMF (8 ml) and stirred overnight. Water was added and the mixture was extracted with EtOAc, dried over MgSO$_4$, filtered, and the solvent was removed in vacuo. Vacuum drying left 434 mg (96%) of 1-ethoxycarbonylmethoxy-3,8-dithia-cyclopenta[a]indene-2,6-dicarboxylic acid 6-tert-butyl ester 2-methyl ester.

1H NMR (400 MHz, CHLOROFORM-D) δ ppm 1.29 (t, J=7.20 Hz, 3H) 1.64 (s, 9H) 3.92 (s, 3H) 4.27 (q, J=7.24 Hz, 2H) 5.07 (s, 2H) 7.87 (d, J=8.34 Hz, 1H) 8.06 (dd, J=8.34, 1.26 Hz, 1H) 8.50 (s, 1H). ). HRMS (ESI+, m/z) calcd for [M+H]$^{1+}$, 451.08797, found, 451.08835.

Step G: Following General Procedure A, 1-ethoxycarbonylmethoxy-3,8-dithia-cyclopenta[a]indene-2,6-dicarboxylic acid 6-tert-butyl ester 2-methyl ester (49 mg, 0.11 mmol) was stirred for 3 hr at 40° C. Work-up yielded 40mg (91%) of the title compound as off-white solids.

1H NMR (400 MHz, DMSO-D6) δ ppm 1.59 (s, 9H) 4.75 (s, 2H) 7.98 (dd, J=8.46, 1.39 Hz, 1H) 8.14 (d, J=8.34 Hz, 1H) 8.68 (d, J=1.52 Hz, 1H). HRMS (ESI+, m/z) calcd for [M+H]$^{1+}$, 409.04102, found 409.04180.

Example 6

6-Benzylcarbamoyl-l-carboxymethoxy-3,8-dithia-cyclopenta[a]indene-2-carboxylic acid Step A: 1-Ethoxycarbonylmethoxy-3,8-dithia-cyclopenta[a]indene-2,6-dicarboxylic acid 6-tert-butyl ester 2-methyl ester (1.33 g, 3.0 mmol) was stirred in a solution of TFA (15 ml) and DCM (15 ml) at RT for 17 hr. Removal of solvent by rotory evaporation followed by vacuum quantitatively yielded 1.16 g of 1-ethoxycarbonylmethoxy-3,8-dithia-cyclopenta[a]indene-2,6-dicarboxylic acid 2-methyl ester. 1H NMR (400 MHz, CHLOROFORM-D) δ ppm 1.21 (t, J=7.2 Hz, 3H), 3.86 (s, 3H), 4.18 (q, J=7.1 Hz, 2H), 5.18 (s, 2H), 8.04 (dd, J=8.3, 1.5 Hz, 1H), 8.21 (d, J=8.3 Hz, 1 H), 8.75 (d, J=0.8 Hz, 1H), 13.18 (s, 1H).

Step B: 1-ethoxycarbonylmethoxy-3,8-dithia-cyclopenta[a]indene-2,6-dicarboxylic acid 2-methyl ester (49 mg, 0.13 mmol) and carbonyldiimidazole (25 mg, 0.15 mmol) were dissolved in THF (6 ml). After stirring for 1.5 hr at 60° C., the reaction was cooled to RT. Benzylamine (30 µl, 0.27 mmol, 2.1 equiv) was added and stirred for 3 hr. Removal of solvent followed by column chromatography yielded 9mg (15%) of 6-benzylcarbamoyl-1-ethoxycarbonylmethoxy-3,8-dithia-cyclopenta[a]indene-2-carboxylic acid methyl ester.

1H NMR (400 MHz, CHLOROFORM-D) δ ppm 1.29 (t, J=7.2 Hz, 3H), 3.92 (s, 3H), 4.26 (q, J=7.1 Hz, 2H), 4.69 (d, J=5.6 Hz, 2H), 5.04 (s, 2H), 6.56 (t, J=5.3 Hz, 1 H), 7.28-7.46 (m, 5H), 7.75-7.82 (m, 1H), 7.84-7.91 (m, 1H), 8.33 (s, 1H)

Step C: Following General Procedure A, 6-benzylcarbamoyl-1-ethoxycarbonylmethoxy-3,8-dithia-cyclopenta[a]indene-2-carboxylic acid methyl ester (9 mg, 0.02 mmol) was stirred in THF (1 ml) and water (1 ml) for 17 hr. Work-up yielded 5 mg (63%) of title compounds as a light yellow solid.

1H NMR (400 MHz, DMSO-D6) δ ppm 4.53 (d, J=6.06 Hz, 2H) 4.76 (s, 2H) 7.29-7.22 (m, 1H) 7.40-7.30 (m, 4H) 8.01 (dd, J=8.46, 1.64 Hz, 1H) 8.15 (d, J=8.34 Hz, 1H) 8.62 (d, J=1.01 Hz, 1H) 9.21 (t, J=5.56 Hz, 1H). HRMS (ESI-, m/z) calcd for [M-H]$^{1-}$, 440.02680, found 440.02584.

Example 7

1-Carboxymethoxy-6-cyclohexylcarbamoyl-3,8-dithia-cyclopenta[a]indene-2-carboxylic acid Step B: 1-ethoxycarbonylmethoxy-3,8-dithia-cyclopenta[a]indene-2,6-dicarboxylic acid 2-methyl ester (49 mg, 0.13 mmol) and carbonyldiimidazole (25 mg, 0.15 mmol) were dissolved in THF (6 ml). After stirring for 1.5 hr at 60° C., the reaction was cooled to RT. Cyclohexylamine (25 gl, 0.22 mmol, 1.7 mmol). Stirred for 3 hr. Removal of solvent followed by column chromatography yielded 9mg (15%) of 6-cyclohexylcarbamoyl-1-ethoxycarbonylmethoxy-3,8-dithia-cyclopenta[a]indene-2-carboxylic acid methyl ester.

1H NMR (400 MHz, CHLOROFORM-D) δ ppm 0.74-0.92 (m, 1H), 1.16-1.37 (m, 5H), 1.37-1.54 (m, 2H), 1.59 (s, 1H), 1.63-1.74 (m, 1H), 1.73-1.89 (m, 2H), 1.98-2.14 (m, 2H), 3.92 (s, 3H), 3.95-4.10 (m, I H), 4.27 (q, J=7.2 Hz, 2H), 5.06 (s, 2H), 6.07 (d, J=7.8 Hz, 1H), 7.77 (dd, J=8.3, 1.0 Hz, 1H), 7.82-7.94 (m, 1H), 8.29 (s, 1H)

Step C: Following General Procedure A, 6-cyclohexylcarbamoyl-1-ethoxycarbonylmethoxy-3,8-dithia-cyclopenta[a]indene-2-carboxylic acid methyl ester (9 mg, 0.02 mmol) was stirred in THF (1 ml) and water (1 ml) for 24 hr. Work-up yielded 6 mg (75%) of title compounds as light yellow solids.

1H NMR (400 MHz, DMSO-D6) δ ppm 1.41-1.21 (m, 4H) 1.67-1.57 (m, 1H) 1.80-1.69 (m, 2H) 1.91-1.81 (m, 2H) 3.85-3.72 (m 2H) 4.74 (s, 2H) 7.96 (dd, J=8.34, 1.52 Hz, 1H) 8.11 (d, J=8.34 Hz, 1H) 8.37 (d, J=8.08 Hz, 1H) 8.56 (d, J=1.01 Hz, 1H).

Example 8

1-Carboxymethoxy-6-(cyclohexylmethyl-carbamoyl)-3,8-dithia-cyclopenta[a]indene-2-carboxylic acid Step B: Cyclohexanemethyamine (29 µl, 0.22 mmol) was added to a mixture of 1-ethoxycarbonylmethoxy-3,8-dithia-cyclopenta[a]indene-2,6-dicarboxylic acid 2-methyl ester (42 mg, 0.11 mmol), HATU (49 mg, 0.13 mmol), and Et₃N (50 l) in DMF (0.5 ml). The mixture was stirred for 2 days. Addition of EtOAc, washing with water, drying organic layers over MgSO₄, filtration, and reoval of solvent in vacuo left crude material. Purification by column chromatography yielded 30 mg (58%) of 6-(cyclohexylmethylcarbamoyl)-1-ethoxycarbonylmethoxy-3,8-dithia-cyclopenta[a]indene-2-carboxylic acid methyl ester.

1H NMR (400 MHz, CHLOROFORM-D) δ ppm 0.94-1.12 (m, 2H), 1.16-1.27 (m, 2H), 1.29 (t, J=7.1 Hz, 3H), 1.54 (s, 4H), 1.73-1.87 (m, 4H), 3.36 (t, J=6.4 Hz, 2 H), 3.92 (s, 3H), 4.27 (q, J=7.1 Hz, 2H), 5.06 (s, 2H), 6.22 (t, J=6.1 Hz, 1H), 7.79 (dd, J=8.3, 1.5 Hz, 1H), 7.89 (d, J=8.3 Hz, 1H), 8.31 (d, J=1.0 Hz, 1H)

Step C: Following General Procedure A, 6-(cyclohexylmethylcarbamoyl)-1-ethoxycarbonylmethoxy-3,8-dithia-cyclopenta[a]indene-2-carboxylic acid methyl ester (30 mg, 0.06 mmol) was stirred for 14 hr. Work-up yielded 18 mg (67%) of the title compound as a light yellow solid.

1H NMR (400 MHz, DMSO-D6) δ ppm 1.00-0.89 (m, 2H) 1.25-1.15 (m, 4H) 1.76-1.51 (m, 6H) 3.18-3.12 (m, 2H) 4.62 (s, 2H) 8.11 (d, J=8.34 Hz, 1H) 8.55 (d, J=1.26 Hz, 1H) 8.59 (t, J=5.81 Hz, 1H). HRMS (ESI-, m/z) calcd for [M-H]1−, 446.07375, found, 446.07260.

Example 9

6-tert-Butoxycarbonylamino-1-carboxymethoxy-3,8-dithia-cyclopenta[a]indene-2-carboxylic acid Step A: Diphenylphosphoryl azide (0.85 ml, 3.9 mmol, 1.4 equiv) was added to a mixture of 1-carboxymethoxy-3,8-dithia-cyclopenta[a]indene-2,6-dicarboxylic acid (1.11 g, 2.8 mmol), Et₃N (0.8 ml), toluene (18 ml), and t-BuOH (1.8 ml) and stirred at 100° C. for 18 hr. Removal of solvent and purification by column chromatography yielded 770 mg (59%) of 6-tert-butoxycarbonylamino-1-ethoxycarbonylmethoxy-3,8-dithia-cyclopenta[a]indene-2-carboxylic acid methyl ester.

1H NMR (400 MHz, CHLOROFORM-D) δ ppm 1.29 (t, J=7.07 Hz, 3H) 1.56 (s, 9H) 3.90 (s, 3H) 4.27 (q, J=7.07 Hz, 2H) 5.04 (s, 2H) 6.67 (s, 1H) 7.19 (dd, J=8.84, 2.02 Hz, 1H) 7.73 (d, J=8.08 Hz, 1H) 8.18 (s, 1H). HRMS (ESI+, m/z) calcd for [M+H]$^{1+}$, 466.09887, found, 466.09851.

Step B: Following General Procedure A, 6-tert-Butoxycarbonylamino-1-ethoxycarbonylmethoxy-3,8-dithia-cyclopenta[a]indene-2-carboxylic acid methyl ester (45 mg, 0.1 mmol) was stirred at 40° C. for 1hr. Work-up yielded 36 mg (88%) of the title compound as a white solid.

1H NMR (400 MHz, DMSO-D6) δ ppm 1.50 (s, 9H) 4.57 (s, 2H) 7.48 (d, J=8.84 Hz, 1H) 7.90 (d, J=8.59 Hz, 1H) 8.24 (s, 1H) 9.71 (s, 1H). HRMS (ESI+, m/z) calcd for [M+H]$^{1+}$, 424.05192, found, 424.05109.

Example 10

6-Benzylamino-1-carboxymethoxy-3,8-dithia-cyclopenta[a]indene-2-carboxylic acid

Step A: 6-tert-Butoxycarbonylamino-1-ethoxycarbonylmethoxy-3,8-dithia-cyclopenta[a]indene-2-carboxylic acid methyl ester (684 mg, 1.5 mmol) was stirred in TFA (12 ml) and DCM (15 ml) for 3 hr. Removal of solvent by rotory evaporation yielded 729 mg (quantitative) of 1-ethoxycarbonylmethoxy-2-methoxycarbonyl-3,8-dithia-cyclopenta[a]inden-6-yl-ammonium trifluoroacetate.

1H NMR (400 MHz, DMSO-D6) δ ppm 1.21 (t, J=7.2 Hz, 3H), 3.79 (s, 3H), 4.17 (q, J=7.1 Hz, 2H), 5.10 (s, 2H), 6.83 (dd, J=8.6, 1.8 Hz, 1H), 7.13 (d, J=1.8 Hz, 1 H), 7.74 (d, J=8.6 Hz, 1H)

Step B: Sodium triacetoxyborohydride (90 mg, 0.42 mmol, 2.5 equiv) was added to a mixture of 1-ethoxycarbonylmethoxy-2-methoxycarbonyl-3,8-dithia-cyclopenta[a]inden-6-yl-ammonium trifluoroacetate (82 mg, 0.17 mmol), benzaldehyde (21 mg, 0.2 mmol, 1.2 equiv), and acetic acid (5wl) in DCE (4 ml). The reaction mixture was stirred at RT for 16 hr then DCM (20 ml) was added. The mixture was washed with sat. NaHCO₃, dried over MgSO₄, filtered, and the solvent was removed in vacuo. Purification by column chromatography yielded 61 mg (81%) of 6-benzylamino-1-ethoxycarbonylmethoxy-3,8-dithia-cyclopenta[a]indene-2-carboxylic acid methyl ester.

1H NMR (400 MHz, CHLOROFORM-D) δ ppm 1.28 (t, J=7.1 Hz, 3H), 3.88 (s, 3H), 4.26 (q, J=7.1 Hz, 2H), 4.41 (s, 2H), 5.01 (s, 2H), 6.75 (dd, J=8.6, 2.3 Hz, 1H), 6.96 (d, J=2.0 Hz, 1H), 7.28-7.42 (m, 5H), 7.61 (d, J=8.6 Hz, 1H).

Step C: Following General Procedure A, 6-benzylamino-1-ethoxycarbonylmethoxy-3,8-dithia-cyclopenta[a]indene-2-carboxylic acid methyl ester (61 mg, 0.13 mmol) was stirred overnight at RT then heated to 40° C. for 4 hr. Work-up yielded 38 mg (69%) of the title compound as a yellow solid.

1H NMR (400 MHz, DMSO-D6) δ ppm 4.36 (d, J=5.81 Hz, 2H) 4.52 (s, 2H) 6.82-6.76 (m, 1H) 6.85 (dd, J=8.72, 2.15 Hz, 1H) 7.08 (d, J=2.27 Hz, 1H) 7.24 (t, J=6.82 Hz, 1H) 7.36-7.30 (m, 2H) 7.42-7.37 (m, 2H) 7.67 (d, J=8.59 Hz, 1H). HRMS (ESI+, m/z) calcd for [M+H]$^{1+}$, 414.04644, found, 414.04668.

Example 11

1-Carboxymethoxy-6-(tetrahydropyran-4-ylamino)-3,8-dithia-cyclopenta[a]indene-2-carboxylic acid Step B: Sodium triacetoxyborohydride (90 mg, 0.42 mmol, 2.5 equiv) was added to a mixture of 1-ethoxycarbonylmethoxy-2-methoxycarbonyl-3,8-dithia-cyclopenta[a]inden-6-yl-ammonium trifluoroacetate (85 mg, 0.17 mmol), tetrahydropyran-4-one (24 μl, 0.2 mmol, 1.2 equiv), and acetic acid (5 μl) in DCE (4 ml) and stirred at 50° C. for 17 hr. DCM (20 ml) was added and the mixture was washed with sat. NaHCO₃, dried over MgSO₄, filtered, and the solvent was reoved in vacuo. Purification by column chromatography yielded 72 mg (94%) of 1-ethoxycarbonylmethoxy-6-(tetrahydropyran-4-ylamino)-3,8-dithiacyclopenta[a]indene-2-carboxylic acid methyl ester.

1H NMR (400 MHz, CHLOROFORM-D) δ ppm 1.29 (t, J=7.2 Hz, 3H), 1.44-1.61 (m, 3H), 2.08 (d, J=14.4 Hz, 2H), 3.44-3.70 (m, 3H), 3.88 (s, 3H), 3.98-4.09 (m, 2H), 4.27 (q, J=7.2 Hz, 2H), 5.02 (s, 2H), 6.71 (dd, J=8.6, 1.8 Hz, 1H), 6.96 (s, 1 H), 7.61 (d, J=8.6 Hz, 1H).

Step C: Following General Procedure A, 1-ethoxycarbonylmethoxy-6-(tetrahydropyran-4-ylamino)-3,8-dithiacyclopenta[a]indene-2-carboxylic acid methyl ester (72 mg, 0.16 mmol) was stirred for 3 hr. Work-up yielded 65 mg (77%) of the title compound.

1H NMR (400 MHz, DMSO-D6) δ ppm 1.46-1.92 (m, 2H) 1.92 (d, J=13.39 Hz, 2H) 3.88 (m, J=11.12 Hz, 1H) 4.83 (s, 1H) 6.18 (d, J=7.83 Hz, 1H) 6.82 (dd, J=8.84, 2.02 Hz, 1H)

7.15 (d, J=2.02 Hz, 1H) 7.68 (d, J=8.84 Hz, 1H). HRMS (ESI+, m/z) calcd for [M+H]$^{1+}$, 408.05701, found 408.05609.

Example 12

4-(2-Carboxy-1-carboxymethoxy-3,8-dithia-cyclopenta[a]inden-6-ylamino)-piperidine-1-carboxylic acid tert-butyl ester Step B: Sodium triacetoxyborohydride (227 mg, 1.07 mmol, 2.5 equiv) was added to a mixture of 1-ethoxycarbonylmethoxy-2-methoxycarbonyl-3,8-dithia-cyclopenta[a]inden-6-yl-ammonium trifluoroacetate (85 mg, 0.17 mmol), 4-oxopiperidine-1-carboxylic acid tert-butyl ester (129 mg, 0.65 mmol, 1.2 equiv), and acetic acid (5 µl) in DCE (4 ml) and stirred at 50° C. for 17 hr. DCM (20 ml) was added and the mixture was washed with sat. NaHCO$_3$, dried over MgSO$_4$, filtered, and rotovaped. Purification by column chromatography yielded 237 mg (quantitative) of 4-(1-tert-butoxycarbonylmethoxy-2-methoxycarbonyl-3,8-dithiacyclopenta[a]inden-6-ylamino)-piperidine-1-carboxylic acid tert-butyl ester.

1H NMR (400 MHz, CHLOROFORM-D) δ ppm 1.29 (t, J=7.2 Hz, 3H), 1.34-1.44 (m, 2H), 1.47 (s, 9H), 1.79-1.91 (m, 1H), 2.08 (d, J=12.1 Hz, 2H), 2.87-3.10 (m, 3H), 3.43-3.58 (m, 1H), 3.78-3.94 (m, 5H), 4.00-4.16 (m, 2H), 4.26 (q, J=7.1 Hz, 2H), 5.02 (s, 2H), 6.69 (dd, J=8.6, 2.0 Hz, 1H), 6.94 (d, J=2.0 Hz, 1H), 7.60 (d, J=8.6 Hz, 1H)

Step C: Following General Procedure A, 4-(1-tert-butoxycarbonylmethoxy-2-methoxycarbonyl-3,8-dithiacyclopenta[a]inden-6-ylamino)-piperidine-1-carboxylic acid tert-butyl ester (38 mg, 0.07 mmol) was stirred for 2 hr at 40° C. followed by 16 hr at RT. Work-up yielded 4 mg (11%) of the title compound.

1H NMR (400 MHz, DMSO-D6) δ ppm 1.31-1.19 (m, 2H) 1.41 (s, 9H) 1.93 (d, J=12.88 Hz, 2H) 2.93 (s, 2H) 3.52 (s, 1H) 3.90 (d, J=12.88 Hz, 2H) 4.90 (s, 2H) 6.17 (d, J=8.08 Hz, 1H) 6.80 (dd, J=8.84, 2.27 Hz, 1H) 7.14 (d, J=2.27 Hz, 1H) 7.69 (d, J=8.84 Hz, 1H).

Example 13

1-Carboxymethoxy-6-(1-phenylmethanesulfonyl-piperidin-4-ylamino)-3,8-dithia-cyclopenta[a]indene-2-carboxylic acid Step A: 1-Ethoxycarbonylmethoxy-2-methoxycarbonyl-3,8-dithia-cyclopenta[a]inden-6-yl-ammonium trifluoroacetate (204 mg, 0.37 mmol) was stirred in a mixture of TFA (10 ml) and DCM (10 ml). Evaporation of solvent left crude material (206 mg).

1H NMR (400 MHz, DMSO-D6) δ ppm 1.21 (t, J=7.1 Hz, 2H), 1.50-1.64 (m, 2H), 2.04-2.15 (m, 2H), 2.96-3.09 (m, 2H), 3.11-3.23 (m, 1H), 3.28-3.40 (m, 2H), 3.57-3.68 (m, 1H), 3.79 (s, 2H), 4.17 (q, J=7.1 Hz, 2H), 5.11 (s, 2H), 6.84 (dd, J=8.8, 2.0 Hz, 1H), 7.17 (d, J=2.0 Hz, 1H), 7.75 (d, J=8.6 Hz, 1H), 8.22-8.54 (m, 2H).

Step B: The crude material (65 mg, 0.12 mmol) was treated with α-tolylsulfonyl chloride (23 mg, 0.12 mmol) in a mixture of DCM (2 ml) and sat. NaHCO$_3$ (2 ml). When LC indicated absence of starting material, DCM was added and the mixture was extracted with water. The organic layers were combined, dried over MgSO$_4$, filtered, and removal of the solvent in vacuo afforded 37 mg (53% two steps) of 1-ethoxycarbonylmethoxy-6-(1-phenylmethanesulfonyl-piperidin-4-ylamino)-3,8-dithia-cyclopenta[a]indene-2-carboxylic acid methyl ester as a green solid.

1H NMR (400 MHz, CHLOROFORM-D) δ ppm 1.29 (t, J=7.2 Hz, 3H), 1.35-1.50 (m, 2H), 1.99-2.12 (m, J=13.4 Hz, 2H), 2.71-2.86 (m, 2H), 3.33-3.47 (m, 1H), 3.59-3.69 (m, 2H), 3.74-3.82 (m, J=8.6 Hz, 1H), 3.88 (s, 3H), 4.21-4.31 (m, 4H), 5.02 (s, 2H), 6.66 (dd, J=8.7, 2.1 Hz, 1H), 6.89 (d, J=2.3 Hz, 1H), 7.37-7.46 (m, 5H), 7.60 (d, J=8.6 Hz, 1H).

Step C: Following General Procedure A, 6-(1-benzyl-piperidin-4-ylamino)-1-tert-butoxycarbonylmethoxy-3,8-dithia-cyclopenta[a]indene-2-carboxylic acid methyl ester (37 mg, 0.06 mmol) was stirred for 20 hr at 40° C. Work-up yielded 22mg (65%) of the title compound as a green solid.

1H NMR (400 MHz, DMSO-D6) δ ppm 1.24 (s, 1H) 1.43-1.29 (m, 2H) 1.96 (s, 1H) 2.92 (t, J=10.74 Hz, 2H) 3.55 (d, J=12.38 Hz, 1H) 4.42 (s, 2H) 4.56 (s, 2H) 6.14 (d, J=8.08 Hz, 1H) 6.80 (dd, J=8.59, 2.02 Hz, 1H) 7.15 (d, J=1.77 Hz, 1H) 7.45-7.36 (m, 5H) 7.67 (d, J=8.59 Hz, 1H). HRMS (ESI+, m/z) calcd for [M+H]$^{1+}$, 561.08184, found, 561.08092.

Example 14

1-Carboxymethoxy-6-(1-ethanesulfonylpiperidin-4-ylamino)-3,8-dithia-cyclopenta[a]indene-2-carboxylic acid Step B: The crude material (83 mg, 0.15 mmol) was treated with ethysulfonyl chloride (14 µl, 0.15 mmol) in a mixture of DCM (3 ml) and sat. NaHCO$_3$ (2 ml). When LC indicated absence of starting material, DCM was added and the mixture was extracted with water. The organic layers were combined, dried over MgSO$_4$, filtered, and the solvent was removed in vacuo leaving 58 mg (73% over two steps) of 6-(1-ethanesulfonyl-piperidin-4-ylamino)-1-ethoxycarbonylmethoxy-3,8-dithia-cyclopenta[a]indene-2-carboxylic acid methyl ester as green film.

1H NMR (400 MHz, CHLOROFORM-D) δ ppm 1.29 (t, J=7.1 Hz, 3H), 1.39 (t, J=7.5 Hz, 3H), 1.56-1.65 (m, 3H), 2.15-2.28 (m, J=12.3, 2.9 Hz, 2H), 2.94-3.09 (m, 4H), 3.44-3.59 (m, 1H), 3.79-3.86 (m, 2H), 3.88 (s, 3H), 4.26 (q, J=7.1 Hz, 2H), 5.02 (s, 2H), 6.70 (dd, J=8.6, 2.0 Hz, 1H), 6.94 (d, J=2.0 Hz, 1H), 7.62 (d, J=8.6 Hz, 1 H).

Step C: Followng General Procedure A, 6-(1-ethanesulfonyl-piperidin-4-ylamino)-1-ethoxycarbonylmethoxy-3,8-dithia-cyclopenta[a]indene-2-carboxylic acid methyl ester (58 mg, 0.11 mmol) was stirred for 16 hr. Work-up yielded 38 mg (72%) of the title compound as a golden yellow solid.

1H NMR (400 MHz, DMSO-D6) δ ppm 1.23 (t, J=7.33 Hz, 3H) 1.48-1.35 (m, 2 H) 2.06-1.97 (m, 2H) 3.05-2.96 (m, 2H) 3.07 (q, J=7.41 Hz, 2H) 3.60 (d, J=12.63 Hz, 2 H) 4.55-4.31 (m, 2H) 6.20-5.95 (m, 2H) 6.80 (d, J=8.84 Hz, 1H) 7.14 (s, 1H) 7.73-7.56(m, 1H).

Example 15

3-Carboxymethoxy-naphtho[1,2-b]thiophene-2-carboxylic acid

Step A: To an oven-dried 50 mL round bottom flask under a nitrogen atmosphere was added 1-bromo-naphthalene-2-carboxylic acid ethyl ester (0.244 g, 0.88 mmol), methyl thioacetate (0.08 mL, 0.88 mmol), 20 mL DMF, then sodium hydride (0.075 g of a 60% suspension in mineral oil, 1.84 mmol). The resulting mixture was allowed to stir for 16 hours. 25 mL of 1.2 N HCl was then added, at which point a precipitate formed. The solids were collected by filtration and dried in vacuo. 3-hydroxy-naphtho[1,2-b]thiophene-2-carboxylic acid methyl ester was isolated as an off white solid (0.134 g, 60%).

1H NMR (400 MHz, CHLOROFORM-D) δ ppm 3.99 (s, 3H) 7.61 (m, 2H) 7.75 (d, J=8.59 Hz, 1H) 7.87 (d, J=8.84 Hz, 1H) 7.94 (dd, J=6.06, 3.54 Hz, 1H) 8.10 (dd, J=6.06, 3.28 Hz, 1H) 10.12 (s, 1H).

Step B: To an oven-dried 50 mL round bottom flask under a nitrogen atmosphere was added 3-hydroxy-naphtho[1,2-b]thiophene-2-carboxylic acid methyl ester (0.134 g, 052 mmol), ethyl bromoacetate (0.06 mL, 052 mmol), potassium carbonate (0.072 g, 052 mmol) and 20 mL DMF. The resulting mixture was allowed to stir for 16 hours at room temperature. 30 mL water was added to the mixture, at which point a precipitate formed. The solids were collected by filtration and dried in vacuo. 3-ethoxycarbonylmethoxy-naphtho[1,2-b]thiophene-2-carboxylic acid methyl ester was isolated as a white solid (0.116 g, 65%).

1H NMR (400 MHz, CHLOROFORM-D) δ ppm 1.28 (t, J=7.20 Hz, 3H) 3.95 (m, 3H) 4.26 (q, J=7.16 Hz, 2H) 5.07 (in, 2H) 7.58 (in, 2H) 7.76 (m, 1H) 7.93 (m, 1 H) 8.02 (mn, 1H) 8.11 (m, 1H).

Step C: To a 25 mL round bottom flask added 3-ethoxycarbonylmethoxy-naphtho[1,2-b]thiophene-2-carboxylic acid methyl ester (0.116 g, 0.34 mmol) and 5 mL THF. To this mixture added a solution of lithium hydroxide hydrate (0.057 g, 1.35 mmol) in 3 mL water. This mixture was allowed to stir at room temperature for 16 hours. At this time 15 mL 1.2 N HCl was added, and a precipitate formed. The solids were collected by filtration and dried in vacuo. 3-carboxymethoxy-naphtho[1,2-b]thiophene-2-carboxylic acid was isolated as a tan solid (0.096 g, 93%). 1H NMR (400 MHz, DMSO-D6) δ ppm 5.06 (s, 2H) 7.69 (m, 2H) 7.91 (d, J=8.84 Hz, 1H) 7.95 (m, 1H) 8.08 (m, 1 H) 8.19 (t, J=4.0 Hz, 1H).

Example 16

3-Carboxymethoxy-thieno[3,2-c]guinoline-2-carboxylic acid

3-Hydroxy-thieno[3,2-c]quinoline-2-carboxylic acid methyl ester as a tan solid (0.084 g, 38%) was obtained following a procedure similar to Example 15, step A.

1H NMR (400 MHz, DMSO-D6) δ ppm 3.89 (s, 3H) 7.75 (m, 1H) 7.87 (mn, 1H) 8.17 (d, J=7.83 Hz, 1H) 8.24 (d, J=7.33 Hz, 1H) 9.29 (s, 1H) 11.18 (s, 1H).

3-Ethoxycarbonylmethoxy-thieno[3,2-c]quinoline-2-carboxylic acid methyl ester as a white solid (0.051 g, 46%) was obtained following a procedure similar to Example 15, step B.

1H NMR (400 MHz, DMSO-D6) δ ppm 1.18 (t, J=7.07 Hz, 3H) 3.91 (s, 3H) 4.15 (q, J=7.07 Hz, 2H) 5.22 (s, 2H) 7.77 (m, J=15.66 Hz, 1H) 7.90 (m, 1H) 8.20 (d, J=7.83 Hz, 1H) 8.30 (d, J=8.08 Hz, 1H) 9.34 (s, 1H).

3-Carboxymethoxy-thieno[3,2-c]quinoline-2-carboxylic acid as a white solid (0.022 g, 48%) was obtained following a procedure similar to Example 15, step C.

1H NMR (400 MHz, DMSO-D6) δ ppm 5.15 (s, 2H) 7.83 (m, 2H) 8.23 (dd, J=37.90, 8.08 Hz, 2H) 9.32 (s, 1H).

Example 17

3-Carboxymethoxy-6-methoxy-thieno[3,2-c]guinoline-2-carboxylic acid

3-Hydroxy-6-methoxy-thieno[3,2-c]quinoline-2-carboxylic acid methyl ester was obtained following a procedure similar to Example 15, step A, as a greenish solid (0.196 g, 80%).

1H NMR (400 MHz, DMSO-D6) δ ppm 3.90 (s, 3H) 4.07 (s, 3H) 7.47 (d, J=7.07 Hz, 1H) 7.77 (t, J=7.96 Hz, 1H) 7.84 (m, 1H) 9.43 (s, 1H).

3-Ethoxycarbonylmethoxy-6-methoxy-thieno[3,2-c]quinoline-2-carboxylic acid methyl ester was obtained following a procedure similar to Example 15, step B, as a white solid (0.048 g, 20%).

1H NMR (400 MHz, DMSO-D6) δ ppm 2.50 (m, 3H) 3.90 (s, 3H) 4.01 (s, 3H) 4.15 (q, J=7.16 Hz, 2H) 5.22 (s, 2H) 7.36 (dd, J=7.83, 1.01 Hz, 1H) 7.69 (t, J=8.08 Hz, 1H) 7.78 (m, 1H) 9.27 (s, 1H).

3-Carboxymethoxy-6-methoxy-thieno[3,2-c]quinoline-2-carboxylic acid was obtained following a procedure similar to Example 15, step C, as a white solid (0.019 g, 46%).

1H NMR (400 MHz, DMSO-D6) δ ppm 4.01 (s, 3H) 5.15 (s, 2H) 7.34 (dd, J=8.08, 1.26 Hz, 1H) 7.67 (t, J=7.96 Hz, 1H) 7.76 (m, 1H) 9.25 (s, 1H).

Example 18

3-Carboxymethoxy-thieno[3,2-h]quinoline-2-carboxylic acid

3-Hydroxy-thieno[3,2-h]quinoline-2-carboxylic acid methyl ester was obtained following a procedure similar to Example 15, step A, as a pink solid (0.115 g, 75%).

1H NMR (400 MHz, CHLOROFORM-D) δ ppm 4.01 (s, 3H) 7.55 (dd, J=8.21, 4.42 Hz, 1H) 7.72 (d, J=8.59 Hz, 1H) 7.95 (d, J=8.59 Hz, 1H) 8.25 (dd, J=8.21, 1.64 Hz, 1H) 8.95 (dd, J=4.42, 1.64 Hz, 1H) 10.15 (s, 1H).

3-tert-Butoxycarbonylmethoxy-thieno[3,2-h]quinoline-2-carboxylic acid methyl ester was obtained following a procedure similar to Example 15, step B, as a tan solid (0.130 g, 79%).

1H NMR (400 MHz, DMSO-D6) δ ppm 1.39 (s, 9H) 3.90 (s, 3H) 5.04 (s, 2H) 7.73 (dd, J=8.21, 4.42 Hz, 1H) 7.98 (d, J=8.84 Hz, 1H) 8.06 (m, 1H) 8.55 (dd, J=8.21, 1.64 Hz, 1H) 8.99 (dd, J=4.42, 1.64 Hz, 1H).

3-Carboxymethoxy-thieno[3,2-h]quinoline-2-carboxylic acid was obtained following a procedure similar to Example 15, step C, as a white solid (0.039 g, 80%).

1H NMR (400 MHz, DMSO-D6) δ ppm 5.06 (s, 2H) 7.72 (dd, J=8.08, 4.29 Hz, 1 H) 7.95 (d, J=8.84 Hz, 1H) 8.04 (m, 1H) 8.53 (dd, J=8.34, 1.52 Hz, 1H) 8.98 (dd, J=4.29, 1.77 Hz, 1H).

Example 19

3-Carboxymethoxy-8-methyl-thieno[3,2-c]quinoline-2-carboxylic acid

3-Hydroxy-8-methyl-thieno[3,2-c]quinoline-2-carboxylic acid methyl ester was obtained following a procedure similar to Example 15, step A, as a green solid (0.215 g, 98%).

1H NMR (400 MHz, DMSO-D6) δ ppm 2.60 (s, 3H) 3.90 (s, 3H) 7.85 (dd, J=8.59, 1.77 Hz, 1H) 8.19 (m, 2H) 9.58 (s, 1H).

3-tert-Butoxycarbonylmethoxy-8-methyl-thieno[3,2-c]quinoline-2-carboxylic acid methyl ester was obtained following a procedure similar to Example 15, step B, as a tan solid (0.207 g, 68%).

1H NMR (400 MHz, DMSO-D6) δ ppm 1.38 (s, 9H) 2.57 (s, 3H) 3.90 (s, 3H) 5.10 (s, 2H) 7.71 (dd, J=8.84, 1.77 Hz, 1H) 8.07 (m, 2H) 9.26 (s, 1H).

3-Carboxymethoxy-8-methyl-thieno[3,2-c]quinoline-2-carboxylic acid was obtained following a procedure similar to Example 15, step C, as a white solid (0.041 g, 86%).

1H NMR (400 MHz, DMSO-D6) δ ppm 2.57 (s, 3H) 5.14 (s, 2H) 7.70 (dd, J=8.72, 1.64 Hz, 1H) 8.06 (m, 2H) 9.25 (s, 1H).

Example 20

3-Carboxymethoxy-6,8-dimethyl-thieno[3,2-c]quinoline-2-carboxylic acid

3-Hydroxy-6,8-dimethyl-thieno[3,2-c]quinoline-2-carboxylic acid methyl ester was obtained following a procedure similar to Example 15, step A, as an orange solid (0.221 g, 96%).

1H NMR (400 MHz, DMSO-D6) δ ppm 2.52 (s, 3H) 2.75 (s, 3H) 3.89 (s, 3H) 7.59 (s, 1H) 7.84 (s, 1H) 9.27 (s, 1H).

3-tert-Butoxycarbonylmethoxy-6,8-dimethyl-thieno[3,2-c]quinoline-2-carboxylic acid methyl ester was obtained following a procedure similar to Example 15, step B, as a gray solid (0.179 g, 58%).

1H NMR (400 MHz, DMSO-D6) δ ppm 1.38 (s, 9H) 2.52 (s, 3H) 2.75 (s, 3H) 3.90 (s, 3H) 5.10 (s, 2H) 7.59 (s, 1H) 7.87 (s, 1H) 9.27 (s, 1H).

3-Carboxymethoxy-6,8-dimethyl-thieno[3,2-c]quinoline-2-carboxylic acid was obtained following a procedure similar to Example 15, step C, as a white solid (0.042 g, 85%).

1H NMR (400 MHz, DMSO-D6) δ ppm 2.52 (s, 3H) 2.75 (s, 3H) 5.14 (s, 2H) 7.57 (s, 1H) 7.85 (s, 1H) 9.26 (s, 1H).

Example 21

1-Carboxymethoxy-6-cyclohexylamino-3,8-dithia-cyclopenta[a]indene-2-carboxylic acid Step A: To a solution of 3-hydroxy-benzo[b]thiophene-2,6-dicarboxylic acid 6-allyl ester 2-methyl ester (3.2 g, 10.95 mmol) in DCM (50 mL) was added TEA (1.83 mL, 13.14 mmol), Tf$_2$O (2.2 mL, 13.14 mL) and DMAP (67 mg, 0.55 mmol) at 0° C. The temperature was allowed to rise to room temperature and the resultant mixture was stirred for 4 hours, washed with aq. NaHCO3 and dried over MgSO4. The crude product was purified on CombiFlash column eluted with hexanes/EtOAc to give desire product, 3-trifluoromethanesulfonyloxy-benzo[b]thiophene-2,6-dicarboxylic acid 6-allyl ester 2-methyl ester as a white solid (3.88g, 84%).

1H NMR (400 MHz, CHLOROFORM-D) δ ppm 4.02 (s, 3H) 4.86-4.93 (m, 2 H) 5.34 (dd, J=10.48, 1.14 Hz, 1H) 5.41-5.50 (m, J=17.18, 1.52 Hz, 1H) 5.98-6.15 (m, 1H) 7.90 (d, J=8.59 Hz, 1H) 8.19 (dd, J=8.72, 1.39 Hz, 1H) 8.59 (s, 1H).

Step B: To a solution of 3-trifluoromethanesulfonyloxy-benzo[b]thiophene-2,6-dicarboxylic acid 6-allyl ester 2-methyl ester (3.8 g, 8.96 mmol) in DCM was added methyl thioglycoate (0.96 mL, 10.75 mmol) and TEA (3.75 mL, 26.88 miL) at 0° C. The temperature was allowed to rise to room temperature. The mixture was stirred for 24 hours and washed with aq. NaHCO3, dried over MgSO4 and purified on CombiFlash column eluted with hexanes/EtOAc to give the desired compound, 3-methoxycarbonylmethylsulfanyl-benzo[b]thiophene-2,6-dicarboxylic acid 6-allyl ester 2-methyl ester (1.81g, 53%) as a light yellow solid.

1H NMR (400 MHz, CHLOROFORM-D) δ ppm 3.51 (s, 3H) 4.00 (s, 3H) 4.84-4.96 (m, 2H) 5.28-5.39 (m, 1H) 5.39-5.51 (m, 1H) 5.96-6.21 (m, 1H) 8.15 (dd, J=8.59, 1.52 Hz, 1H) 8.25 (dd, J=8.59, 0.76 Hz, 1H) 8.59 (dd, J=1.52, 0.76 Hz, 1H).

Step C: To a solution of 3-methoxycarbonylmethylsulfanyl-benzo[b]thiophene-2,6-dicarboxylic acid 6-allyl ester 2-methyl ester (1.05 g, 2.76 mmol) in DMF was added DBU (0.83 mL, 5.53 mmoL) at room temperature. The resultant mixture was stirred for 24 hours. To this was added ethyl bromoacetate (0.92 mL, 8.28 mmoL) and K$_2$CO$_3$ (1.14 g, 8.26 mmoL). The reaction mixture was stirred for additional 2 hours, then aq. NH$_4$Cl (200 mL and water (300 mL) was added. The white precipate was collected by filtration and washed with water to give the desired compound, 1-ethoxycarbonylmethoxy-3,8-dithia-cyclopenta[a]indene-2,6-dicarboxylic acid 6-allyl ester 2-methyl ester (1.162 g, 97% overall).

1H NMR (400 MHz, CHLOROFORM-D) δ ppm 1.29 (t, J=7.07 Hz, 3H) 4.27 (q, J=7.24 Hz, 2H) 4.85-4.92 (m, 2H) 5.07 (s, 2H) 5.30-5.38 (m, 1H) 5.40-5.51 (m, 1 H) 5.97-6.17 (m, 1H) 7.91 (d, J=7.83 Hz, 1H) 8.13 (dd, J=8.46, 1.39 Hz, 1H) 8.59 (d, J=1.52 Hz, 1H).

Step D: To a suspension of 1-ethoxycarbonylmethoxy-3,8-dithia-cyclopenta[a]indene-2,6-dicarboxylic acid 6-allyl ester 2-methyl ester (920 mg, 2.12 mmol) in THF (50 mL) was added Pd(PPh$_3$)$_4$ (240.4 mg, 0.21 mmol) under N$_2$, followed by addition of HOAc (5 mL). The resultant mixture was stirred at room temperature for 2 hours, diluted with hexanes/EtOAc (4:1), and the precipate was collected by filtration to give the desired product, 1-ethoxycarbonylmethoxy-3,8-dithia-cyclopenta[a]indene-2,6-dicarboxylic acid 2-methyl ester, as a white solid (779 mg, 93%).

1H NMR (400 MHz, DMSO-D6) δ ppm 1.22 (t, J=7.07 Hz, 4H) 3.87 (s, 3H) 4.19 (q, J=7.07 Hz, 2H) 5.19 (s, 2H) 8.05 (dd, J=8.34, 1.52 Hz, 1H) 8.19-8.26 (m, 1 H) 8.75 (dd, J=1.52, 0.76 Hz, 1H) 13.25 (s, 1H).

Step E: To a solution of 1-ethoxycarbonylmethoxy-3,8-dithia-cyclopenta[a]indene-2,6-dicarboxylic acid 2-methyl ester (290 mg, 0.73 mmol) in toluene (5 mL) and t-BuOH (0.5 mL) was added DPPA (0.238 mL, 1.10 mmol) and TEA (0.205 mL) at room temperature. The reaction mixture was stirred for 30 min, extra 0.5 mL of t-BuOH was added, and the reaction mixture was heated to 100° C. After stirring at this temperature overnight, the mixture was partitioned between DCM and water and extracted with DCM, dried over MgSO4. The crude product was purified on CombiFlash column eluted with DCM/EtOAc to give the desired product, 6-tert-butoxycarbonylamino-1-ethoxycarbonylmethoxy-3,8-dithia-cyclopenta[a]indene-2-carboxylic acid methyl ester (195 mg, 57%).

1H NMR (400 MHz, CHLOROFORM-D) δ ppm 1.29 (t, J=7.20 Hz, 3H) 1.54 (s, 9H) 3.90 (s, 3H) 4.27 (q, J=7.07 Hz, 2H) 5.04 (s, 2H) 6.72 (s, 1H) 7.19 (dd, J=8.84, 2.02 Hz, 1H) 7.71 (d, J=8.59 Hz, 1H) 8.17 (s, 1H).

Step F: To a solution of 6-tert-butoxycarbonylamino-1-ethoxycarbonylmethoxy-3,8-dithia-cyclopenta[a]indene-2-carboxylic acid methyl ester (466 mg, 1.0 mmol) in DCM (15 mL) was added TFA (2 mL). The resultant mixture was stirred at room temperature for 2 hours. The solvent was removed under vacuumn. The crude product was redissolved in DCM (10 mL). To this was added cyclohexanone (0.156 mL, 1.5 mmoL) and HOAc (0.088 mL, 1.5 mmol), followed by addition of NaBH(OAc)3 (424 mg, 2.0 mmol). The resultant mixture was stirred at room temperature overnight before directly loaded onto a CombiFlash column, eluted with hexanes/EtOAc togive the desired product, 6-cyclohexylamino-1-ethoxycarbonylmethoxy-3,8-dithia-cyclopenta[a]indene-2-carboxylic acid methyl ester (260mg, 65%).

1H NMR (400 MHz, CHLOROFORM-D) δ ppm 1.10-1.26 (m, 2H) 1.33-1.48 (m, 2H) 1.61-1.95 (m, 4H) 2.09 (dd, J=12.88, 3.28 Hz, 2H) 3.26-3.41 (m, 1H) 3.88 (s, 3H) 4.26 (q, J=7.07 Hz, 2H) 5.02 (s, 2H) 6.66 (dd, J=8.72, 2.15 Hz, 1H) 6.91 (d, J=2.27 Hz, 1H) 7.57 (d, J=8.34 Hz, 1H).

Step G: To a solution of 6-cyclohexylamino-1-ethoxycarbonylmethoxy-3,8-dithia-cyclopenta[a]indene-2-carboxylic acid methyl ester (23 mg, 0.05 mmol) in THF/H20 was added 2.OM LiOH solution (0.125 mL, 0.25 mmol) at room temperature. After stirring at this tempterature overnight, the reaction mixture was concentrated, and acidified with 10% HCl. The product was collected by filtration and washed with water as a white solid (13.2 mg, 63%).

1H NMR (400 MHz, DMSO-D6) δ ppm 0.84-1.12 (m, 4H) 1.11-1.31 (m, 2H) 1.40-1.50 (m, 1H) 1.51-1.65 (m, 2H) 1.80 (dd, J=13.14, 3.03 Hz, 2H) 4.18 (s, 2H) 5.67 (d, J=7.83 Hz, 2H) 6.59 (dd, J=8.84, 2.02 Hz, 1H) 6.88 (d, J=2.02 Hz, 1H) 7.37 (d, J=8.59 Hz, 1H).

Example 22

6-(Bis-cyclohexylmethyl-amino)-1-carboxymethoxy-3,8-dithia-cyclopenta[a]indene-2-carboxylic acid Following procedures similar tothose delineated in Example 21, steps A to G, the title compound was prepared via hydrolysis of 6-(bis-cyclohexylmethyl-amino)-1-ethoxycarbonylmethoxy-3,8-dithia-cyclopenta[a]indene-2-carboxylic acid methyl ester (22 mg, 0.039 mmol) as a yellow solid (15.2 mg, 75%).

1H NMR (400 MHz, DMSO-D6) δ ppm 0.82-1.09 (m, 2H) 1.08-1.30 (m, 3H) 1.48-1.87 (m, 6H) 3.31 (d, J=6.82 Hz, 2H) 5.06 (s, 2H) 6.93 (dd, J=8.97, 2.15 Hz, 1 H) 7.27 (d, J=2.27 Hz, 1H) 7.78 (d, J=8.84 Hz, 1H).

Example 23

1-Carboxymethoxy-6-(cyclohexvl-methoxycarbonyl-amino)-3,8-dithia-cycloventa[a]indene-2-carboxylic acid Following procedures similar tothose delineated in Example 21, steps A to G. the title compound was prepared via hydrolysis of 6-(cyclohexyl-methoxycarbonyl-amino)-1-ethoxycarbonylmethoxy-3,8-dithia-cyclopenta[a]indene-2-carboxylic acid methyl ester (38 mg, 0.075 mmol) as a white solid (30.3 mg, 87%).

1H NMR (400 MHz, DMSO-D6) δ ppm 1.01-1.20 (m, 1H) 1.23-1.38 (m, 2H) 1.42-1.62 (m, 2H) 1.62-1.79 (m, 1H) 1.85-1.96 (m, 2H) 2.05-2.15 (m, 2H) 3.75 (s, 3H) 4.19-4.36 (m, 1H) 5.30 (s, 2H) 7.50 (d, J=8.08 Hz, 2H) 8.19 (s, 1H) 8.29 (d, J=8.84 Hz, 1H).

Example 24

1-Carboxymethoxy-6-(1-cyclohexyl-3-ethyl-ureido)-3,8-dithia-cyclopenta[a]indene-2-carboxylic acid Following procedures similar tothose delineated in Example 21, steps A to G, the title compound was prepared via hydrolysis of 6-(1-cyclohexyl-3-ethyl-ureido)-1-ethoxycarbonylmethoxy-3,8-dithia-cyclopenta[a]indene-2-carboxylic acid methyl ester (55 mg, 1.06 mmol) as a white solid (41 mg, 81%).

1H NMR (400 MHz, DMSO-D6) δ ppm 0.68-0.76 (m, 1H) 0.79 (t, J=7.07 Hz, 3 H) 0.82-0.92 (m, 2H) 1.10-1.27 (m, 2H) 1.31-1.44 (m, 1H) 1.50-1.62 (m, 2H) 1.64-1.76 (m, 2H) 2.78-2.93 (m, 2H) 4.06-4.26 (m, 1H) 4.98 (s, 2H) 5.21 (t, J=5.56 Hz, 1H) 7.10 (dd, J=8.46, 1.89 Hz, 1H) 7.81 (d, J=1.52 Hz, 1H) 7.98 (d, J=8.34 Hz, 1 H).

Example 25

6-(Benzoyl-cyclohexyl-amino)-1-carboxymethoxy-3,8-dithia-cyclopenta[a]indene-2-carboxylic acid Following procedures similar tothose delineated in Example 21, steps A to G, the title compound was prepared via hydrolysis of 6-(benzoyl-cyclohexyl-amino)-1-ethoxycarbonylmethoxy-3,8-dithia-cyclopenta[a]indene-2-carboxylic acid methyl ester (50 mg, 0.909 mmol) as a white solid (35.5 mg, 77%).

1H NMR (400 MHz, DMSO-D6) δ ppm 0.81-1.02 (m, 1H) 1.04-1.23 (m, 2H) 1.26-1.45 (m, 2H) 1.46-1.63 (m, 1H) 1.67-1.76 (m, 2H) 1.91-2.02 (m, 2H) 4.45-4.60 (m, 1H) 5.04 (s, 2H) 7.09-7.20 (m, 3H) 7.22-7.32 (m, 3H) 7.93 (d, J=8.34 Hz, 1 H) 7.98 (d, J=2.02 Hz, 1H)

Step A: Alkylation: To a solution of 2-nitro-isophthalic acid (5.0g, 23.7 mmol), in DMF (80 mL) was added allyl bromide (10.3 mL, 118.5 mmol), and excess potassium carbonate (~30g, 237 mmol). The mixture was heated to 50° C. and allowed to stir for 3 hours, after which the reaction was judged complete by TLC. The reaction was quenched with excess water and the product was extracted into ethyl acteate (3×, 50 mL). The combined organic layers were washed with water (3×, 50 mL), dried over MgSO$_4$, and concentrated in vacuo, affording 6.50g of 2-nitro-isophthalic acid diallyl ester (95% yield). No purification was necessary.

1H NMR (400 MHz, CHLOROFORM-D) δ ppm 4.81 (d, J=5.81 Hz, 4H) 5.33 (dd, J=10.48, 1.14 Hz, 2H) 5.41 (dd, J=17.18, 1.26 Hz, 2H) 5.97 (m, 2H) 7.67 (t, J=7.83 Hz, 1H) 8.22 (d, J=8.08 Hz, 2H). LCMS: m/e =291.0 [M-H]$^-$ Step B Cycloaddition: A solution of 2-nitro-isophthalic acid diallyl ester (6.50 g, 22.3 mmol) in DMF (100 mL) was cooled to −78° C. Exactly one equivalent of methyl thioglycolate (2.02 miL) was then added. The solution was allowed to stir for a few minutes at −78° C., after which excess DBU was added (8.3 mL, 55.3 mmol). After one hour, the reaction was judged complete by TLC. The reaction mixture was and diluted with excess water (500 mL), and poured into a large Erlenmeyer flask The desired product was then precipitated out using 10% HCl (5-10 mL dropwise). The white solid was filtered, rinsed three times with water, and allowed to air dry, affording 3-Hydroxy Benzo[b]thiophene-2,7-carboxylic acid 7-allyl ester 2-methyl ester in quantitative yield. No purification was necessary.

1H NMR (400 MHz, CHLOROFORM-D) δ ppm 3.98 (s, 3H) 4.94 (d, J=5.81 Hz, 2H) 5.34 (dd, J=10.48, 1.14 Hz, 1H) 5.48 (dd, J=17.18, 1.26 Hz, 1H) 6.10 (m, 1H) 7.51 (t, J=7.71 Hz, 1H) 8.16 (dd, J=7.96, 1.14 Hz, 1H) 8.31 (dd, J=7.45, 1.14 Hz, 1H) 10.08 (br.s, 1H). LCMS: m/e =293.0 [M+H]$^+$ Step C Mesylation: A solution of 3-Hydroxy Benzo[b]thiophene-2,7-carboxylic acid 7-allyl ester 2-methyl ester (1.0 g, 3.4 mmol) in DCM (20 mL) was cooled to 0C. Excess triethylamine (1.2 mL, 2.5 mmol) was then added, followed by mesyl chloride (0.28 mL, 1.05 mmol). The reaction was allowed to stir at 0° C. for 30 minutes, after which it was judged complete by TLC. Excess water was then added, and the desired product was extracted into DCM (3×, 25 mL). The organic layers were combined, washed with aqueous sodium bicarbonate, dried over MgSO$_4$, and concentrated in vacuo. The crude product was then dissolved in a minimal amount of DCM, and filtered through a thick pad of silica gel using a 40% ethyl acetate/hexane solution, ultimately affording 1.0 g (2.7 mmol) of 3-Methanesulfonyloxy-benzo[b]thiophene-2,7-carboxylic acid 7-allyl ester 2-methyl ester as a pale yellow oil (80% yield).

1H NMR (400 MHz, CHLOROFORM-D) δ ppm 3.53 (s, 3H) 3.96 (s, 3H) 4.95 (d, J=5.81 Hz, 2H) 5.35 (dd, J=10.36, 1.26 Hz, 1H) 5.48 (dd, J=17.18, 1.52 Hz, 1H) 6.09 (m, 1H) 7.60 (t, 1H) 8.27 (dd, J=8.08, 1.26 Hz, 1H) 8.32 (dd, J=7.45, 1.14 Hz, 1 H).

Step D Cycloaddition: Conducted according to the procedure for step B with the exception of purification: The resulting product was a mixture of 3-Hydroxy Benzo[b]thiophene-2,7-carboxylic acid 7-allyl ester 2-methyl ester (bicyclic) and 1-hydroxy3,8-dithiacyclopenta[a]indine-2,7-dicarboxylic acid 7-allyl ester-2 methyl ester (tricyclic) compounds which were separable by trituration. The mixture was briefly refluxed in an ethyl acetate/methanol solution (2:1 vol.) upon which the bicyclic compound was dissolved in solution and the tricyclic compound remained a solid. Overall yield was quantitative, with a tricyclic : bicyclic mole ratio of 1.2:1.

1H NMR (400 MHz, CHLOROFORM-D) δ ppm 3.97 (s, 3H) 4.96 (d, J=5.81 Hz, 2H) 5.36 (dd, J=10.61, 1.26 Hz, 1H) 5.49 (dd, J=17.18, 1.26 Hz, 1H) 6.06-6.17 (m, 1H) 7.56 (t, J=7.71 Hz, 1H) 8.08 (dd, J=7.96, 1.14 Hz, 1H) 8.26 (dd, J=7.58, 1.01 Hz, 1H) 10.04 (br.s, 1H). LCMS: m/e =348.9 [M+H]$^+$ Step E Alkylation: To a solution of 1-hydroxy3,8-dithiacyclopenta[a]indine-2,7-dicarboxylic acid 7-allyl ester-2 methyl ester (1.05 g, 3.02 mmol) in DMF (25 mL) was added excess potassium carbonate and ethyl bromoacetate (5 mL). The reaction was allowed to stir at ambient temperature for two hours after which it was judged complete by TLC. Excess water was added to precipitate the desired product 1-Ethoxycarbonylmethoxy-3,8-dithiacyclopenta[a]indine-2,7-dicarboxylic acid 7-allyl ester-2 methyl ester as a white solid in quantitative yield. No purification was necessary.

1H NMR (400 MHz, CHLOROFORM-D) δ ppm 1.31 (t, J=7.20 Hz, 3H) 3.92 (s, 3H) 4.28 (q, J=7.07 Hz, 2H) 4.95 (d, J=5.56 Hz, 2H) 5.11 (s, 1H) 5.35 (dd, J=10.36, 1.26 Hz, 1H) 5.48 (dd, J=17.18, 1.52 Hz, 1H) 5.96-6.24 (m, 1H) 7.55 (t, J=7.71 Hz, 1 H) 8.07 (dd, J=7.96, 1.14 Hz, 1H) 8.24 (dd, J=7.58, 1.01 Hz, 1H). LCMS: m/e=456.9 [M+Na]$^+$ Step F De-allylation: To a solution of 1-Ethoxycarbonylmethoxy-3,8-dithiacyclopenta[a]indine-2,7-dicarboxylic acid 7-allyl ester-2 methyl ester (1.21 g, 2.8 mmol) in anhydrous THF (50 mL) was added Pd(PPh$_3$)$_4$ (320 mg, 0.28 mmol) under N$_2$ flow. Concentrated acetic acid was then added (2.5 mL), and the mixture was allowed to stir at ambient temperature for two hours, after which the reaction was judged complete by TLC. A 20% ethyl acetate/hexane solution was added to the reaction to precipitate out the desired product, 1-Ethoxycarbonylmethoxy-3,8-dithiacyclopenta[a]indine-2,7-dicarboxylic acid -2 methyl ester, in 68% yield (760 mg). No purification was necessary.

1H NMR (400 MHz, DMSO-D6) δ ppm 1.29 (t, J=7.07 Hz, 3H) 3.90 (s, 3H) 4.25 (q, J=7.07 Hz, 2H) 5.26 (s, 2H) 7.72 (t, J=7.71 Hz, 1H) 8.22 (dd, J=7.58, 1.01 Hz, 1H) 8.43 (dd, J=7.96, 0.88 Hz, 1H). LCMS: m/e =393.0 [M-H]$^-$ Step G Curtis Rearrangement: To a solution of 1-Ethoxycarbonylmethoxy-3,8-dithiacyclopenta[a]indine-2,7-dicarboxylic acid-2 methyl ester (450 mg, 1.14 mmol) in toluene (7.5 mL) was added DPPA (0.37 mL, 1.71 mmol), excess triethyl amine (0.40 mL, 2.86 mmol), and t-butanol (0.75 mL). The solution was allowed to stir at ambient temperature for two hours, after which the starting material was judged consumed by TLC. An additional 0.75 mL of t-butanol was then added and the reaction mixture was heated to 100° C. and allowed to stir for an additional 16 hour period, after which the reaction was judged complete by LCMS. The reaction was quenched with excess water and extracted into DCM (3×, 10 mL). The organic layers were combined, washed with water (3×, 10 mL), dried with MgSO$_4$, and concentrated in vacuo. The crude product was purified via normal phase SiO$_2$ chromatography using ethyl acteate/hexane (5% to 20% gradient) affording 535 mg of 7-tert-Butoxycarbonylamino-1-ethoxycarbonylmethoxy-3,8-dithia-cyclopenta[a]indene-2-carboxylic acid methyl ester (62% yield).

1H NMR (400 MHz, CHLOROFORM-D) δ ppm 1.28 (t, J=7.20 Hz, 3H) 3.92 (s, 3H) 4.26 (q, J=7.16 Hz, 2H) 5.06 (s, 2H) 6.41 (br.s, 1H) 7.45 (t, J=7.96 Hz, 1H) 7.61 (dd, J=7.83, 1.01 Hz, 1H) 7.92 (d, J=8.08 Hz, 1H). LCMS: m/e =463.6 [M-H]$^-$ Step H Deprotection: A solution of 7-tert-Butoxycarbonylamino-1-ethoxycarbonylmethoxy-3,8-dithia-cyclopenta[a]indene-2-carboxylic acid methyl ester (170 mg, 0.37 mmol) in DCM (6 mL) was cooled to 0° C. Trifluoroacetic acid (1.2 mL) was then added, and the solution was allowed to warm to ambient temperature, stirring a total of four hours, after which the reaction was judged complete by TLC. The reaction mixture was concentrated in vacuo, dissolved in ethyl acetate, and washed with sodium bicarbonate (3×10 mL). The organic layer was then concentrated in vacuo, affording 7-Amino-1-ethoxycarbonylmethoxy-3,8-dithia-cyclopenta[a]indene-2-carboxylic acid methyl ester in a quantitative yield.

1H NMR (400 MHz, CHLOROFORM-D) δ ppm 1.30 (t, J=7.20 Hz, 3H) 3.91 (s, 3H) 4.28 (q, J=7.24 Hz, 2H) 5.06 (s, 2H) 6.89 (dd, J=7.58, 1.01 Hz, 1H) 7.33 (t, J=7.71 Hz, 1H) 7.42 (dd, J=7.97, 0.88 Hz, 1H). LCMS: m/e =388.0 [M+Na]$^+$ Step A Reductive Amination: To a solution of 7-Amino-1-ethoxycarbonylmethoxy-3,8-dithia-cyclopenta[a]indene-2-carboxylic acid methyl ester (250 mg, 0.68 mmol) in DCE (6.5 mL) was added cyclohexanone (0.071 mL, 0.68 mmol), and NaBH$_3$(OAc)$_3$ (250 mg, 1.2 mmol). HOAc (0.05 mL, 0.82 mmol) was then added drop-wise and the solution was allowed to stir at ambient temperature for two hours after which the reaction was judged complete by TLC. The solution was filtered through silica gel, concentrated in vacuo and purified via normal phase SiO$_2$ chromatography using a 0% to 15% ethyl acetate/hexane gradient, affording 180 mg of 7-Cyclohexylamino-1-ethoxycarbonylmethoxy-3,8-dithia-cyclopenta[a]indene-2-carboxylic acid methyl ester as a viscous yellow oil.

1H NMR (400 MHz, CHLOROFORM-D) δ ppm 1.21-1.35 (m, 6H) 1.35-1.49 (m, 2H) 1.65-1.74 (m, 1H) 1.77-1.88 (m, 2H) 2.07-2.18 (m, 2H) 3.36-3.56 (m, 1 H) 3.91 (s, 3H) 4.27 (q, J=7.24 Hz, 2H) 5.07 (s, 2H) 6.70 (dd, J=7.83, 1.01 Hz, 1H) 7.24 (dd, J=7.83, 1.01, 1H) 7.32 (t, J=7.83 Hz, 1H).

Example 26

1-Carboxymethoxy-7-cyclohexylamino-3,8-dithia-cyclopenta[a]indene-2-carboxylic acid Step C Hydrolysis: To a solution of 7-Cyclohexylamino-1-ethoxycarbonylmethoxy-3,8-dithia-cyclopenta[a]indene-2-carboxylic acid methyl ester (30 mg, 0.07 mmol) in THF/H$_2$O (1.5 mL/0.5 mL) was added 2.0M LiOH (0.15 mL, 0.35 mmol). The reaction was allowed to stir at ambient temperature over a 16-hour period, after which it was judged complete by LCMS. The THF was removed in vacuo and the resultant aqueous solution was acidified to pH ~1-2 using 10% HCl to precipitate the desired compound which was filtered, rinsed with water, and oven-dried (55° C.). No purification was necessary. (Yield=20 mg, 71%)

1H NMR (400 MHz, DMSO-D6) δ ppm 1.15-1.30 (m, 1H) 1.32-1.46 (m, 4H) 1.64-1.73 (m, 1H) 1.75-1.85 (m, 2H) 1.98-2.07 (m, 2H) 5.07 (br.s, 2H) 5.42 (d, J=8.59 Hz, 1H) 6.78 (d, J=7.58 Hz, 1H) 7.30 (dd, J=7.83, 1.01 Hz, 1H) 7.35 (t, J=7.71 Hz, 1H). LCMS: m/e =406.8 [M+1]+

Example 27

7-(Acetyl-cyclohexyl-amino)-1-carboxymethoxy-3,8-dithia-cyclopenta[a]indene-2-carboxylic acid Step B Amide Formation: A solution of 7-Cyclohexylamino-1-ethoxycarbonylmethoxy-3,8-dithia-cyclopenta[a]indene-2-carboxylic acid methyl ester (50 mg, 0.11 mmol) in DCM/pyridine (1 mL/0.2 mL) was cooled to −78° C. Acetyl chloride was then added (0.04 mL, 0.55 mmol) and the reaction was allowed to stir and warm to ambient temperature over two hours after which it was judged complete by TLC. The reaction was quenched with excess aqueous NaHCO$_3$, and extracted twice into DCM. The organic layers were combined, washed with brine, dried with MgSO$_4$, and concentrated in vacuo. The crude product was purified using normal phase SiO$_2$ chromatography, and afforded 33 mg of the desired amide 7-(acetyl-cyclohexyl-amino)-1-ethoxycarbonylmethoxy-3,8-dithia-cyclopenta[a]indene-2-carboxylic acid methyl ester (61% yield).

1H NMR (400 MHz, CHLOROFORM-D) δ ppm 0.87-1.06 (m, 2H) 1.30 (t, J=7.07 Hz, 3H) 1.32-1.47 (m, 3H) 1.62-1.71 (m, 1H) 1.73-1.77 (m, 1H) 1.78 (s, 3 H) 1.93-2.09 (m, 2H) 3.92 (s, 3H) 4.27 (q, J=7.16 Hz, 2H) 4.56-4.72 (m, 1H) 5.05 (s, 2H) 7.22 (dd, J=7.58, 1.01 Hz, 1H) 7.52 (t, J=7.83 Hz, 1H) 7.88 (dd, J=7.96, 0.88 Hz, 1H).

Step C Hydrolysis: Hydrolysis of 7-(Acetyl-cyclohexyl-amino)-1-ethoxycarbonylmethoxy-3,8-dithia-cyclopenta[a]indene-2-carboxylic acid methyl ester (33 mg, 0.07 mmol) was carried out following a procedure similar to that delineated in Step C, Example 1, affording 17 mg of the desired diacid (67% yield).

1H NMR (400 MHz, DMSO-D6) δ ppm 0.86-1.06 (m, 2H) 1.27-1.42 (m, 3H) 1.51-1.61 (m, 1H) 1.64-1.69 (m, 1H) 1.74-1.84 (m, 1H) 1.90-1.98 (m, 1H) 1.99-2.08 (m, 1H) 4.44-4.60 (m, 1H) 5.12 (s, 2H) 7.49 (d, J=7.58 Hz, 1H) 7.69 (t, J=7.83 Hz, 1H) 8.22 (d, J=7.83 Hz, 1H). LCMS: m/e =447.6 [M+H]+

Example 28

1-Carboxymethoxy-7-(cyclohexyl-methoxycarbonyl-amino)-3,8-dithia-cyclopenta[a]indene-2-carboxylic acid Step B Carbamate Formation: Addition of methyl chloroformate (0.04 mL, 0.55 mmol) to 7-Cyclohexylamino-1-ethoxycarbonylmethoxy-3,8-dithia-cyclopenta[a]indene-2-carboxylic acid methyl ester (50 mg, 0.11 mmol) was carried out following a procedure similar to that delineated in Step B, Example 27, affording 25 mg of the desired carbamate 7-(Cyclohexyl-methoxycarbonyl-amino)-l-ethoxycarbonyl-methoxy-3,8-dithia-cyclopenta[a]indene-2-carboxylic acid methyl ester (45% yield).

1H NMR (400 MHz, CHLOROFORM-D) δ ppm 0.86-1.01 (m, 1H) 1.00-1.14 (m, 1H) 1.30 (t, J=7.07 Hz, 3H) 1.33-1.49 (m, 2H) 1.53-1.58 (m, 1H) 1.62-1.72 (m, 1H) 1.75-1.85 (m, 1H) 1.95-2.05 (m, 1H) 2.07-2.17 (m, 1H) 3.61 (s, 3H) 3.92 (s, 3 H) 4.16-4.31 (m, 3H) 5.05 (s, 2H) 7.21 (d, J=8.08 Hz, 1H) 7.47 (t, J=7.71 Hz, 1H) 7.82 (dd, J=7.83, 1.01 Hz, 1H).

Step C Hydrolysis: Hydrolysis of 7-(Cyclohexyl-methoxycarbonyl-amino)-1-ethoxycarbonylmethoxy-3,8-dithia-cyclopenta[a]indene-2-carboxylic acid methyl ester was carried out following a procedure similar to that delineated in Step C, Example 26, affording 6.2 mg of the desired diacid (25% yield).

1H NMR (400 MHz, DMSO-D6) δ ppm 0.89-1.01 (m, 1H) 1.02-1.15 (m, 1H) 1.28-1.53 (m, 3H) 1.53-1.63 (m, 1H) 1.64-1.76 (m, 1H) 1.76-1.88 (m, 1H) 1.93-2.02 (m, 1H) 2.06-2.17 (m, 1H) 3.59 (s, 3H) 4.11-4.23 (m, 1H) 5.08 (s, 2H) 7.43 (dd, J=7.58, 0.76 Hz, 1H) 7.63 (t, J=7.83 Hz, 1H) 8.14 (dd, J=7.96, 0.88 Hz, 1H). LCMS: m/e =463.6 [M+H]+

Step A Reductive Amination: Addition of cyclohexane carboxaldehyde (0.063 mL, 0.61 mmol), to 7-Amino-1-ethoxycarbonylmethoxy-3,8-dithia-cyclopenta[a]indene-2-carboxylic acid methyl ester (250 mg, 0.61 mmol) was carried out following a procedure similar to that delineated in step A ("reductive amination," Example 25) affording 180 mg of 7-(Cyclohexylmethyl-amino)-1-ethoxycarbonylmethoxy-3,8-dithia-cyclopenta[a]indene-2-carboxylic acid methyl ester as a viscous yellow oil.

1H NMR (400 MHz, CHLOROFORM-D) δ ppm 0.97-1.11 (m, 2H) 1.23-1.33 (m, 5H) 1.63-1.81 (m, 6H) 1.83-1.90 (m, 2H) 3.15 (d, J=6.82 Hz, 2H) 3.91 (s, 3H) 4.27 (q, J=7.07 Hz, 3H) 5.07 (s, 2H) 6.67 (dd, J=7.83, 0.76 Hz, 1H) 7.26 (d, J=7.83, 1.01 Hz, 1H) 7.34 (t, J=7.83 Hz, 1H).

Example 29

1-Carboxymethoxy-7-(cyclohexylmethyl-amino)-3,8-dithia-cyclopenta[a]indene-2-carboxylic acid Step C Hydrolysis: Hydrolysis of 7-(Cyclohexylmethyl-amino)-1-ethoxycarbonylmethoxy-3,8-dithia-cyclopenta[a]indene-2-carboxylic acid methyl ester (30 mg, 0.065 mmol) was carried out following a procedure similar to that delineated in Step C, Example 26, affording 8.2 mg of the desired diacid as a green solid. (28% yield).

1H NMR (400 MHz, DMSO-D6) δ ppm 0.94-1.10 (m, 2H) 1.17-1.35 (m, 3H) 1.63-1.82 (m, 4H) 1.85-1.96 (m, 2H) 3.11-3.18 (m, 2H) 5.11 (s, 2H) 5.87-5.96 (m, 1H) 6.73 (d, J=7.83 Hz, 1H) 7.31 (d, J=7.83 Hz, 1H) 7.38 (t, J=7.83 Hz, 1H). LCMS: m/e=419.6 [M+H]+

Example 30

7-(Acetyl-cyclohexylmethyl-amino)-1-carboxymethoxy-3,8-dithia-cyclopenta[a]indene-2-carboxylic acid Step B Amide Formation: Addition of acetyl chloride (0.05 mL, 0.65 mmol) to 7-(Cyclohexylmethyl-amino)-1-ethoxycarbonylmethoxy-3,8-dithia-cyclopenta[a]indene-2-carboxylic acid methyl ester (60 mg, 0.13 mmol) was carried out following a procedure similar to that delineated in Step B, Example 27, affording 38 mg of 7-(Acetyl-cyclohexylmethyl-amino)-1-ethoxycarbonylmethoxy-3,8-dithia-cyclopenta[a]indene-2-carboxylic acid methyl ester as a yellow solid. (58% yield).

1H NMR (400 MHz, CHLOROFORM-D) δ ppm 0.85-0.92 (m, 1H) 0.98-1.10 (m, 2H) 1.12-1.21 (m, 2H) 1.24-1.28 (m, 1H) 1.30 (t, J=7.07 Hz, 3H) 1.41-1.54 (m, 1H) 1.61-1.80 (m, 4H) 1.85 (s, 3H) 3.37 (dd, J=13.39, 6.32 Hz, 1H) 3.99 (dd, J=13.52, 8.21 Hz, 1H) 4.27 (q, J=7.24 Hz, 2H) 5.06 (s, 2H) 7.29 (dd, J=7.96, 0.88 Hz, 1H) 7.53 (t, J=7.71 Hz, 1H) 7.87 (dd, J=7.96, 0.88 Hz, 1H).

Step C Hydrolysis: Hydrolysis of 7-(Acetyl-cyclohexylmethyl-amino)-1-ethoxycarbonylmethoxy-3,8-dithia-cyclopenta[a]indene-2-carboxylic acid methyl ester (38 mg, 0.075 mmol) was carried out following a procedure similar to that delineated in Step C, Example 26, affording 23 mg for the desired diacid. (61% yield).

1H NMR (400 MHz, DMSO-D6) δ ppm 0.87-1.01 (m, 2H) 1.06-1.17 (m, 3H) 1.31-1.43 (m, 1H) 1.53-1.59 (m, 1H) 1.60-1.68 (m, 3H) 1.68-1.71 (m, 1H) 3.82 (dd, J=13.39, 7.58 Hz, 1H) 5.07 (s, 2H) 7.54 (dd, J=7.58, 1.01 Hz, 1H) 7.64 (t, J=7.83 Hz, 1H) 8.15 (dd, J=7.96, 0.88 Hz, 1H). LCMS: m/e =461.6 [M+H]$^+$ Example 31

1-Carboxymethoxy-7-(cyclohexylmethyl-methoxy-carbonyl-amino)-3,8-dithia-cyclopenta[a]indene-2-carboxylic acid Step B Carbamate Formation: Addition of methyl chloroformate (0.05 mL, 0.65 mmol) to 7-(Cyclohexylmethyl-amino)-1-ethoxycarbonylmethoxy-3,8-dithia-cyclopenta[a]indene-2-carboxylic acid methyl ester (60 mg, 0.13 mmol) was carried out following a procedure similar to that delineated in Step B, Example 27, affording 43 mg of 7-(Cyclohexylmethyl-methoxycarbonyl-amino)-1-ethoxycarbonylmethoxy-3,8-dithia-cyclopenta[a]indene-2-carboxylic acid methyl ester (63% yield).

1H NMR (400 MHz, CHLOROFORM-D) δ ppm 0.86-0.91 (m, 1H) 0.95-1.03 (m, 2H) 1.11-1.20 (m, 3H) 1.30 (t, J=7.20 Hz, 3H) 1.60-1.65 (m, 1H) 1.67-1.73 (m, 2H) 1.73-1.80 (m, 2H) 3.47-3.75 (m, 5H) 3.92 (s, 3H) 4.27 (q, J=7.07 Hz, 2H) 5.05 (s, 2H) 7.28 (d, J=7.96 Hz, 1H) 7.48 (t, J=7.83 Hz, 1H) 7.80 (dd, J=7.96, 0.88 Hz, 1H)

Step C Hydrolysis: Hydrolysis of 7-(Cyclohexylmethyl-methoxycarbonyl-amino)-1-ethoxycarbonylmethoxy-3,8-dithia-cyclopenta[a]indene-2-carboxylic acid methyl ester (43 mg, 0.082 mmol) was carried out following a procedure similar to that delineated in Step C, Example 26, affording 28 mg of the desired diacid as a white solid. (54% yield).

1H NMR (400 MHz, DMSO-D6) δ ppm 0.87-1.00 (m, 2H) 1.04-1.16 (m, 3H) 1.30-1.43 (m, 1H) 1.59-1.74 (m, 4H) 3.49-3.63 (m, 5H) 5.07 (s, 2H) 7.48 (dd, J=7.58, 1.01 Hz, 1H) 7.58 (t, J=7.71 Hz, 1H) 8.05 (dd, J=7.83, 1.01 Hz, 1H). LCMS: m/e =477.8 [M+H]$^+$ Example 32

1-Carboxymethoxy-7-(1-cyclohexylmethyl-3-ethyl-ureido)-3,8-dithia-cyclopenta[a]indene-2-carboxylic acid Step B Urea Formation: Addition of ethyl isocyanate (0.5 mL, 6.5 mmol) to 7-(Cyclohexylmethyl-amino)-1-ethoxycarbonylmethoxy-3,8-dithia-cyclopenta[a]indene-2-carboxylic acid methyl ester (60 mg, 0.13 mmol) was carried out following a procedure similar to that delineated in Step B, Example 27, with the following exceptions: co-solvent (DCE), addition of catalytic DMAP, temperature (70° C. vs. ambient), and total reaction time (100+ hours), affording 30 mg of 7-(1-Cyclohexylmethyl-3-ethyl-ureido)-1-ethoxycarbonylmethoxy-3,8-dithia-cyclopenta[a]indene-2-carboxylic acid methyl ester (43% yield).

1H NMR (400 MHz, CHLOROFORM-D) δ ppm 0.94-1.06 (m, 4H) 1.10-1.17 (m, 7H) 1.37-1.50 (m, 1H) 1.57-1.61 (m, 1H) 1.66-1.81 (m, 4H) 3.92 (s, 3H) 4.26 (q, J=7.07 Hz, 2H) 5.05 (s, 2H) 7.06 (s, 1H) 7.34 (dd, J=7.58, 1.01 Hz, 1 H) 7.53 (t, J=7.83 Hz, 1H) 7.85 (dd, J=8.08, 1.01 Hz, 1H)

Step C Hydrolysis: Hydrolysis of 7-(1-Cyclohexylmethyl-3-ethyl-ureido)-1-ethoxycarbonylmethoxy-3,8-dithia-cyclopenta[a]indene-2-carboxylic acid methyl ester (30 mg, 0.056 mmol) was carried out following a procedure similar to that delineated in Step C, Example 26, with the exception of an ethyl acetate wash (3×, 5 mL) before precipitation of the desired diacid, to remove a minor impurity associated with the isocyanate. (8.6 mg yellow solid, 28% yield).

1H NMR (400 MHz, DMSO-D6) δ ppm 0.94 (dd, J=5.18, 1.89 Hz, 2H) 1.02-1.14 (m, 3H) 1.26-1.37 (m, 1H) 1.53-1.59 (m, 1H) 1.59-1.73 (m, 4H) 2.91-3.01 (m, 2H) 3.53 (d, J=7.33 Hz, 2H) 5.06 (s, 2H) 5.82 (t, J=5.68 Hz, 1H) 7.41 (dd, J=7.58, 0.76 Hz, 1H) 7.58 (t, J=7.83 Hz, 1H) 8.04 (dd, 1H). LCMS: m/e =490.5 [M+H]$^+$ Example 33

(6-Chloro-2-cyano-3,8-dithia-cyclopenta[a]inden-1-yloxy)-acetic acid

Step A: A solution of methyl 6-chloro-3-{ [(trifluoromethyl)sulfonyl]oxy}-1-benzothiophene-2-carboxylate (2.0 g, 5.3 mmol) and triethylamine (890 μL, 1.2 eq), in dichloromethane (45 mL) was cooled to −20° C. and methyl thioglycolate(908 μL, 2.5 eq) was added dropwise via syringe pump over 5 h. The reaction was allowed to warm to room temperature overnight. The solution was diluted with water, and ethyl acetate, washed with water and brine, dried, filtered, evaporated, and flash chromatographed (10-20% ethyl acetate/hexanes) to provide methyl 6-chloro-3-[(cyanomethyl)thio]-1-benzothiophene-2-carboxylate (1.01 g, 64%) as a white solid.

1H NMR (400 MHz, CHLOROFORM-D) δ ppm 3.88 (s, 2H), 3.99 (s, 3H), 7.50 (dd, J=8.7, 1.9 Hz, 1H), 7.87 (d, J=1.5 Hz, 1H), 8.16 (d, J=8.8 Hz, 1H).

Step B: A solution of methyl 6-chloro-3-[(cyanomethyl)thio]-1-benzothiophene-2-carboxylate (1.01 g, 3.4 mmol) in DMF (20 mL) was cooled to 0° C., and lithium hydroxide hydrate (171 mg, 1.2 eq) was added in a single portion. After 1h, the solution was warmed to room temperature and stirred for an additional hour. The reaction solution was diluted with aq. hydrochloric acid and ethyl acetate. The organic layer was washed with water and brine, dried, filtered, evaporated, and recrystallized (EtOH) to provide 6-chloro-3-hydroxythieno[3,2-b][1]benzothiophene-2-carbonitrile (393 mg, 43%) as an off-white solid.

1H NMR (400 MHz, DMSO-D6) δ ppm 3.34 (bs, 1H), 7.56 (dd, J=8.6, 1.8 Hz, 1 H), 8.13 (d, J=8.6 Hz, 1H), 8.33 (d, J=2.0 Hz, 1H)

Step C: A solution of 6-chloro-3-hydroxythieno[3,2-b][1]benzothiophene-2-carbonitrile (200 mg, 0.8 mmol), potassium carbonate (156 mg, 1.5 eq), methyl bromoacetate (110 μL, 1.5 eq) in DMF was heated at 60° C. for 1.5 h. The solution was diluted with ethyl acetate, washed with water and brine, dried, filtered, evaporated, and flash chromatographed (20-30% ethyl acetate/hexanes) to provide methyl [(6-chloro-2-cyanothieno[3,2-b][1]benzothien-3-yl)oxy]acetate (230 mg, 90%) as a white, fibrous solid.

1H NMR (400 MHz, CHLOROFORM-D) δ ppm 3.87 (s, 3H), 5.13 (s, 2H), 7.44 (dd, J=8.5, 1.9 Hz, 1H), 7.76 (d, J=8.6 Hz, 1H), 7.86 (d, J=1.8 Hz, 1H)

Step D: A solution of methyl [(6-chloro-2-cyanothieno[3,2-b][1]benzothien-3-yl)oxy]acetate (100 mg, 0.3 mmol) and potassium hydroxide (39 mg, 2 eq) in THF (2 mL), MeOH, (1 mL), and water (1 mL) was stirred at room temperature for 4h. The solvents were removed by evaporation, and the resulting oil was acidified with aq. hydrochloric acid, filtered, washed with water and dried in a vacuum oven overnight to provide [(6-chloro-2-cyanothieno[3,2-b][1]benzothien-3-yl)oxy] acetic acid (72 mg). This sample was further purified by reverse phase HPLC to provide 23 mg of the product.

1H NMR (400 MHz, DMSO-D6) δ ppm 5.17 (s, 2H), 7.59 (dd, J=8.6, 2.0 Hz, 1 H), 8.21 (d, J=8.6 Hz, 1H), 8.37 (d, J=1.8 Hz, 1H).

Example 34

Biological Testing

Evaluation of the utility of a PTPase inhibitor, such as those described here, can be performed using a variety of methods previously described, with generally applicable techniques and specific examples (1-5).

1. Fersht, A. *Structure and Mechanism in Protein Science: A Guide to Enzyme Catalysis and Protein Folding* (W.H. Freeman and Company, New York, 1999).
2. McCain D F, Zhang Z Y: Assays for protein-tyrosine phosphatases. *Methods Enzymol.* (2002) 345:507-518.
3. Tonks N K, Diltz C D, Fisher E H: Characterization of the major protein tyrosine phophatases of human placenta *J. Biol. Chem.* (1988) 263:6731-6737.
4. Barford D, Flint A J, Tonks N K: Crystal structure of human protein tyrosine phosphatase 1B. *Science* (1994) 263: 1397-1404.
5. Huyer G, Lui S, Kelly J, Moffat J, Payette P, Kennedy B, Tsaprailus G, Gresser M J, Ramachandran C: Mechanism of inhibition of protein-tyrosine phosphatases by vanadate and pervanandate. *J. Biol. Chem.* (1997) 272:843-851."

A number of embodiments of the invention have been described. Nevertheless, it will be understood that various modifications may be made without departing from the spirit and scope of the invention. Accordingly, other embodiments are in the claims.

What is claimed is:

1. A compound having formula (I):

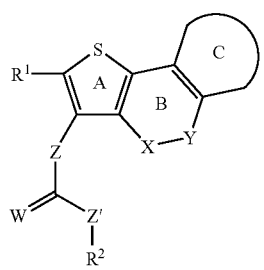

(I)

wherein:
X is S;
Y is a bond;
ring C is:
(i) a fused $C_6$-$C_{16}$ aryl or a fused heteroaryl including 5-16 atoms, each of which is optionally substituted with from 1-10 $R^3$; or
(ii) a fused $C_3$-$C_{10}$ cycloalkyl, a fused $C_3$-$C_{10}$ cycloalkenyl, a fused heterocyclyl including 5-10 atoms, or a fused heterocycloalkenyl including 5-10 atoms, each of which is optionally substituted with from 1-5 $R^4$;

$R^1$ is:
(i) $C_6$-$C_{16}$ aryl or heteroaryl including 5-16 atoms, each of which is optionally substituted with from 1-10 $R^g$; or (ii) $C_3$-$C_{16}$ cycloalkyl or $C_3$-$C_{16}$ halocycloalkyl, each of which is optionally substituted with from 1-5 $R^h$; or
(iii) $C_3$-$C_{10}$ cycloalkenyl, heterocyclyl including 5-10 atoms, or heterocycloalkenyl including 5-10 atoms, each of which is optionally substituted with from 1-5 $R^i$; or
(iv) cyano, —C(O)$R^j$, —C(O)O$R^j$, —OC(O)$R^j$, —C(O)S$R^j$, —SC(O)$R^j$, —C(S)S$R^j$, —SC(S)$R^j$, —NR$^k$C(O)$R^j$, —C(O)NR$^m$R$^n$; or —C(NR$^o$)$R^j$;

W is O or S;
each of Z and Z' is, independently:
(i) O, NR$^p$, S, SO, or SO$_2$; or
(ii) $C_1$-$C_{12}$ alkylene, $C_2$-$C_{12}$ alkenylene, $C_2$-$C_{12}$ alkynylene, O($C_1$-$C_{12}$ alkylene), O($C_2$-$C_{12}$ alkenylene), O($C_2$-$C_{12}$ alkynylene), NR$^p$($C_1$-$C_{12}$ alkylene), NR$^p$($C_2$-$C_{12}$ alkenylene), NR$^p$($C_2$-$C_{12}$ alkynylene), S($C_1$-$C_{12}$ alkylene), S($C_2$-$C_{12}$ alkenylene), S($C_2$-$C_{12}$ alkynylene), SO($C_1$-$C_{12}$ alkylene), SO($C_2$-$C_{12}$ alkenylene), SO($C_2$-$C_{12}$ alkynylene), SO$_2$($C_1$-$C_{12}$ alkylene), SO$_2$($C_2$-$C_{12}$ alkenylene), or SO$_2$($C_2$-$C_{12}$ alkynylene), each of which is optionally substituted with 1-5 R$^q$;

$R^2$ is:
(i) hydrogen; or
(ii) $C_1$-$C_{20}$ alkyl, optionally substituted with from 1-10 R$^r$ and/or optionally inserted with from 1-10 heteroatoms selected from the group consisting of nitrogen, oxygen or sulfur; or
(iii) $C_1$-$C_{20}$ haloalkyl, optionally substituted with from 1-10 R$^r$; or
(iv) $C_3$-$C_{20}$ cycloalkyl or $C_3$-$C_{20}$ halocycloalkyl, optionally substituted with from 1-10 R$^h$; or
(v) $C_3$-$C_{20}$ cycloalkenyl, heterocyclyl including 3-20 atoms, or heterocycloalkenyl including 3-20 atoms, each of which is optionally substituted with from 1-10 R$^i$; or
(vi) $C_2$-$C_{20}$ alkenyl or $C_2$-$C_{20}$ alkynyl, each of which is optionally substituted with from 1-10 R$^s$;
(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 R$^t$; or
(viii) $C_6$-$C_{16}$ aryl or heteroaryl including 5-16 atoms, each of which is optionally substituted with from 1-10 R$^g$;

each of $R^3$ and $R^4$, is, independently:
(i) halo; NR$^m$R$^n$; nitro; azido, hydroxy; oxo; thioxo; =NR$^o$; $C_1$-$C_{12}$ alkoxy, optionally substituted with 1-5 R$^r$; $C_1$-$C_{12}$ haloalkoxy; $C_6$-$C_{16}$ aryloxy, optionally substituted with 1-5 R$^g$; $C_2$-$C_{12}$ alkenyloxy or $C_2$-$C_{12}$ alkynyloxy, each of which is optionally substituted with 1-5 R$^s$; $C_3$-$C_{16}$ cycloalkyloxy or $C_3$-$C_{16}$ halocycloalkyloxy, each of which is optionally substituted with 1-5 R$^h$; heterocyclyloxy including 3-16 atoms, optionally substituted with 1-5 R$^i$; $C_7$-$C_{20}$ aralkoxy, optionally substituted with 1-5 R$^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR$^m$R$^n$; —NR$^k$C(O)$R^j$; —C(NR$^o$)$R^j$; —OC(O)NR$^m$R$^n$; —NR$^k$C(O)NR$^m$R$^n$; —NR$^k$C(O)O$R^j$; —S(O)$_n$R$^u$; —NR$^k$S(O)$_n$R$^j$; or —P(O)(OR$^m$)(OR$^n$); or
(ii) $C_1$-$C_{20}$ alkyl, optionally substituted with from 1-10 R$^r$ and/or optionally inserted with from 1-10 heteroatoms selected from the group consisting of nitrogen, oxygen or sulfur; or
(iii) $C_1$-$C_{20}$ haloalkyl, optionally substituted with from 1-10 R$^r$; or (iv) $C_3$-$C_{20}$ cycloalkyl or $C_3$-$C_{20}$ halocycloalkyl, optionally substituted with from 1-10 $R^h$; or (v) $C_3$-$C_{20}$ cycloalkenyl, heterocyclyl including 3-20 atoms, or heterocycloalkenyl including 3-20 atoms, each of which is optionally substituted with from 1-10 $R^i$; or (vi) $C_2$-$C_{20}$ alkenyl or $C_2$-$C_{20}$ alkynyl, each of which is optionally substituted with from 1-10 $R^s$;

(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$;

$R^g$ at each occurrence is, independently:

(i) halo; $NR^mR^n$; nitro; azido, hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$ or $R^{g'}$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$); or (ii) $C_1$-$C_{12}$ alkyl, optionally substituted with from 1-10 $R^r$ and/or optionally inserted with from 1-6 heteroatoms selected from the group consisting of nitrogen, oxygen or sulfur; or (iii) $C_3$-$C_{20}$ cycloalkyl or $C_3$-$C_{20}$ halocycloalkyl, optionally substituted with from 1-10 $R^h$; or (iv) $C_3$-$C_{20}$ cycloalkenyl, heterocyclyl including 3-20 atoms, or heterocycloalkenyl including 3-20 atoms, each of which is optionally substituted with from 1-10 $R^i$; or (v) $C_2$-$C_{20}$ alkenyl or $C_2$-$C_{20}$ alkynyl, each of which is optionally substituted with from 1-10 $R^s$; or (vi) $C_1$-$C_{12}$ haloalkyl; or (vii) $C_7$-$C_{20}$ aralkyl or heteroaralkyl including 6-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$ or $R^{g'}$;

$R^{g'}$ at each occurrence is, independently, $C_1$-$C_{12}$ alkyl, $C_1$-$C_{12}$ haloalkyl, $C_2$-$C_{12}$ alkenyl; $C_2$-$C_{12}$ alkynyl; $C_3$-$C_{20}$ cycloalkyl; $C_3$-$C_{20}$ halocycloalkyl; $C_3$-$C_{20}$ cycloalkenyl, heterocyclyl including 3-20 atoms, or heterocycloalkenyl including 3-20 atoms; $C_7$-$C_{20}$ aralkyl; $C_6$-$C_{16}$ aryl or heteroaryl including 5-16 atoms; halo; $NR^mR^n$; nitro; azido; hydroxy; $C_1$-$C_{12}$ alkoxy; $C_1$-$C_{12}$ haloalkoxy; $C_6$-$C_{16}$ aryloxy; $C_2$-$C_{12}$ alkenyloxy; $C_2$-$C_{12}$ alkynyloxy; $C_3$-$C_{16}$ cycloalkyloxy; $C_3$-$C_{16}$ halocycloalkyloxy; heterocyclyloxy including 3-16 atoms; $C_7$-$C_{20}$ aralkoxy; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$);

$R^h$ at each occurrence is, independently:

(i) $NR^mR^n$; nitro; azido; hydroxy; oxo; thioxo; =$NR^o$; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$); or (ii) $C_2$-$C_{20}$ alkenyl or $C_2$-$C_{20}$ alkynyl, each of which is optionally substituted with from 1-10 $R^s$; or (iii) $C_6$-$C_{16}$ aryl or heteroaryl including 5-16 atoms, each of which is optionally substituted with from 1-10 $R^g$;

$R^i$ at each occurrence is, independently:

(i) halo, $NR^mR^n$; nitro; azido, hydroxy; oxo, thioxo, =$NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)N$R^mR^n$; —$NR^k$C(O)$R^j$; —C($NR^o$)$R^j$; —OC(O)N$R^mR^n$; —$NR^k$C(O)N$R^mR^n$; —$NR^k$C(O)O$R^j$; —S(O)$_n$$R^u$; —$NR^k$S(O)$_n$$R^j$; or —P(O)(O$R^m$)(O$R^n$); or (ii) $C_2$-$C_{20}$ alkenyl or $C_2$-$C_{20}$ alkynyl, each of which is optionally substituted with from 1-10 $R^s$; or (iii) $C_6$-$C_{16}$ aryl or heteroaryl including 5-16 atoms, each of which is optionally substituted with from 1-10 $R^g$;

each of $R^j$, $R^k$, $R^m$, and $R^n$, at each occurrence is, independently:

(i) hydrogen; or (ii) $C_1$-$C_{20}$ alkyl, optionally substituted with from 1-10 $R^r$ and/or optionally inserted with from 1-6 heteroatoms selected from the group consisting of nitrogen, oxygen or sulfur;

(iii) $C_1$-$C_{20}$ haloalkyl; or (iv) $C_2$-$C_{20}$ alkenyl or $C_2$-$C_{20}$ alkynyl, each of which is optionally substituted with from 1-10 $R^s$; or (v) $C_3$-$C_{20}$ cycloalkyl or $C_3$-$C_{20}$ halocycloalkyl, each of which is optionally substituted with from 1-10 $R^h$; or (vi) $C_3$-$C_{20}$ cycloalkenyl, heterocyclyl including 3-16 atoms, or heterocycloalkenyl including 3-16 atoms, each of which is optionally substituted with from 1-10 $R^i$; or (vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$;

$R^o$ is hydrogen; $C_1$-$C_{12}$ alkyl optionally inserted with from 1-6 heteroatoms selected from the group consisting of nitrogen, oxygen or sulfur; $C_2$-$C_{20}$ alkenyl; $C_2$-$C_{20}$ alkynyl; $C_7$-$C_{20}$ aralkyl; heteroaralkyl including 6-20 atoms; $C_3$-$C_{16}$ cycloalkyl; $C_3$-$C_{16}$ cycloalkenyl; heterocyclyl including 3-16 atoms; heterocycloalkenyl including 3-16 atoms; $C_8$-$C_{20}$ arylcycloalkyl; $C_8$-$C_{20}$ arylcycloalkenyl; arylheterocyclyl including 8-20 atoms; or arylheterocycloalkenyl including 8-20 atoms; $C_6$-$C_{16}$ aryl; heteroaryl including 5-16 atoms; $NR'''R''$, or $OR^j$;

$R^p$ is hydrogen or $C_1$-$C_{12}$ alkyl;

$R^q$ at each occurrence is, independently, halo, $NR'''R''$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; —$NR^k$C(O)$R^j$; —C($NR^o$)$R^j$; —OC(O)NR'''R''; —$NR^k$C(O)NR'''R''; —$NR^k$C(O)O$R^j$; —S(o)$_n$$R^u$; —$NR^k$S(O)$_n$$R^j$; or —P(O)(O$R'''$)(O$R''$);

$R^r$ at each occurrence is, independently, $NR'''R''$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; —$NR^k$C(O)$R^j$; —C($NR^o$)$R^j$; —OC(O)NR'''R''; —$NR^k$C(O)NR'''R''; —$NR^k$C(O)O$R^j$; —S(O)$_n$$R^u$; —$NR^k$S(O)$_n$$R^j$; or —P(O)(O$R'''$)(O$R''$);

$R^s$ at each occurrence is, independently, halo, $NR'''R''$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; —$NR^k$C(O)$R^j$; —(NR$^o$)$R^j$; —OC(O)NR'''R''; —$NR^k$C(O)NR'''R''; —$NR^k$C(O)O$R^j$; —S(O)$_n$$R^u$; —$NR^k$S(O)$_n$$R^j$; or —P(O)(O$R'''$)(O$R''$);

$R^t$ at each occurrence is, independently:
(i) $C_1$-$C_{12}$ alkyl, $C_1$-$C_{12}$ haloalkyl, halo, $NR'''R''$; nitro; azido, hydroxy; oxo, thioxo, $=NR^o$, $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; —$NR^k$C(O)$R^j$; —C($NR^o$)$R^j$; OC(O)NR'''R''; $NR^k$C(O)NR'''R''; —$NR^k$C(O)O$R^j$; —S(O)$_n$$R^u$; —$NR^k$S(O)$_n$$R^j$; or —P(O)(O$R'''$)(O$R''$); or (ii) $C_2$-$C_{20}$ alkenyl or $C_2$-$C_{20}$ alkynyl, each of which is optionally substituted with from 1-10 $R^s$; or (iii) $C_6$-$C_{16}$ aryl or heteroaryl including 5-16 atoms, each of which is optionally substituted with from 1-10 $R^g$;

$R^u$ is $R^j$, O$R^j$, or $NR'''R''$;

n is 0, 1 or 2; or a salt thereof.

2. The compound of claim 1, wherein each of $R^3$ and $R^4$, is, independently:
(i) halo; $NR'''R''$; nitro; hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$; —C(O)O$R^j$; —OC(O)$R^j$; —C(O)NR'''R''; —$NR^k$C(O)$R^j$; —OC(O)NR'''R''; —$NR^k$C(O)NR'''R''; —$NR^k$C(O)O$R^k$; —S(O)$_n$$R^u$; or —$NR^k$S(O)$_n$$R^j$; or (ii) $C_1$-$C_{12}$ alkyl, optionally substituted with from 1-10 $R^r$ and/or optionally inserted with from 1-10 heteroatoms selected from the group consisting of nitrogen, oxygen or sulfur; or (iii) $C_3$-$C_{20}$ cycloalkyl or $C_3$-$C_{20}$ halocycloalkyl, optionally substituted with from 1-10 $R^h$; or (iv) $C_2$-$C_{12}$ alkenyl or $C_2$-$C_{12}$ alkynyl, each of which is optionally substituted with from 1-10 $R^s$; or (v) $C_7$-$C_{12}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (vi) $C_6$-$C_{10}$ aryl or heteroaryl including 5-10 atoms, each of which is optionally substituted with from 1-10 $R^g$.

3. The compound of claim 1, wherein ring C is a fused $C_6$-$C_{16}$ aryl or a fused heteroaryl including 5-16 atoms, each of which is optionally substituted with from 1-10 $R^3$.

4. The compound of claim 3, wherein ring C is a fused phenyl ring, optionally substituted with from 1-3 $R^3$.

5. The compound of claim 3, wherein ring C is a fused heteroaryl including 5-10 atoms, each of which is optionally substituted with from 1-5 $R^3$.

6. The compound of claim 3, wherein $R^3$ is halo.

7. The compound of claim 3, wherein $R^3$ is $C_7$-$C_{10}$ aralkyl.

8. The compound of claim 7, wherein $R^3$ is benzyl.

9. The compound of claim 3, wherein $R^3$ is $C_1$-$C_6$ alkyl.

10. The compound of claim 3, wherein $R^3$ is $C_1$-$C_6$ alkoxy.

11. The compound of claim 3, wherein $R^3$ is $C_3$-$C_{10}$ cycloalkyl.

12. The compound of claim 11, wherein $R^3$ is:

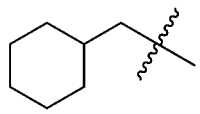

13. The compound of claim 3, wherein $R^3$ is —C(O)NR$^m$R$^n$.
14. The compound of claim 3, wherein $R^3$ —NR$^k$C(O)OR$^j$.
15. The compound of claim 3, wherein $R^3$ is —NR$^k$C(O)NR$^m$R$^n$.
16. The compound of claim 3, wherein $R^3$ is —NR$^k$C(O)R$^j$.
17. The compound of claim 3, wherein $R^3$ is —NR$^m$R$^n$.
18. The compound of claim 17, wherein one of R$^m$ and R$^n$ is hydrogen, and the other is $C_7$-$C_{10}$ aralkyl.
19. The compound of claim 18, wherein one of R$^m$ and R$^n$ is hydrogen, and the other is benzyl.
20. The compound of claim 17, wherein one of R$^m$ and R$^n$ is hydrogen, and the other is heterocyclyl including 3-10 atoms, optionally substituted with from 1-3 R$^i$.
21. The compound of claim 20, wherein one of R$^m$ and R$^n$ is hydrogen, and the other is tetrahydropyranyl.
22. The compound of claim 20, wherein one of R$^m$ and R$^n$ is hydrogen, and the other is:

wherein z is 1, 2, 3, 4, or 5.
23. The compound of claim 22, wherein R$^i$ is —C(O)OR$^j$, —C(O)NR$^m$R$^n$, or C(O)R$^j$.
24. The compound of claim 23, wherein R$^j$ is $C_1$-$C_6$ alkyl.
25. The compound of claim 23, wherein R$^j$ is $C_6$-$C_{10}$ aryl.
26. The compound of claim 23, wherein R$^j$ is heteroaryl including from 5-10 atoms.
27. The compound of claim 23, wherein R$^j$ is $C_7$-$C_{12}$ aralkyl.
28. The compound of claim 23, wherein R$^j$ is heteroaralkyl including from 7-12 atoms.
29. The compound of claim 23, wherein R$^j$ is heterocyclyl including from 3-8 atoms.
30. The compound of claim 23, wherein R$^j$ is $C_3$-$C_{10}$ cycloalkyl.
31. The compound of claim 23, wherein each of R$^m$ and R$^n$ is, independently of one another, hydrogen; $C_1$-$C_6$ alkyl; $C_6$-$C_{10}$ aryl; heteroaryl including from 5-10 atoms; or $C_3$-$C_{10}$ cycloalkyl.
32. The compound of claim 22, wherein R$^i$ is —SO$_2$R$^u$.
33. The compound of claim 32, wherein R$^u$ is $C_1$-$C_6$ alkyl.
34. The compound of claim 32, wherein R$^u$ is $C_7$-$C_{12}$ aralkyl.
35. The compound of claim 34, wherein R$^u$ is benzyl.
36. The compound of claim 32, wherein R$^u$ is $C_1$-$C_6$ haloalkyl.
37. The compound of claim 32, wherein R$^u$ is $C_6$-$C_{10}$ aryl.
38. The compound of claim 32, wherein R$^u$ is heteroaryl including from 5-10 atoms.
39. The compound of claim 32, wherein R$^u$ is heteroaralkyl including from 7-12 atoms.
40. The compound of claim 32, wherein R$^u$ is heterocyclyl including from 3-8 atoms.

41. The compound of claim 32, wherein R$^u$ is $C_3$-$C_{10}$ cycloalkyl.
42. The compound of claim 22, wherein z is 0, 1, or 2.
43. The compound of claim 17, wherein one of R$^m$ and R$^n$ is hydrogen, and the other is $C_3$-$C_{10}$ cycloalkyl.
44. The compound of claim 43, wherein one of R$^m$ and R$^n$ is hydrogen, and the other is cyclohexyl or

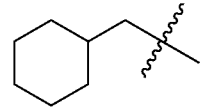

45. The compound of claim 1, wherein R$^1$ is cyano, —C(O)R$^j$, —C(O)OR$^j$, —C(O)SR$^j$, —C(S)SR$^j$, or —C(O)NR$^m$R$^n$.
46. The compound of claim 45, wherein R$^1$ is cyano.
47. The compound of claim 45, wherein R$^1$ is —C(O)OR$^j$.
48. The compound of claim 47, wherein R$^j$ is hydrogen.
49. The compound of claim 47, wherein R$^j$ is $C_1$-$C_6$ alkyl.
50. The compound of claim 1, wherein R$^1$ is tetrazolyl.
51. The compound of claim 1, wherein Z is NR$^p$($C_1$-$C_3$ alkylene).
52. The compound of claim 1, wherein Z is O($C_1$-$C_3$ alkylene).
53. The compound of claim 52, wherein Z is OCH$_2$.
54. The compound of claim 1, wherein W is O.
55. The compound of claim 1, wherein Z' is O.
56. The compound of claim 1, wherein R$^2$ is hydrogen.
57. The compound of claim 1, wherein R$^2$ is:
(i) $C_1$-$C_{16}$ alkyl, optionally substituted with from 1-10 R$^r$ and/or optionally inserted with from 1-10 heteroatoms selected from the group consisting of nitrogen, oxygen or sulfur; or
(ii) $C_7$-$C_{20}$ aralkyl, optionally substituted with from 1-10 R$^t$.
58. The compound of claim 1, wherein the compound has formula (VI):

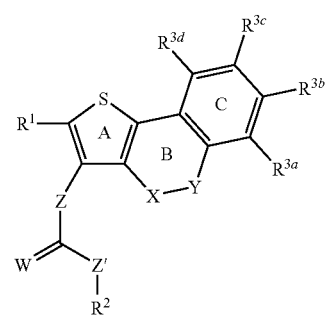

(VI)

wherein:
X, Y, R$^1$, R$^2$, W, Z, Z', and n are as defined in claim 1; and each of R$^{3a}$, R$^{3b}$, R$^{3c}$, and R$^{3d}$ is, independently:
(i) hydrogen, halo; NR$^m$R$^n$; nitro; azido, hydroxy; $C_1$-$C_{12}$ alkoxy, optionally substituted with 1-5 R$^r$; $C_1$-$C_{12}$ haloalkoxy; $C_6$-$C_{16}$ aryloxy, optionally substituted with 1-5 R$^g$; $C_2$-$C_{12}$ alkenyloxy or $C_2$-$C_{12}$ alkynyloxy, each of which is optionally substituted with 1-5 R$^s$; $C_3$-$C_{16}$ cycloalkyloxy or $C_3$-$C_{16}$ halocycloalkyloxy, each of which is optionally substituted with 1-5 R$^h$; heterocylyoxy including 3-16 atoms, optionally substituted with 1-5 R$^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; —NR$^k$C(O)$R^j$; —C(NR°)$R^j$; —OC(O)NR'''R''; —NR$^k$C(O)NR'''R''; —NR$^k$C(O)O$R^j$; —S(O)$_n$R$^u$; —NR$^k$S(O)$_n$R$^j$; or —P(O)(OR''')(OR''); or (ii) $C_1$-$C_{20}$ alkyl, optionally substituted with from 1-10 $R^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 $R^r$; or (iv) $C_3$-$C_{20}$ cycloalkyl or $C_3$-$C_{20}$ halocycloalkyl, optionally substituted with from 1-10 $R^h$; or (v) $C_3$-$C_{20}$ cycloalkenyl, heterocyclyl including 3-20 atoms, or heterocycloalkenyl including 3-20 atoms, each of which is optionally substituted with from 1-10 $R^i$; or (vi) $C_2$-$C_{20}$ alkenyl or $C_2$-$C_{20}$ alkynyl, each of which is optionally substituted with from 1-10 $R^s$;

(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$.

59. The compound of claim 58, wherein one of $R^{3a}$, $R^{3b}$, $R^{3c}$, and $R^{3d}$ is:

(i) halo; NR'''R''; nitro; azido, hydroxy; $C_1$-$C_{12}$ alkoxy, optionally substituted with 1-5 $R^r$; $C_1$-$C_{12}$ haloalkoxy; $C_6$-$C_{16}$ aryloxy, optionally substituted with 1-5 $R^g$; $C_2$-$C_{12}$ alkenyloxy or $C_2$-$C_{12}$ alkynyloxy, each of which is optionally substituted with 1-5 $R^s$; $C_3$-$C_{16}$ cycloalkyloxy or $C_3$-$C_{16}$ halocycloalkyloxy, each of which is optionally substituted with 1-5 $R^h$; heterocyclyloxy including 3-16 atoms, optionally substituted with 1-5 $R^i$; $C_7$-$C_{20}$ aralkoxy, optionally substituted with 1-5 $R^t$; mercapto; $C_1$-$C_6$ thioalkoxy; $C_6$-$C_{16}$ thioaryloxy; cyano; formyl; —C(O)$R^j$, $C_1$-$C_3$ alkylenedioxy; —C(O)O$R^j$; —OC(O)$R^j$; —C(O)S$R^j$; —SC(O)$R^j$; —C(S)S$R^j$; —SC(S)$R^j$; —C(O)NR'''R''; NR$^k$C(O)$R^j$—C(NR°)$R^j$; —OC(O)NR'''R''; —NR$^k$C(O)NR'''R''; —NR$^k$C(O)O$R^j$; —S(O)$_n$R$^u$; —NR$^k$S(O)$_n$R$^j$; or —P(O)(OR''')(OR''); or (ii) $C_1$-$C_{20}$ alkyl, optionally substituted with from 1-10 $R^r$ and/or optionally inserted with from 1-10 heteroatoms selected from the group consisting of nitrogen, oxygen or sulfur; or (iii) $C_1$-$C_{20}$ haloalkyl, optionally substituted with from 1-10 $R^r$; or (iv) $C_3$-$C_{20}$ cycloalkyl or $C_3$-$C_{20}$ halocycloalkyl, optionally substituted with from 1-10 $R^h$; or (v) $C_3$-$C_{20}$ cycloalkenyl, heterocyclyl including 3-20 atoms, or heterocycloalkenyl including 3-20 atoms, each of which is optionally substituted with from 1-10 $R^i$; or (vi) $C_2$-$C_{20}$ alkenyl or $C_2$-$C_{20}$ alkynyl, each of which is optionally substituted with from 1-10 $R^s$;

(vii) $C_7$-$C_{20}$ aralkyl, heteroaralkyl including 6-20 atoms, $C_8$-$C_{20}$ arylcycloalkyl, $C_8$-$C_{20}$ arylcycloalkenyl, arylheterocyclyl including 8-20 atoms, or arylheterocycloalkenyl including 8-20 atoms, each of which is optionally substituted with from 1-10 $R^t$; or (viii) $C_6$-$C_{16}$ aryl or heteroaryl including 5-16 atoms, each of which is optionally substituted with from 1-10 $R^g$; and the other three are each hydrogen.

60. The compound of claim 59, wherein $R^{3a}$ is halo, $C_1$-$C_6$ alkyl, $C_1$-$C_6$ alkoxy, —NR$^k$C(O)O$R^j$, —NR$^k$C(O)NR'''R'', —NR$^k$C(O)$R^j$, or —NR'''R'', and $R^{3b}$, $R^{3c}$, and $R^{3d}$ each are hydrogen.

61. The compound of claim 59, wherein $R^{3b}$ is halo, $C_1$-$C_6$ alkyl, $C_1$-$C_6$ alkoxy, $C_3$-$C_{10}$ cycloalkyl, $C_7$-$C_{10}$ aralkyl, —C(O)O$R^j$, —C(O)NR'''R'', —NR$^k$C(O)O$R^j$, —NR$^k$C(O)NR'''R'', —NR$^k$C(O)$R^j$, or —NR'''R'', and $R^{3a}$, $R^{3c}$, and $R^{3d}$ each are hydrogen.

62. A pharmaceutical composition comprising a compound of formula (I), according to claim 1 or a pharmaceutically acceptable salt thereof, and a pharmaceutically acceptable carrier.

63. A method of treating type 2 diabetes, the method comprising administering to a subject in need thereof an effective amount of a compound of formula (I) according to claim 1.

64. A method of treating obesity, the method comprising administering to a subject in need thereof an effective amount of a compound of formula (I) according to claim 1.

65. A method of increasing insulin sensitivity, the method comprising administering to a subject in need thereof an effective amount of a compound of formula (I) according to claim 1.

* * * * *